United States Patent
Gundram et al.

(10) Patent No.: US 10,906,952 B2
(45) Date of Patent: Feb. 2, 2021

(54) FUSION PROTEINS COMPRISING A BINDING PROTEIN AND AN INTERLEUKIN-15 POLYPEPTIDE HAVING A REDUCED AFFINITY FOR IL15RA AND THERAPEUTIC USES THEREOF

(71) Applicants: DEUTSCHES KREBSFORSCHUNGSZENTRUM, Heidelberg (DE); EBERHARD KARLS UNIVERSITÄT TÜBINGEN, Tübingen (DE)

(72) Inventors: Jung Gundram, Rottenburg (DE); Helmut Salih, Stuttgart (DE); Cornelia Lindner, Laupheim (DE); Berit Lochmann, Mannheim (DE)

(73) Assignees: DEUTSCHES KREBSFORSCHUNGSZENTRUM, Heidelberg (DE); EBERHARD KARLS UNIVERSITÄT TÜBINGEN, Tübingen (DE)

( * ) Notice: Subject to any disclaimer, the term of this patent is extended or adjusted under 35 U.S.C. 154(b) by 17 days.

(21) Appl. No.: 15/556,282

(22) PCT Filed: Mar. 7, 2016

(86) PCT No.: PCT/EP2016/054729
§ 371 (c)(1),
(2) Date: Jan. 8, 2018

(87) PCT Pub. No.: WO2016/142314
PCT Pub. Date: Sep. 15, 2016

(65) Prior Publication Data
US 2018/0044391 A1  Feb. 15, 2018

(30) Foreign Application Priority Data
Mar. 6, 2015 (EP) .................................. 15157911

(51) Int. Cl.
| C07K 14/54 | (2006.01) |
| --- | --- |
| C07K 16/18 | (2006.01) |
| C07K 16/28 | (2006.01) |
| C07K 16/30 | (2006.01) |
| C07K 19/00 | (2006.01) |
| A61K 38/00 | (2006.01) |

(52) U.S. Cl.
CPC .......... *C07K 14/5443* (2013.01); *C07K 16/18* (2013.01); *C07K 16/28* (2013.01); *C07K 16/2803* (2013.01); *C07K 16/30* (2013.01); *C07K 16/3069* (2013.01); *C07K 19/00* (2013.01); *A61K 38/00* (2013.01); *C07K 2317/41* (2013.01); *C07K 2317/526* (2013.01); *C07K 2317/72* (2013.01); *C07K 2317/732* (2013.01); *C07K 2319/00* (2013.01); *C07K 2319/33* (2013.01); *C07K 2319/74* (2013.01); *C07K 2319/75* (2013.01)

(58) Field of Classification Search
None
See application file for complete search history.

(56) References Cited

U.S. PATENT DOCUMENTS

| 2009/0324538 A1* | 12/2009 | Wong ............... C07K 14/5443 424/85.2 |
| --- | --- | --- |
| 2011/0158938 A1* | 6/2011 | Bernard .................. C07K 7/06 424/85.2 |
| 2019/0263877 A1 | 8/2019 | Yeung et al. |

FOREIGN PATENT DOCUMENTS

| CN | 1867583 A | 11/2006 |
| --- | --- | --- |
| JP | 2007528726 A | 10/2007 |
| JP | 2008523132 | 7/2008 |
| WO | WO 2004/099249 A2 | 11/2004 |
| WO | 2005/085282 A1 | 9/2005 |
| WO | 2006/063974 A2 | 6/2006 |
| WO | WO 2012/040323 A2 | 3/2012 |
| WO | WO 2014/2071743 A1 | 12/2014 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Antibody Mimetic, Retrieved from "https://en.wikipedia.org/w/index.php?title=Antibody_mimetic&oldid=81208732"2, Nov. 25, 2017, 2 pages.
Avimer, Retrieved from "https://en.wikipedia.org/w/index.php?title=Avimer&oldid=702868839" on Feb. 2, 2016, 2 pages.
Monobody, Retrieved from https://en.wikipedia.org/w/index.php?title=Monobody&oldid=807139681, Oct. 26, 2017, 4 pages.
Napolitano et al., "Glubodies: radomized libraries of glutathione transferase enzymes," Chemistry & Biology 3:359-367 (1996).
Skerra, A. "Engineered protein scaffolds for molecular recognition," J. Mol. Recognit. 2000;13:167-187.

(Continued)

*Primary Examiner* — Bridget E Bunner
*Assistant Examiner* — Fozia Hamud

(57) ABSTRACT

The present invention relates to fusion proteins comprising a binding protein and an IL-15 polypeptide as well as uses thereof, pharmaceutical compositions comprising such fusion proteins and a method for producing such fusion proteins.

15 Claims, 18 Drawing Sheets
Specification includes a Sequence Listing.

(56) References Cited

OTHER PUBLICATIONS

Skerra, A. "Anticalins': a new class of engineered ligand-binding proteins with antibody-like properties," Reviews in Molecular Biotechnology 74:257-275 (2001).

Dafne Mueller, "Targeted Cancer Immunotherapy: Mimicking physiological trans-presentation of IL-15," OncoImmunology 1(7): 1213-1214, Oct. 2012.

Albertini, M., et al., "Phase II trial of hu14.18-IL2 for patients with metastatic melanoma," Cancer Immunol Immunother 61:2261-2271 (2012).

Bernard, J., et al., "Identification of an Interleukin-15α Receptor-binding Site on Human Interleukin-15," The Journal of Biological Chemistry 279(23)24313-24322 (2004).

Conlon, K., et al., "Redistribution, Hyperproliferation, Activation of Natural Killer Cells and CD8 T Cells, and Cytokine Production During First-in-Human Clinical Trial of Recombinant Human Interleukin-15 in Patients With Cancer," Journal of Clinical Oncology vol. 33, No. 1 (2015), 17 pages.

Garcin, G., et al., "High efficiency cell-specific targeting of cytokine activity," Nature Communications, vol. 5, No. 3016, 2014, 9 pages.

Gillies, S., et al., "Antibody-targeted interleukin 2 stimulates T-cell killing of Autologous tumor cells," Immunology 89:1428-1432 (1992).

Hofmann, M. et al., "Generation, selection and preclinical characterization of an Fc-optimized FLT3 antibody for the treatment of myeloid leukemia," Leukemia 26:1228-1237 (2012).

Horton, H., et al., "Potent in vitro and in vivo Activity of an Fc-Engineered Anti-CD19 Monoclonal Antibody against Lymphoma and Leukemia," Cancer Research, vol. 68, No. 19, 2008, 10 pages.

Kaspar, M., et al., "The Antibody-Mediated Targeted Delivery of Interleukin-15 and GM-CSF to the Tumor Neovasculature Inhibits Tumor Growth and Metastasis," Cancer Research 67(10):4940-4948 (2007).

Kellner, C., et al., "Heterodimeric bispecific antibody-deriva tives against CD19 and CD16 induce effective antibody-dependent cellular cytotoxicily against 8-lymphoid tumor cells," Cancer Letters 303:128-139 (2011).

Kermer, V., et al.,"An Antibody Fusion Protein for Cancer Immunotherapy Mimicking IL-15 trans-Presentation at the Tumor Site," Molecular Cancer Therapeutics 11(6):1279-1288 (2012).

List, T., et al., "Immunocytokines: A review of molecules in clinical development for cancer therapy," Clinical Phannacology: Advances and Applications 5(S1):29-45 (2013).

Notice of Opposition by Margaret Dixon Limited to Patent No. EP3265478 filed in the European Patent Office for Application No. 16708154.6, dated Jun. 16, 2020, 5 pages.

Notice of Opposition by Pfizer to Patent No. EP3265478 filed in the European Patent Office for Application No. 16708154.6, dated Jun. 16, 2020, 6 pages.

Ortiz-Sanchez E. et al., "Antibody-Cytokine Fusion Proteins: Applications in Cancer Therapy," Expert Opin Biol Ther 8(5):609-632 (2008).

Ribas, A., et al., "Phase I/II open-label study of the biologic effects of the interleukin-2 immunocytokine EMD 273063 (hu I 4.18-IL2) in patients with metastatic malignant melanoma," Journal of Translational Medicine, vol. 7, No. 68, 2009, 11 pages.

Zhu, X., et al. "Novel Human Interleukin-15 Agonists," The Journal of Immunology 183:3598-3607 (2009).

Accession: CAD88275, anti-human CD19 monoclonal antibody 4G7 immunoglobulin gammal heavy chain [Mus musculus], Hofmann, M. et al., GenBank, dated Jan. 15, 2013, 2 pages.

Accession: CAD88204, anti-human CD19 monoclonal antibody 4G7 immunoglobulin Kappa light chain [Mus musculus], Hofmann, M. et al., GenBank, dated Jan. 4, 2013 1 page.

Chen et al., "Fusion protein linkers: Property, design and functionality," Advanced Drug Delivery Reviews, vol. 65, Issue 10, pp. 1357-1369 (2013).

Generierung, präklinische Charakterisierung und Optimierung monoklonaler Antikörper zur anti-angiogenetischen Therapie solider Tumoren, Schwartz, K, Library of Eberhard Karls Universität Tübingen, pp. 1-150 (2013).

Zhou, C. et al., editor, "Microbiology and Immunology," p. 329, China Medical Science and Technology Press, Jul. 31, 2013, 6 pages, including English translation of relevant part.

* cited by examiner

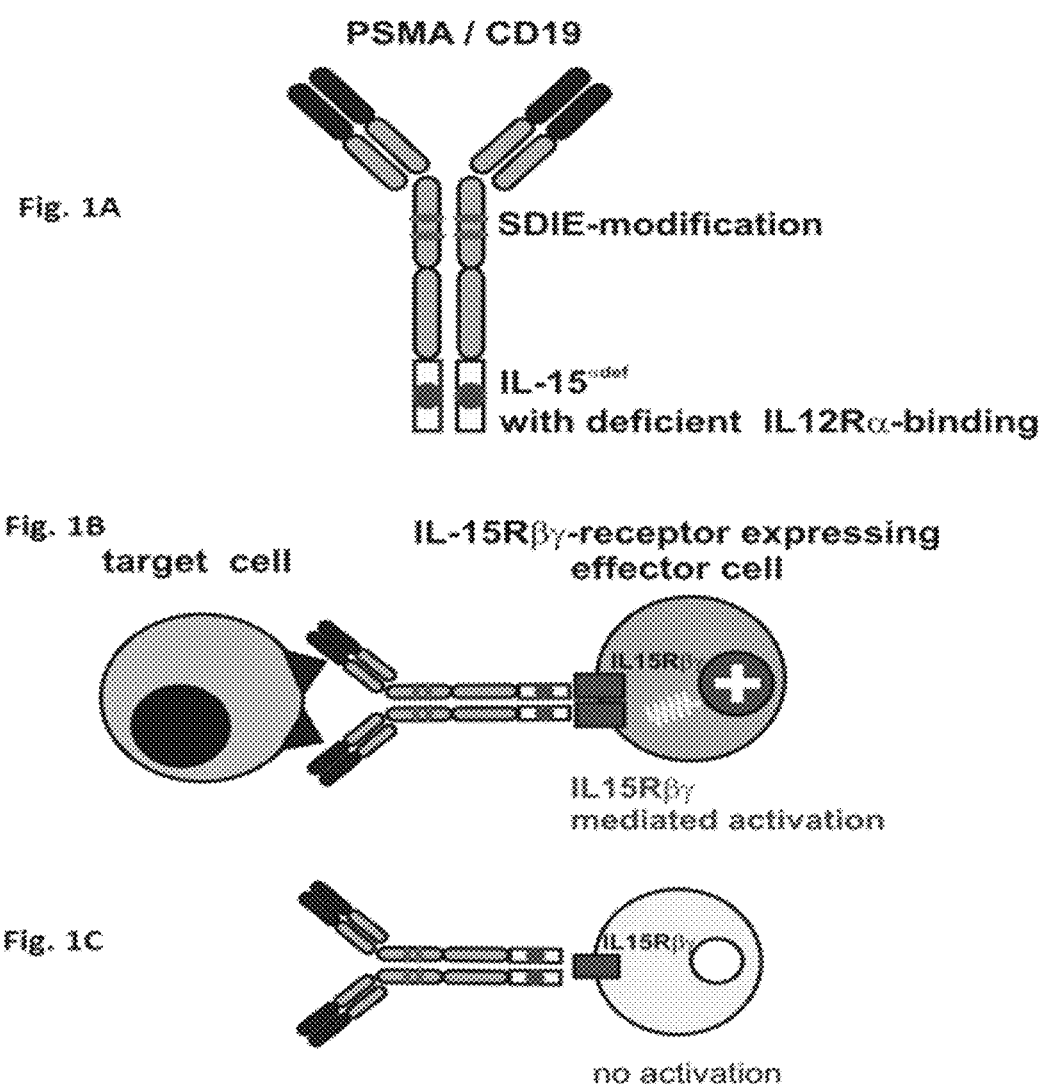

Fig. 2: Binding to IL-15Rα and cytolytic activity of fusion proteins

Fig. 3: Selection of the linker

Fig. 4: Target cell restricted NK cell activation and target cell killing

SEQ ID NO: 1

MRISKPHLRSISIQCYLCLLLNSHFLTEAGIHVFILGCFSAGLPKTEANWVNVISDLKKIE
DLIQSMHIDATLYTESDVHPSCKVTAMKCFLLELQVISLESGDASIHDTVENLILANNSL
SSNGNVTESGCKECEELEEKNIKEFLQSFVHIVQMFINTS

SEQ ID NO: 2 $^{44}$LLELQVISL$^{52}$ (α binding)

SEQ ID NO: 3 $^{64}$ENLII$^{68}$ (α binding)

SEQ ID NO: 4

1  NWVNVISDLK KIEDLIQSMH IDATLYTESD VHPSCKVTAM KCFLLELQVI SLESGDASIH  60

61 DTVENLILAN NSLSSNGNVT ESGCKECEEL EEKNIKEFLQ SFVHIVQMFI NTS 114

SEQ ID NO: 5 – Anti-CD19 single variable domain VH (clone 4G7) (CDR regions underlined)

EVQLQQSGPELIKPGASVKMSCKASGYTFTSYVMHWVKQKPGQGLEWIGYINPYNDGTKY
NEKFKGKATLTSDKSSSTAYMELSSLTSEDSAVYYCARGTYYYGSRVFDYWGQGTTLTVSS

SEQ ID NO: 6 – Anti-CD19 single variable domain VL (clone 4G7) (CDR regions underlined)

DIVMTQAAPSIPVTPGESVSISCRSSKSLLNSNGNTYLYWFLQRPGQSPQLLIYRMSNLASGV
PDRFSGSGSGTAFTLRISRVEAEDVGVYYCMQHLEYPFTFGAGTKLELK

SEQ ID NO: 7 anti-FLT3 single variable domain VH (clone BV10)
QVQLKQSGPGLVQPSQSLSITCTVSGFSLTNYGLHWVRQSPGKGLEWLGVIWSGGSTDYN
AAFISRLSISKDNSKSQVFFKMNSLQADDTAIYYCARKGGIYYANHYYAMDYWGQGTSVTVS
S

SEQ ID NO: 8 anti-FLT3 single variable domain (clone BV10), VL CDR regions underlined DIVMTQSPSSLSVSAGEKVTMSCKSSQSLLNSGNQKNYMAWYQQKPGQPPKLLIYGASTRE
SGVPDRFTGSGSGTDFTLTISSVQAEDLAVYYCQNDHSYPLTFGAGTKLELK

SEQ ID NO: 9 anti-FLT3 chimeric single variable domain heavy chain (clone 4G8) VH
QVQLQQPGAELVKPGASLKLSCKSSGYTFTSYWMHWVRQRPGHGLEWIGEIDPSDSYKDY
NQKFKDKATLTVDRSSNTAYMHLSSLTSDDSAVYYCARAITTTPFDFWGQGTTLTVSS

SEQ ID NO: 10 anti-FLT3 chimeric single variable domain light chain (clone 4G8) VL

Fig. 5B

DIVLTQSPATLSVTPGDSVSLSC<u>RASQSISNNL</u>HWYQQKSHESPRLLIK<u>YASQSIS</u>GIPSRFSG
SGSGTDFTLSINSVETEDFGVYFC<u>QQSNTWPYT</u>FGGGTKLEIK

SEQ ID NO: 11 anti-PSMA single variable domain heavy chain (clone J591) VH

EVQLQQSGPELVKPGTSVRISCKTSGYTFT<u>EYTI</u>HWVKQSHGKSLEWIG<u>NI
NPNNGGTTYNQKFED</u>KATLTVDKSSSTAYMELRSLTSEDSAVYYCAA<u>GWNF D</u>YWGQGTTLTVSS

SEQ ID NO: 12 anti-PSMA single variable domain light chain (clone J591) VL

NIVMTQSPKSMSMSVGERVTLTC<u>KASENVVTYVS</u>WYQQKPEQSPKLLIY<u>GA
SNRYT</u>GVPDRFTGSGSATDFTLTISSVQAEDLADYHC<u>GQGYSYPYT</u>FGGGT KLEIK

SEQ ID NO: 25 anti-endoglin single variable domain heavy chain (clone K-ro23) VH EVQLQQSGADLVRSGAAVKLSCTAS<u>GFNIKDYYLH</u>WVKQRPEQGLEWIG<u>WIDPENGDTEY
APKFQD</u>KATMTADSSSNTAYLQLNSLTSEDTGVYYCNT<u>RYGTSSAC</u>WGQGTTLTVSS

SEQ ID NO: 26 anti-endoglin single variable domain light chain (clone K-ro23) VL QIVLTQSPALMSASPGEKVTMTC<u>SASSSVSYMY</u>WYQQRPRSSPKPWIY<u>LTSNLAS</u>GVPARF
SGSGSGTSYSLTISSMEAEDAATYYC<u>QQWSSNPLT</u>FGAGTKLELK

Fig. 6

SEQ ID NO: 27 Fusion protein of anti-endoglin IgG1 (K-ro23) heavy chain with SDIE modifications and IL15 mutant EVQLQQSGADLVRSGAAVKLSCTASGFNIKDYYLHWVKQRPEQGLEWIGWIDPENGDTEYAPKFQDKATMTADSSSN
<br>K-ro23-VH TAYLQLNSLTSEDTGVYYCNTRYGTSSACWGQGTTLTVSSASTKGPSVFPLAPSSKSTSGGTAALGCLVKDYFPEPVTVS
<br>CH1

WNSGALTSGVHTFPAVLQSSGLYSLSSVVTVPSSSLGTQTYICNVNHKPSNTKVDKKVEPKSCDKTHTCPPCPAPELLGG
<br>Hinge PDVFLFPPKPKDTLMISRTPEVTCVVVDVSHEDPEVKFNWYVDGVEVHNAKTKPREEQYNSTYRVVSVLTVLHQDWLN
<br>CH2

GKEYKCKVSNKALPAPEEKTISKAKGQPREPQVYTLPPSRDELTKNQVSLTCLVKGFYPSDIAVEWESNGQPENNYKTTP
<br>CH3

PVLDSDGSFFLYSKLTVDKSRWQQGNVFSCSVMHEALHNHYTQKSLSLSPGKSGGGGSGGGGSGGGGSGGGGSNWV
<br>Linker NVISDLKKIEDLIQSMHIDATLYTESDVHPSCKVTAMKCFLLELQVISLESGDASIHDTVENLIILANNSLSSNGNVTESGCK
<br>IL15mut

ECEELEEKNIKEFLQSFVHIVQMFINTS

SEQ ID NO: 28 anti-endoglin IgG1 (K-ro23) light chain

QIVLTQSPALMSASPGEKVTMTCSASSSVSYMYWYQQRPRSSPKPWIYLTSNLASGVPARFSGSGSGTSYSLTISSMEAED
<br>K-ro23-VL

AATYYCQQWSSNPLTFGAGTKLELKRTVAAPSVFIFPPSDEQLKSGTASVVCLLNNFYPREAKVQWKVDNALQSGNSQES
<br>CL

VTEQDSKDSTYSLSSTLTLSKADYEKHKVYACEVTHQGLSSPVTKSFNRGEC

Fig. 7A

SEQ ID NO: 29 Fusion protein of anti-CD19 IgG1 (4G7) heavy chain with SDIE modifications and IL15 wild type with short linker EVQLQQSGPELIKPGASVKMSCKASGYTFTSYVMHWVKQKPGQGLEWIGYINPYNDGTKYNEKFKGKATLTSDKSSST
        4G7-VH AYMELSSLTSEDSAVYYCARGTYYYGSRVFDYWGQGTTLTVSSASTKGPSVFPLAPSSKSTSGGTAALGCLVKDYFPEPVTVS
        CH1

WNSGALTSGVHTFPAVLQSSGLYSLSSVVTVPSSSLGTQTYICNVNHKPSNTKVDKKVEPKSCDKTHTCPPCPAPELLGG
        Hinge PDVFLFPPKPKDTLMISRTPEVTCVVVDVSHEDPEVKFNWYVDGVEVHNAKTKPREEQYNSTYRVVSVLTVLHQDWLN
        CH2

GKEYKCKVSNKALPAPEEKTISKAKGQPREPQVYTLPPSRDELTKNQVSLTCLVKGFYPSDIAVEWESNGQPENNYKTTP
        CH3

PVLDSDGSFFLYSKLTVDKSRWQQGNVFSCSVMHEALHNHYTQKSLSLSPGKGSNWVNVISDLKKIEDLIQSMHIDAT
        Linker LYTESDVHPSCKVTAMKCFLLELQVISLESGDASIHDTVENLIILANNSLSSNGNVTESGCKECEELEEKNIKEFLQSFVHIV
        IL15mut

QMFINTS

SEQ ID NO: 30 Fusion protein of anti-CD19 IgG1 (4G7) heavy chain with SDIE modifications and IL15 (E46K) mutant with short linker EVQLQQSGPELIKPGASVKMSCKASGYTFTSYVMHWVKQKPGQGLEWIGYINPYNDGTKYNEKFKGKATLTSDKSSST
        4G7-VH AYMELSSLTSEDSAVYYCARGTYYYGSRVFDYWGQGTTLTVSSASTKGPSVFPLAPSSKSTSGGTAALGCLVKDYFPEPVTVS
        CH1

WNSGALTSGVHTFPAVLQSSGLYSLSSVVTVPSSSLGTQTYICNVNHKPSNTKVDKKVEPKSCDKTHTCPPCPAPELLGG
        Hinge PDVFLFPPKPKDTLMISRTPEVTCVVVDVSHEDPEVKFNWYVDGVEVHNAKTKPREEQYNSTYRVVSVLTVLHQDWLN
        CH2

GKEYKCKVSNKALPAPEEKTISKAKGQPREPQVYTLPPSRDELTKNQVSLTCLVKGFYPSDIAVEWESNGQPENNYKTTP
        CH3

PVLDSDGSFFLYSKLTVDKSRWQQGNVFSCSVMHEALHNHYTQKSLSLSPGKGSNWVNVISDLKKIEDLIQSMHIDAT
        Linker

Fig. 7B

LYTESDVHPSCKVTAMKCFLLKLQVISLESGDASIHDTVENLIILANNSLSSNGNVTESGCKECEELEEKNIKEFLQSFVHIV
<p align="center">IL15mut</p>

QMFINTS

SEQ ID NO: 31 Fusion protein of anti-CD19 IgG1 (4G7) heavy chain with SDIE modifications and IL15 (V49D) mutant with short linker EVQLQQSGPELIKPGASVKMSCKASGYTFTSYVMHWVKQKPGQGLEWIGYINPYNDGTKYNEKFKGKATLTSDKSSST
<p align="center">4G7 VH</p>

AYMELSSLTSEDSAVYYCARGTYYYGSRVFDYWGQGTTLTVSSASTKGPSVFPLAPSSKSTSGGTAALGCLVKDYFPEPVTVS
<p align="right">CH1</p>

WNSGALTSGVHTFPAVLQSSGLYSLSSVVTVPSSSLGTQTYICNVNHKPSNTKVDKKVEPKSCDKTHTCPPCPAPELLGG
<p align="right">Hinge</p>

PDVFLFPPKPKDTLMISRTPEVTCVVVDVSHEDPEVKFNWYVDGVEVHNAKTKPREEQYNSTYRVVSVLTVLHQDWLN
<p align="center">CH2</p>

GKEYKCKVSNKALPAPEEKTISKAKGQPREPQVYTLPPSRDELTKNQVSLTCLVKGFYPSDIAVEWESNGQPENNYKTTP
<p align="right">CH3</p>

PVLDSDGSFFLYSKLTVDKSRWQQGNVFSCSVMHEALHNHYTQKSLSLSPGKGSNWVNVISDLKKIEDLIQSMHIDAT
<p align="right">Linker</p>

LYTESDVHPSCKVTAMKCFLLELQDISLESGDASIHDTVENLIILANNSLSSNGNVTESGCKECEELEEKNIKEFLQSFVHIV
<p align="center">IL15mut</p>

QMFINTS

SEQ ID NO: 32 Fusion protein of anti-CD19 IgG1 (4G7) heavy chain with SDIE modifications and IL15 (I50D) mutant with short linker EVQLQQSGPELIKPGASVKMSCKASGYTFTSYVMHWVKQKPGQGLEWIGYINPYNDGTKYNEKFKGKATLTSDKSSST
<p align="center">4G7 VH</p>

AYMELSSLTSEDSAVYYCARGTYYYGSRVFDYWGQGTTLTVSSASTKGPSVFPLAPSSKSTSGGTAALGCLVKDYFPEPVTVS
<p align="right">CH1</p>

WNSGALTSGVHTFPAVLQSSGLYSLSSVVTVPSSSLGTQTYICNVNHKPSNTKVDKKVEPKSCDKTHTCPPCPAPELLGG
<p align="right">Hinge</p>

Fig. 7C

PDVFLFPPKPKDTLMISRTPEVTCVVVDVSHEDPEVKFNWYVDGVEVHNAKTKPREEQYNSTYRVVSVLTVLHQDWLN
CH2

GKEYKCKVSNKALPAPEEKTISKAKGQPREPQVYTLPPSRDELTKNQVSLTCLVKGFYPSDIAVEWESNGQPENNYKTTP
CH3

PVLDSDGSFFLYSKLTVDKSRWQQGNVFSCSVMHEALHNHYTQKSLSLSPGKGS*NWVNVISDLKKIEDLIQSMHIDAT*
Linker

*LYTESDVHPSCKVTAMKCFLLELQV*D*SLESGDASIHDTVENLIILANNSLSSNGNVTESGCKECEELEEKNIKEFLQSFVHIV*
IL15mut

*QMFINTS*

SEQ ID NO: 33 Fusion protein of anti-CD19 IgG1 (4G7) heavy chain with SDIE modifications and IL15 wild type with long linker

EVQLQQSGPELIKPGASVKMSCKASGYTFTSYVMHWVKQKPGQGLEWIGYINPYNDGTKYNEKFKGKATLTSDKSSST
4G7-VH

AYMELSSLTSEDSAVYYCARGTYYYGSRVFDYWGQGTTLTVSSASTKGPSVFPLAPSSKSTSGGTAALGCLVKDYFPEPVTVS
CH1

WNSGALTSGVHTFPAVLQSSGLYSLSSVVTVPSSSLGTQTYICNVNHKPSNTKVDKKV*EPKSCDKTHTCPPCP*APELLGG
Hinge PDVFLFPPKPKDTLMISRTPEVTCVVVDVSHEDPEVKFNWYVDGVEVHNAKTKPREEQYNSTYRVVSVLTVLHQDWLN
CH2

GKEYKCKVSNKALPAPEEKTISKAKGQPREPQVYTLPPSRDELTKNQVSLTCLVKGFYPSDIAVEWESNGQPENNYKTTP
CH3

PVLDSDGSFFLYSKLTVDKSRWQQGNVFSCSVMHEALHNHYTQKSLSLSPGKSGGGGSGGGGSGGGGSGGGGS*NWV*
Linker

*NVISDLKKIEDLIQSMHIDATLYTESDVHPSCKVTAMKCFLLELQVISLESGDASIHDTVENLIILANNSLSSNGNVTESGCK*
IL15mut

*ECEELEEKNIKEFLQSFVHIVQMFINTS*

SEQ ID NO: 34 Fusion protein of anti-CD19 IgG1 (4G7) heavy chain with SDIE modifications and IL15 (E46K) mutant with long linker

EVQLQQSGPELIKPGASVKMSCKASGYTFTSYVMHWVKQKPGQGLEWIGYINPYNDGTKYNEKFKGKATLTSDKSSST
4G7-VH

Fig. 7D

AYMELSSLTSEDSAVYYCARGTYYYGSRVFDYWGQGTTLTVSSASTKGPSVFPLAPSSKSTSGGTAALGCLVKDYFPEPVTVS
　　　　　　　　　　　　　　　　　　　　　　　　CH1

WNSGALTSGVHTFPAVLQSSGLYSLSSVVTVPSSSLGTQTYICNVNHKPSNTKVDKKVEPKSCDKTHTCPPCPAPELLGG
　　　　　　　　　　　　　　　　　　　　　　　　　　　　　　　Hinge PDVFLFPPKPKDTLMISRTPEVTCVVVDVSHEDPEVKFNWYVDGVEVHNAKTKPREEQYNSTYRVVSVLTVLHQDWLN
　　　　　　　　　　　　　　　　　CH2

GKEYKCKVSNKALPAPEEKTISKAKGQPREPQVYTLPPSRDELTKNQVSLTCLVKGFYPSDIAVEWESNGQPENNYKTTP
　　　　　　　　　　　　　　　　　　　　　　　　CH3

PVLDSDGSFFLYSKLTVDKSRWQQGNVFSCSVMHEALHNHYTQKSLSLSPGKSGGGGSGGGGSGGGGSGGGGSNWV
　　　　　　　　　　　　　　　　　　　　　　　　　　　　　Linker NVISDLKKIEDLIQSMHIDATLYTESDVHPSCKVTAMKCFLLELQDISLESGDASIHDTVENLIILANNSLSSNGNVTESGCK
　　　　　　　　　　　　　　　　　IL15mut

ECEELEEKNIKEFLQSFVHIVQMFINTS

SEQ ID NO: 35 Fusion protein of anti-CD19 IgG1 (4G7) heavy chain with SDIE modifications and IL15 (V49D) mutant with long linker EVQLQQSGPELIKPGASVKMSCKASGYTFTSYVMHWVKQKPGQGLEWIGYINPYNDGTKYNEKFKGKATLTSDKSSST
　　　　　　　　　　　　　　　　　　　　4G7 VH AYMELSSLTSEDSAVYYCARGTYYYGSRVFDYWGQGTTLTVSSASTKGPSVFPLAPSSKSTSGGTAALGCLVKDYFPEPVTVS
　　　　　　　　　　　　　　　　　　　　　　　　CH1

WNSGALTSGVHTFPAVLQSSGLYSLSSVVTVPSSSLGTQTYICNVNHKPSNTKVDKKVEPKSCDKTHTCPPCPAPELLGG
　　　　　　　　　　　　　　　　　　　　　　　　　　　　　　　Hinge PDVFLFPPKPKDTLMISRTPEVTCVVVDVSHEDPEVKFNWYVDGVEVHNAKTKPREEQYNSTYRVVSVLTVLHQDWLN
　　　　　　　　　　　　　　　　　CH2

GKEYKCKVSNKALPAPEEKTISKAKGQPREPQVYTLPPSRDELTKNQVSLTCLVKGFYPSDIAVEWESNGQPENNYKTTP
　　　　　　　　　　　　　　　　　　　　　　　　CH3

PVLDSDGSFFLYSKLTVDKSRWQQGNVFSCSVMHEALHNHYTQKSLSLSPGKSGGGGSGGGGSGGGGSGGGGSNWV
　　　　　　　　　　　　　　　　　　　　　　　　　　　　　Linker NVISDLKKIEDLIQSMHIDATLYTESDVHPSCKVTAMKCFLLELQDISLESGDASIHDTVENLIILANNSLSSNGNVTESGCK
　　　　　　　　　　　　　　　　　IL15mut

ECEELEEKNIKEFLQSFVHIVQMFINTS

Fig. 7E

SEQ ID NO: 36 Fusion protein of anti-CD19 IgG1 (4G7) heavy chain with SDIE modifications and IL15 (I50D) mutant with long linker EVQLQQSGPELIKPGASVKMSCKASGYTFTSYVMHWVKQKPGQGLEWIGYINPYNDGTKYNEKFKGKATLTSDKSSST
                4G7-VH AYMELSSLTSEDSAVYYCARGTYYYGSRVFDYWGQGTTLTVSSASTKGPSVFPLAPSSKSTSGGTAALGCLVKDYFPEPVTVS
                                CH1

WNSGALTSGVHTFPAVLQSSGLYSLSSVVTVPSSSLGTQTYICNVNHKPSNTKVDKKVEPKSCDKTHTCPPCPAPELLGG
                                 Hinge PDVFLFPPKPKDTLMISRTPEVTCVVVDVSHEDPEVKFNWYVDGVEVHNAKTKPREEQYNSTYRVVSVLTVLHQDWLN
                             CH2

GKEYKCKVSNKALPAPEEKTISKAKGQPREPQVYTLPPSRDELTKNQVSLTCLVKGFYPSDIAVEWESNGQPENNYKTTP
                                CH3

PVLDSDGSFFLYSKLTVDKSRWQQGNVFSCSVMHEALHNHYTQKSLSLSPGKSGGGGSGGGGSGGGGSGGGGS*NWV*
                                        Linker

*NVISDLKKIEDLIQSMHIDATLYTESDVHPSCKVTAMKCFLLELQVDSLESGDASIHDTVENLIILANNSLSSNGNVTESGCK*
                              IL15mut

*ECEELEEKNIKEFLQSFVHIVQMFINTS*

SEQ ID NO: 37 anti-CD19 IgG1 (4G7) light chain

DIVMTQAAPSIPVTPGESVSISCRSSKSLLNSNGNTYLYWFLQRPGQSPQLLIYRMSNLASGVPDRFSGSGSGTAFTLRISRVEAE
                               4G7-VL

DVGVYYCMQHLEYPFTFGAGTKLELKRTVAAPSVFIFPPSDEQLKSGTASVVCLLNNFYPREAKVQWKVDNALQSGNSQES
                                         CL

VTEQDSKDSTYSLSSTLTLSKADYEKHKVYACEVTHQGLSSPVTKSFNRGEC

Fig. 8

SEQ ID NO: 38 Fusion protein of anti-FLT3 IgG1 (BV10) heavy chain with SDIE modifications and IL15 mutant QVQLKQSGPGLVQPSQSLSITCTVSGFSLTNYGLHWVRQSPGKGLEWLGVIWSGGSTDYNAAFISRLSISKDNSKSQVFFKMN
<u>BV10-VH</u>

SLQADDTAIYYCARKGGIYYANHYYAMDYWGQGTSVTVSSASTKGPSVFPLAPSSKSTSGGTAALGCLVKDYFPEPVTVS
<u>CH1</u>

WNSGALTSGVHTFPAVLQSSGLYSLSSVVTVPSSSLGTQTYICNVNHKPSNTKVDKKVEPKSCDKTHTCPPCPAPELLGG
<u>Hinge</u>

PDVFLFPPKPKDTLMISRTPEVTCVVVDVSHEDPEVKFNWYVDGVEVHNAKTKPREEQYNSTYRVVSVLTVLHQDWLN
<u>CH2</u>

GKEYKCKVSNKALPAPEEKTISKAKGQPREPQVYTLPPSRDELTKNQVSLTCLVKGFYPSDIAVEWESNGQPENNYKTTP
<u>CH3</u>

PVLDSDGSFFLYSKLTVDKSRWQQGNVFSCSVMHEALHNHYTQKSLSLSPGKSGGGGSGGGGSGGGGSGGGGS*NWV*
<u>Linker</u>

*NVISDLKKIEDLIQSMHIDATLYTESDVHPSCKVTAMKCFLLELQVISLESGDASIHDTVENLIILANNSLSSNGNVTESGCK*
<u>IL15mut</u>

*ECEELEEKNIKEFLQSFVHIVQMFINTS*

SEQ ID NO: 39 anti-FLT3 IgG1 (BV10) light chain

DIVMTQSPSSLSVSAGEKVTMSCKSSQSLLNSGNQKNYMAWYQQKPGQPPKLLIYGASTRESGVPDRFTGSGSGTDFTLTISSV
<u>Kro23-VL</u>

QAEDLAVYYCQNDHSYPLTFGAGTKLELKRTVAAPSVFIFPPSDEQLKSGTASVVCLLNNFYPREAKVQWKVDNALQSGNSQES
<u>CL</u>

VTEQDSKDSTYSLSSTLTLSKADYEKHKVYACEVTHQGLSSPVTKSFNRGEC

Fig. 9

SEQ ID NO: 40 Fusion protein of anti-FLT3 IgG1 (4G8) heavy chain with SDIE modifications and IL15 mutant QVQLQQPGAELVKPGASLKLSCKSSGYTFTSYWMHWVRQRPGHGLEWIGEIDPSDSYKDYNQKFKDKATLTVDRSSNT
<u>4G8-VH</u>

AYMHLSSLTSDDSAVYYCARAITTTPFDFWGQGTTLTVSSASTKGPSVFPLAPSSKSTSGGTAALGCLVKDYFPEPVTVS
CH1

WNSGALTSGVHTFPAVLQSSGLYSLSSVVTVPSSSLGTQTYICNVNHKPSNTKVDKKVEPKSCDKTHTCPPCPAPELLGG
Hinge PDVFLFPPKPKDTLMISRTPEVTCVVVDVSHEDPEVKFNWYVDGVEVHNAKTKPREEQYNSTYRVVSVLTVLHQDWLN
CH2

GKEYKCKVSNKALPAPEEKTISKAKGQPREPQVYTLPPSRDELTKNQVSLTCLVKGFYPSDIAVEWESNGQPENNYKTTP
CH3

PVLDSDGSFFLYSKLTVDKSRWQQGNVFSCSVMHEALHNHYTQKSLSLSPGKSGGGGSGGGGSGGGGSGGGGS*NWV*
Linker

*NVISDLKKIEDLIQSMHIDATLYTESDVHPSCKVTAMKCFLLELQVISLESGDASIHDTVENLIILANNSLSSNGNVTESGCK*
IL15mut

*ECEELEEKNIKEFLQSFVHIVQMFINTS*

SEQ ID NO: 41 anti-endoglin IgG1 (4G8) light chain

DIVLTQSPATLSVTPGDSVSLSCRASQSISNNLHWYQQKSHESPRLLIKYASQSISGIPSRFSG
SGSGTDFTLSINSVETED
4G8-VL

FGVYFCQQSNTWPYTFGGGTKLEIKRTVAAPSVFIFPPSDEQLKSGTASVVCLLNNFYPREA
KVQWKVDNALQSGNSQES
CL

VTEQDSKDSTYSLSSTLTLSKADYEKHKVYACEVTHQGLSSPVTKSFNRGEC

Fig. 10A

SEQ ID NO: 42 Fusion protein of anti-PSMA IgG1 (J591) heavy chain with SDIE modifications and IL15 wild type EVQLQQSGPELVKPGTSVRISCKTSGYTFTEYTIHWVKQSHGKSLEWIGNINPNNGGTTYNQKFEDKATLTVDKSSSTJ591-VH AYMELRSLTSEDSAVYYCAAGWNFDYWGQGTTLTVSSASTKGPSVFPLAPSSKSTSGGTAALGCLVKDYFPEPVTVS
                         CH1

WNSGALTSGVHTFPAVLQSSGLYSLSSVVTVPSSSLGTQTYICNVNHKPSNTKVDKKVEPKSCDKTHTCPPCPAPELLGG
                              Hinge PDVFLFPPKPKDTLMISRTPEVTCVVVDVSHEDPEVKFNWYVDGVEVHNAKTKPREEQYNSTYRVVSVLTVLHQDWLN
                         CH2

GKEYKCKVSNKALPAPEEKTISKAKGQPREPQVYTLPPSRDELTKNQVSLTCLVKGFYPSDIAVEWESNGQPENNYKTTP
                            CH3

PVLDSDGSFFLYSKLTVDKSRWQQGNVFSCSVMHEALHNHYTQKSLSLSPGKSGGGGSGGGGSGGGGSGGGGSNWV
                                 Linker NVISDLKKIEDLIQSMHIDATLYTESDVHPSCKVTAMKCFLLELQVISLESGDASIHDTVENLIILANNSLSSNGNVTESGCK
                         IL15mut

ECEELEEKNIKEFLQSFVHIVQMFINTS

SEQ ID NO: 43 Fusion protein of anti-PSMA IgG1 (J591) heavy chain with SDIE modifications and IL15 (E46K) mutant EVQLQQSGPELVKPGTSVRISCKTSGYTFTEYTIHWVKQSHGKSLEWIGNINPNNGGTTYNQKFEDKATLTVDKSSSTJ591-VH AYMELRSLTSEDSAVYYCAAGWNFDYWGQGTTLTVSSASTKGPSVFPLAPSSKSTSGGTAALGCLVKDYFPEPVTVS
                         CH1

WNSGALTSGVHTFPAVLQSSGLYSLSSVVTVPSSSLGTQTYICNVNHKPSNTKVDKKVEPKSCDKTHTCPPCPAPELLGG
                              Hinge PDVFLFPPKPKDTLMISRTPEVTCVVVDVSHEDPEVKFNWYVDGVEVHNAKTKPREEQYNSTYRVVSVLTVLHQDWLN
                         CH2

GKEYKCKVSNKALPAPEEKTISKAKGQPREPQVYTLPPSRDELTKNQVSLTCLVKGFYPSDIAVEWESNGQPENNYKTTP
                            CH3

PVLDSDGSFFLYSKLTVDKSRWQQGNVFSCSVMHEALHNHYTQKSLSLSPGKSGGGGSGGGGSGGGGSGGGGSNWV
                                 Linker NVISDLKKIEDLIQSMHIDATLYTESDVHPSCKVTAMKCFLLKLQVISLESGDASIHDTVENLIILANNSLSSNGNVTESGCK IL15mut

ECEELEEKNIKEFLQSFVHIVQMFINTS

SEQ ID NO: 44 anti-PSMA IgG1 (J591) light chain

NIVMTQSPKSMSMSVGERVTLTCKASENVVTYVSWYQQKPEQSPKLLIYGASNRYTGVPDRFTGSGSATDFTLTISSVQAED

J591 VL

LADYHCGQGYSYPYTFGGGTKLEIKRTVAAPSVFIFPPSDEQLKSGTASVVCLLNNFYPREAKVQWKVDNALQSGNSQES
CL

VTEQDSKDSTYSLSSTLTLSKADYEKHKVYACEVTHQGLSSPVTKSFNRGEC

FUSION PROTEINS COMPRISING A BINDING PROTEIN AND AN INTERLEUKIN-15 POLYPEPTIDE HAVING A REDUCED AFFINITY FOR IL15RA AND THERAPEUTIC USES THEREOF

CROSS-REFERENCES TO RELATED APPLICATIONS

This application is a U.S. national phase application of International PCT Patent Application No. PCT/EP2016/054729, which was filed on Mar. 7, 2016, which claims priority to European Patent Application No. 15157911.7, filed Mar. 6, 2015. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is SCHI_006_01US_SeqList_ST25.txt. The text file is 93 KB, was created on Sep. 6, 2017, and is being submitted electronically via EFS-Web.

BACKGROUND

The present invention relates to fusion proteins comprising a binding protein and an IL-15 polypeptide having a reduced affinity for IL15Rα as well as uses thereof, pharmaceutical compositions comprising such fusion proteins and a method for producing such fusion proteins.

FIELD OF THE INVENTION

Second generation chimeric or humanized monoclonal antibodies, such as Rituxan and Herceptin, have considerably improved treatment of patients with malignant lymphomas and Her2-positive mammary carcinomas, respectively. In general, however, the therapeutic activity of second generation antibodies is limited and there remains an urgent medical need for the development of optimized antibody based reagents (see, for example, Beck A, Wurch T, Bailly C, Corvaia N. Strategies and challenges for the next generation of therapeutic antibodies. Nat Rev Immunol. 2010; 10:345-352).

The capability to recruit Fc-receptor (FcR)-positive immune effector cells, such as NK cells, is considered as being crucial for the therapeutic activity of most antibodies. Thus, many of the strategies used for antibody optimization focus on the improvement of the Fc-part resulting in an enhanced antibody dependent cellular cytotoxicity (ADCC)-activity. In principle this can be achieved by genetic engineering of the glycosylation pattern and/or the amino acid sequence of the CH2 domain of the IgGI-Fc part that is contained in most antitumor antibodies in current clinical use. (Shinkawa T, Nakamura K, Yamane N, et al. (2003) "The absence of fucose but not the presence of galactose or bisecting N-acetylglucosamine of human IgG1 complex-type oligosaccharides shows the critical role of enhancing antibody-dependent cellular cytotoxicity." J Biol Chem. 278:3466-3473; Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I. (2006) "Engineered antibody Fc variants with enhanced effector function." Proc Natl Acad Sci USA 103:4005-4010.

Both strategies have been used by the pharmaceutical industry for the development of Fc optimized third generation antibodies (Oflazoglu E, Audoly L P (2010) "Evolution of anti-CD20 monoclonal antibody therapeutics in oncology." MAbs 2:14-19): Roche (Basel, Switzerland) in cooperation with Glycart (Schlieren, Switzerland) has developed a glyco engineered CD20-antibody GA101 (Obinutuzumab). In a recent large clinical trial with patients suffering from chronic lymphatic leukemia (CLL) this antibody was superior to Rituxan (Goede V et al. (2014) "Obinutuzumab plus Chlorambucil in Patients with CLL and Coexisting Conditions." N Engl J Med 370:1101-1110).

Two other antibodies directed to the lymphoma associated antigens CD19 (XmAb5574) and CD30 (XmAb2513), developed by Xencor (Monrovia, Calif. USA) carry the amino acid exchanges S239D and I332E (SDIE-modification). As GA101, these antibodies were reported to exert markedly enhanced ADCC (Horton et al. (2008) "Potent in vitro and in vivo activity of an Fc-engineered anti-CD19 monoclonal antibody against lymphoma and leukemia." Cancer Res; 68:8049-8057; Foyil K V, Bartlett N L (2010) "Anti-CD30 Antibodies for Hodgkin lymphoma." Curr Hematol Malig Rep 5:140-147) and are currently evaluated in clinical trials.

It is well established that the cytokines IL-2 and IL-15 enhance the cytolytic activity of both natural killer (NK) cells and T cells. Both cytokines use a common βγ-receptor that is completed by a differing α-chain. The differential expression of the α-chain largely determines the biological activity of the cytokines. Both are capable of stimulating NK cells and T cells. However, whereas IL-2 stimulates T-regulatory cells (T regs), IL-15 appears to promote the expansion of e.g. CD8+ memory T cells and inhibit T regs (Ring et al. (2012) "Mechanistic and structural insight into the functional dichotomy between IL-2 and IL-15" Nat Immunol; 13:1187-1195; Waldmann (2006) "The biology of interleukin-2 and interleukin-15: implications for cancer therapy and vaccine design" Nat Rev Immunol; 6:595-601; Perna et al. (2013) "Interleukin 15 provides relief to CTLs from regulatory T cell-mediated inhibition: implications for adoptive T cell-based therapies for lymphoma" Clin Cancer Res; 19:106-117).

Up to now, IL-2 the tumor necrosis factor (TNF), GM-CSF and IL-15 were used for the construction of immunocytokines (Kaspar M, Trachsel E, Neri D (2007) "The antibody-mediated targeted delivery of interleukin-15 and GM-CSF to the tumor neovasculature inhibits tumor growth and metastasis." Cancer Res. 15; 67(10):4940-8). These immunocytokines are fusion proteins of cytokines with antibodies, constructed and intended to allow for a focused cytokine activity. However, upon in vivo application, the proportion of antibody that is specifically bound to a tumor is below 1%. In addition, the activity of a conventional fusion protein does not depend on its specific binding. Consequently, side effects of such fusion proteins exerted by off-target binding to immune cells expressing the respective cytokine receptors are considerable and limit the safely applicable doses. See, for example, List and Neri (2013) "Immunocytokines: a review of molecules in clinical development for cancer therapy". Clin Pharmacol; 5:29-45, Gillies et al. (1992) "Antibody-targeted interleukin 2 stimulates T cell killing of autologous tumor cells", Proc Natl Acad Sci USA; 89:1428-1432, Albertini et al. (2012) "Phase II trial of hu14.18-11.2 for patients with metastatic melanoma". Cancer Immunol Immunother; 61:2261-2271, or Ribas et al.

(2009) "Phase 1/11 open-label study of the biologic effects of the interleukin-2 immunocytokine EMD 273063 (hu14.18-IL2) in patients with metastatic malignant melanoma" J Transl Med; 7:68.

In principle, the particular mechanism of action of IL-15 might provide a solution to this problem: in contrast to IL-2, IL-15 triggers its receptor in trans, that is the α-chain of the receptor, expressed on monocytes and dendritic cells transstimulates the β/γ-receptor on NK- and T cells. Theoretically, this is an optimal situation for the construction of a target cell restricted fusion protein such as an immunocytokine that triggers the βγ-complex of the IL-15 receptor (IL15Rβγ) only after specific binding of the antibody to a target cell. For this purpose, however, the binding of IL-15 to the α-chain of its receptor has to be prevented.

In principle that can be achieved by coupling to binding proteins complexes or fusion proteins of IL-15 and soluble recombinant IL15Rα or fragments thereof (Bessard A et al. (2009) "High antitumor activity of RLI, an interleukin-15 (IL-15)-IL-15 receptor alpha fusion protein, in metastatic melanoma and colorectal cancer." Mol Cancer Ther; 8:2736-2745; Vincent M et al. (2013) "Tumor targeting of the IL-15 superagonist RLI by an anti-GD2 antibody strongly enhances its antitumor potency." Int J Cancer; 133:757-765; Kermer V et al. (2012) "An antibody fusion protein for cancer immunotherapy mimicking IL-15 trans-presentation at the tumor site." Mol Cancer Ther.; 11:1279-1288). Surprisingly, however, fusion proteins or complexes of IL-15 and IL-15RαFc are more effective than the cytokine alone and have been termed IL-15 superagonists. Thus, such proteins cannot be expected to exert target cell restricted activity after coupling to a binding protein that targets this cell.

In line with this reasoning the activity of IL-15 superagonists is not further enhanced by Fc-crosslinking (Rubinstein et al. "Converting IL-15 to a superagonist by binding to soluble IL-15Rα." Proc Natl Acad Sci USA 2006; 103:9166-9171). Thus, it is highly unlikely that the activity of immunocytokines containing such superagonists will be target cell restricted in the sense outlined above.

In summary, there is a still need for the provision of fusion proteins, which can act in a target cell specific manner and/or do not provoke side effects and/or can be administered in safe doses. This problem is solved by the embodiments reflected in the claims, described in the description, and illustrated in the Examples and Figures of the present application.

SUMMARY OF THE INVENTION

The above being said, the present invention relates to a fusion protein comprising
a) a binding protein comprising at least one binding site, wherein the binding site binds to an antigen associated with a target cell; and
b) an IL-15 polypeptide, wherein the IL-15 polypeptide comprises at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO: 1 thereby having a reduced affinity for IL-15Rα compared to the affinity of wild-type IL-15 of SEQ ID NO: 1 (Uniprot number: P40933-1).

In addition, the present invention relates to a fusion protein of the present invention for use in target cell-restricted activation of effector cells expressing IL2/IL-15 R βγ.

Further, the present invention relates to the fusion protein of the present invention for use in target cell-restricted target cell killing mediated by effector cells expressing IL-2/IL-15Rβγ.

The present invention also relates to a fusion protein of the present invention for use in enhancing cytolytic activity of NK cells and T cells, preferably NK cells, gamma delta T cell, NK T cell and CD8+ T cells compared to the cytolytic activity of an unmodified binding protein as described herein.

In addition, the present invention relates to a fusion protein of the present invention for use in the treatment of a disease.

The present invention also relates to a pharmaceutical composition comprising the fusion protein of the present invention.

In addition, the present invention relates to a nucleic acid molecule encoding for the fusion protein of the present invention.

Furthermore, the present invention relates to a host cell comprising the nucleic acid molecule of the present invention or a vector comprising the nucleic acid molecule of the present invention.

In addition, the present invention relates to a method for producing the fusion protein of the present invention, comprising using the nucleic acid encoding the fusion protein for expression of the fusion protein under conditions allowing expression of the fusion protein.

The present invention also relates to a kit comprising the fusion protein of the present invention.

These aspects of the invention will be more fully understood in view of the following description, drawings and non-limiting examples.

BRIEF DESCRIPTION OF THE DRAWINGS

FIG. 1. Target cell restricted stimulation of the IL-15Rβγ-receptor by an exemplary fusion protein of the present invention. A fusion protein of the present invention comprises (i) a binding protein, which, for example, may be an intact dimeric antibody molecule that is directed to a target antigen e.g. on a tumor cell (FIG. 1A). Such a target antigen can, for example, be CD19 or PSMA. The fusion protein of the present invention further comprises (ii) an IL-15 polypeptide that has a reduced affinity for IL-15Rα compared to the affinity of wild-type IL-15 of SEQ ID NO: 1 and/or is no longer capable of binding to the IL-15Rα. Accordingly, such a fusion protein of the invention has two binding specificities, namely a) a target antigen such as CD19 or PSMA and b) IL-15Rβγ. It is however also possible that the binding protein of the inventive protein is a bispecific protein, for example, a bispecific single chain Fv fragment which has one binding site that binds, for example, CD19 and a second binding site that binds, for example, CD3. Such a bispecific fusion protein can be fused, either at its N- or C-terminus with an IL-15 polypeptide that comprises at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO: 1 resulting in a molecule with three binding sites.

Reverting to the example of the inventive fusion protein shown in FIG. 1A that contains as binding molecule an antibody molecule with constant CH2 and CH3 domains. Such a binding protein can further be modified such that it exerts an enhanced antibody dependent cellular cytotoxicity (ADCC) activity compared to its unmodified counterpart. FIG. 1A shows one example of how such a modified binding protein can be obtained, namely by including the so-called SDIE modification of the CH2 domain. This mutation is known to increase ADCC activity of antibody molecules. As mentioned above, in addition to the binding protein part, a fusion protein of the present invention comprises an IL-15 polypeptide that has a reduced or any affinity for IL-15Rα compared to the affinity of wild-type IL-15 of SEQ ID NO: 1. Such an IL-15 polypeptide is also schematically depicted in FIG. 1A. The IL-15 polypeptide can be attached to the binding protein via a (peptidic or non-peptidic) linker. Alternatively, the IL-15 polypeptide can also be fused directly to the binding protein. In addition, in a fusion protein of the invention at least one (i.e. one, two or more, for example, even three) IL-15 polypeptides are fused to the binding protein. In the Example of FIG. 1A, the fusion protein contains two mutated IL-15 polypeptides, each of which is fused to the CH3 domain of the heavy chain of the antibody molecule that is used as binding protein.

Figure 2A:
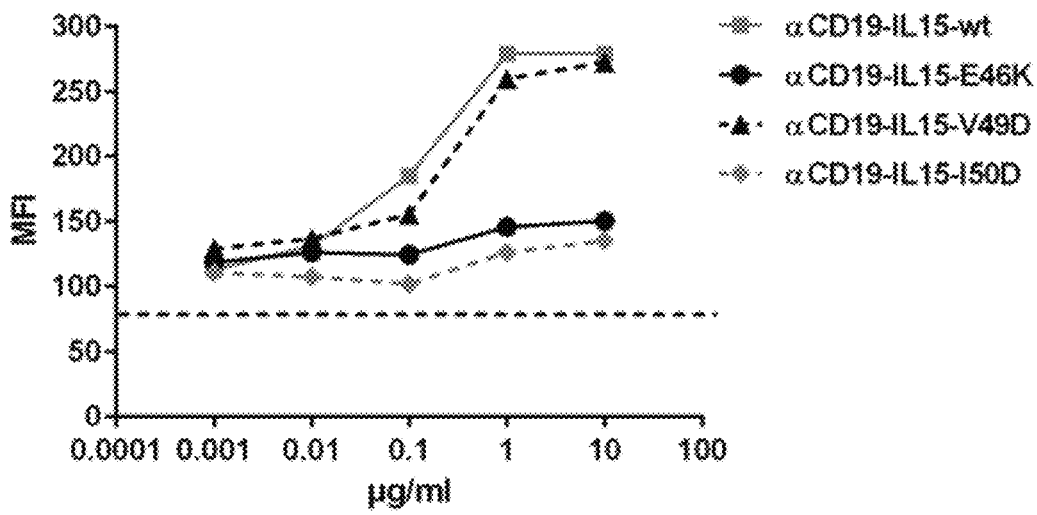

A fusion protein of the present invention allows for a target cell restricted activation of the IL-15-βγ-receptor. The reason for this is the way IL-15 exerts its functions. Under physiological conditions IL-15 binds to two targets, which are expressed on different cells (trans presentation). Firstly, wild type IL-15 binds with high affinity to the IL15Rα receptor that is expressed e.g. on monocytes and dendritic cells. Secondly, IL15Rα then presents the bound IL-15 (in trans) to opposing cells that express the IL-2/IL-15Rβγ. Under physiological conditions the IL-2/IL-15βγ-receptor is expressed on e.g. memory CD8+ T cells, gamma delta T cells, NKT cells or NK cells (FIG. 1B). This means, in the absence of target cells the βγ-receptor cannot be activated by the inventive fusion proteins, since trans presentation by the α-chain cannot occur (FIG. 1C).

FIG. 1B and FIG. 1C exemplarily depict the functioning of a fusion protein of the present invention. The binding protein binds to a target cell. With its IL-15 polypeptide part, a fusion protein of the present invention is then able to simultaneously bind to βγ-receptor-positive cells such a CD8+ T cells or NK cells (see above) and activate these cells. This mimics the presentation of IL-15 via the IL-5Rα. This is because trans-presentation of IL-15 to the βγ-complex of its receptor is achieved by the target cell rather than a cell expressing the a-part of the IL-15 receptor. The endogenous affinity to IL-15Rα is reduced in the fusion proteins of the present invention. Thus, if no target cell is present IL-15Rα mediated presentation does not occur and consequently βγ-receptor-positive effector cells are not activated.

FIG. 2. Binding to IL-15Rα (A) and cytolytic activity of various fusion proteins (B) comprising different IL-15 polypeptides. (A): CD19-positive NALM16 cells were incubated with the indicated concentrations of distinct fusion proteins, stained with a recombinant, His-tagged IL-15R-α-Fc-fusion protein, a Biotin-labeled anti-His antibody and finally with a streptavidin PE-conjugate. Cells were then analyzed by flow cytometry.

In particular, the fusion protein αCD19-IL15wt (wt=wild-type) comprised the CD19 antibody 4G7 with an Fc optimized human IgG1 constant region (SDIE mutation as described herein) fused to wild-type human IL-15 (hIL-15), wherein the hIL-15 is directly linked to the CH3 domain via a two amino acid linker, namely a Glycine-Serine linker (also referred herein as "short linker"). This fusion protein served as a control. Further tested fusion proteins named αCD19-IL15-E46K, αCD19-IL15-V49D or αCD19-IL15-I50D comprised the 4G7 antibody with an Fc optimized (SDIE) human IgG1 constant region (SDIE mutation as described herein). The IL-15 polypeptide was mutated at the indicated positions. These positions correspond to the indicated positions in SEQ ID NO: 2 and SEQ ID NO: 4, as shown in FIG. 5A. These amino acid positions furthermore correspond to amino acid substitutions E94K (for E46K), V97D (for V49D) and I98D (for I50D) with regard to SEQ ID NO: 1 (also described herein in more detail). In all these fusion proteins the hIL-15 is directly linked to the CH3 domain via the two amino acid glycine-serine linker.

To analyze whether the IL-15 polypeptides comprising the different amino acid substitutions remained their ability to bind to IL-15 Rα a His-tagged IL-15R-α-Fc-fusion protein (R&D systems) was added to the cultures. Thus, if the IL-15 polypeptide part of the fusion proteins remained its ability to bind to IL-15Rα the added His-tagged IL-15R-α-Fc-fusion protein will bind (via the fusion protein) to the NALM 16 cells. Thus, upon addition of a Biotin-labeled anti-His antibody (Qiagen) and a streptavidin PE-conjugate (Life technologies) a detectable signal will be generated. This signal was measured by flow cytometry (mean Fluorescence Intensity; MFI); y-axis of FIG. 2A).

FIG. 2A shows that the MFI detected for the αCD19-IL15-wt (4G7-IL15-wt; wt=wild-type) fusion protein (control) is around 300 MFI. Since IL-15 normally binds to ILR-15α this signal provides evidence for a binding of IL-15 to IL-15Rα. The αCD19-IL15-V49D (4G7-IL15-V49D) fusion protein exhibited a similar signal when compared to the control thereby indicating that this fusion protein binds to ILRα albeit with a slightly lower affinity. The fusion proteins αCD19-IL15-E46K (4G7-IL15-E46K) and αCD19-IL15-I50D (4G7-IL15-I50D) showed a MFI signal of around 150, indicating that the binding to IL-15Rα is strongly diminished (or even absent). The dashed line in FIG. 2 A indicates background staining, that is, staining of cells by the labeled detection antibodies (without IL15 containing fusion proteins). Thus, the IL-15 polypeptides comprising amino acid substitutions E46K and I50D showed a strongly diminished/or were even devoid of ILR-15α-binding if used within a fusion protein comprising a binding protein (FIG. 2A).

Figure 2B:
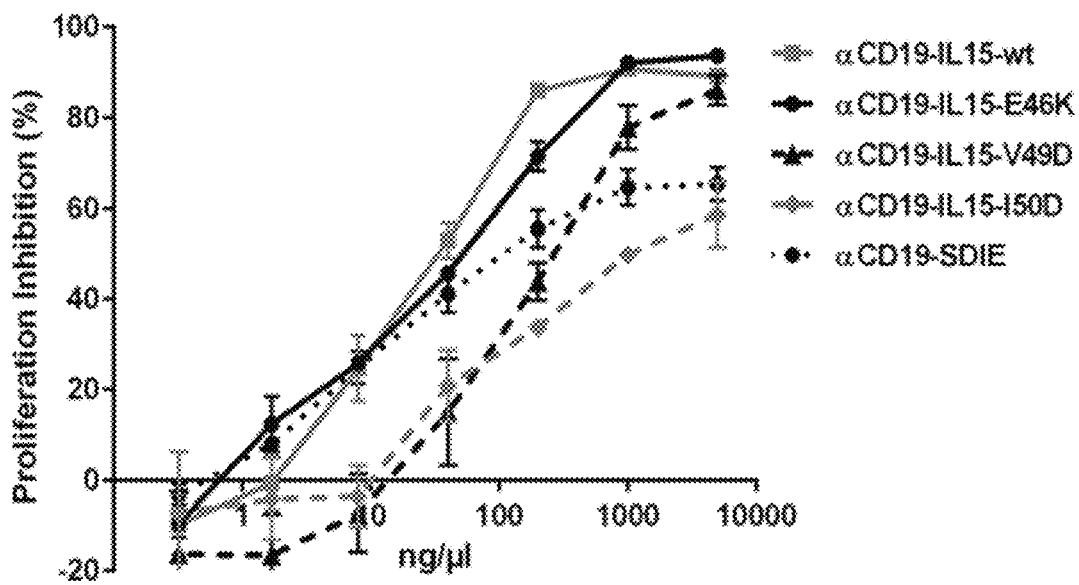

In FIG. 2B, NALM16 cells were incubated with the respective fusion proteins also used for the experiments shown in FIG. 2A and the peripheral blood mononuclear cells (PBMC) of a healthy volunteer. After 2 days, proliferation was assessed using a $^3$H-thymidine uptake assay. Proliferation in the absence of fusion proteins and PBMC was defined as 100% proliferation that is 0% inhibition of proliferation.

Usually such PBMC cells comprise lymphocytes, monocytes and macrophages. Some of the lymphocytes, in particular NK cells, express Fcγ-receptors as well as the β and common γ chain of the IL-2/IL-15 receptor to which IL-15 can bind (see above). Thus, upon binding of the fusion protein(s) to both, the NALM16 cells via the CD19 binding protein (4G7: CD19-specific antibody) and the NK cells via IL15, the NALM16 cells can be killed. Binding of IL-15 to the IL-15Rβγ-activates NK cells and enhances antibody mediated killing. With the experiments depicted in FIG. 2A the cytolytic activity of the distinct fusion proteins was analyzed.

As can be seen in FIG. 2B, the αCD19-IL15-wt (4G7-IL15-wt, wherein 4G7 is an Fc-optimized 4G7 antibody carrying the SDIE-modification) and the αCD19-IL15-E46K (4G7-IL15-E46K, wherein 4G7 is an Fc-optimized 4G7 antibody carrying the SDIE-modification) fusion proteins both yielded an inhibition of about 80-85%. The αCD19-IL15-V49D (4G7-IL15-V49D, wherein 4G7 is an Fc-optimized 4G7 antibody carrying the SDIE-modification) protein reached a similar level, however, it was less effective at lower concentrations. The αCD19-IL15-I50D (4G7-IL15-I50D, wherein 4G7 is a Fc-optimized 4G7 antibody carrying the SDIE-modification) fusion protein and the unmodified αCD19-SDIE (4G7-SDIE) antibody without a fused IL-15 protein resulted in an inhibition of about 60% of the proliferation. Thus, from the group of fusion proteins with a mutated IL-15, the fusion protein containing the E46K amino acid substitution in the IL-15 polypeptide showed the highest cytolytic activity against CD19 expressing target cells and was thus used in subsequent experiments.

Conclusions from the data presented in FIG. 2: Two of the three mutated IL-15 polypeptides evaluated, E46K and I50D, were devoid of ILR-15Rα-binding if used within a CD19-targeting fusion protein (A). The fusion protein containing the E46K amino acid substitution had the highest cytolytic activity against CD19 expressing target cells (B).

Figure 3A:
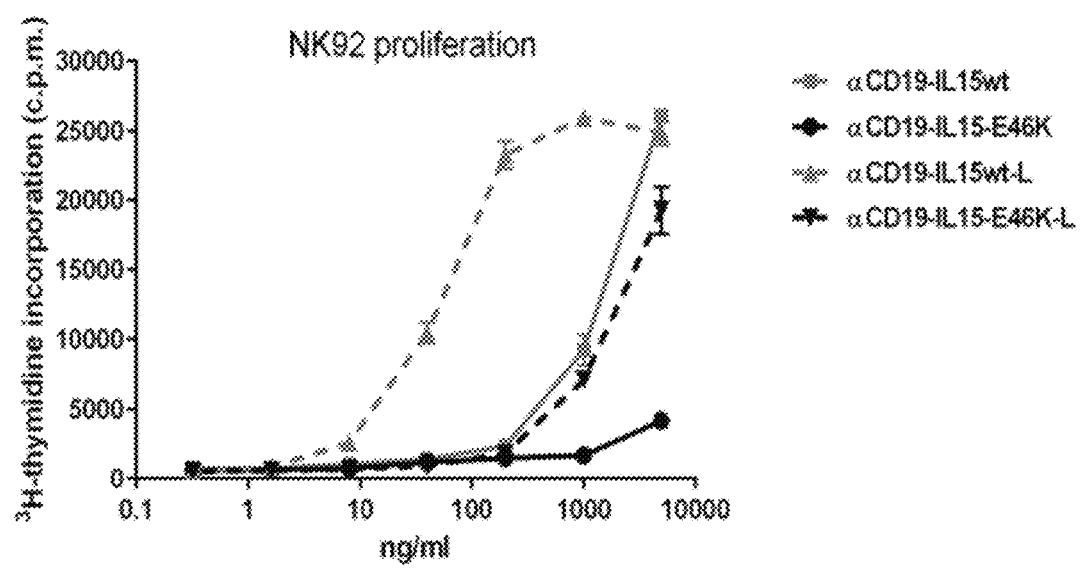
Figure 3B:
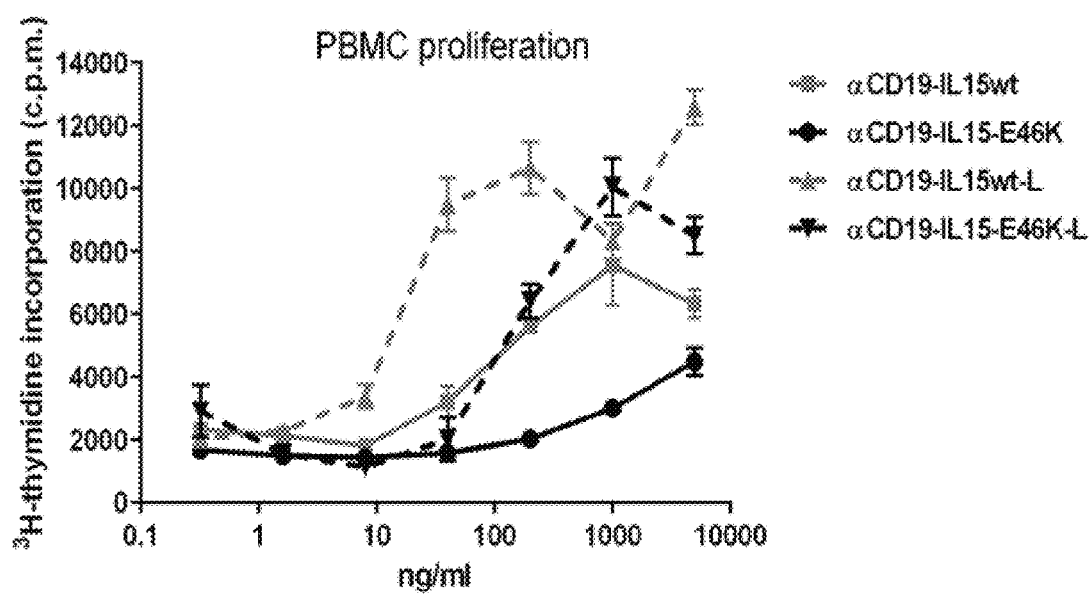

FIG. 3. Proliferation induced by different fusion proteins in NK92 cells (FIG. 3A) and PBMC (FIG. 3B). While the experiments depicted in FIG. 2 were performed with fusion proteins containing a short linker the experiments presented in FIG. 3 made additional use of fusion proteins containing a long linker (L). The fusion proteins with the long linker comprise a 20 amino acid long amino acid stretch (4-glycine 1-serine)$_4$. In fusion proteins comprising the short linker hIL-15 is directly linked to the CH3 domain via the short glycine-serine linker. Fusion proteins containing the long or the short linker were incubated with NK92 cells (FIG. 3A) or PBMC (FIG. 3B) cells for two days. Then, cells were pulsed with $^3$H thymidine, harvested at day 3 on filter mats and counted in a liquid scintillation counter.

In FIG. 3A, NK92 cells were incubated with different concentrations of the distinct fusion proteins as indicated (x-axis and figure legend in FIG. 3A). NK92 cells are natural killer lymphoma cells, which do not express CD19 to which the αCD19 binding protein binds (Gong et al. (1994) "Characterization of a human cell line (NK-92) with phenotypical and functional characteristics of activated natural killer cells" Leukemia; 8(4):652-8). Thus, this cell culture is devoid of target cells. By measuring proliferation via $^3$H-thymidine counts as depicted on the y-axis (FIG. 3A), the ability of the fusion proteins to induce proliferation in effector cells in general is assessed.

The αCD19-IL15-wt (4G7-IL15wt; containing the short linker, wherein 4G7 is an Fc-optimized 4G7 antibody carrying the SDIE-modification) and αCD19-IL15-wt-L (4G7-IL15wt-L; containing the long linker, wherein 4G7 is a Fc-optimized 4G7 antibody carrying the SDIE-modification) resulted in a $^3$H thymidine count of about 25000. However, the protein with the long linker has been considerably more active at lower concentration indicating that the short linker affects IL-15 activity. Likewise, the fusion proteins containing the IL-15 polypeptide of the fusion proteins of the present invention have been less active than those containing the wild-type IL-15 protein. Thus, the E46K mutation diminishes IL-15 activity as expected since these fusion proteins cannot be presented by IL-15Rα. In addition, IL-15 activity is further diminished by fusion via a short linker.

Similar results were also obtained in the experiments depicted in FIG. 3B. Here, PBMC cells were incubated with different concentrations of the distinct fusion proteins as indicated (x-axis and figure legend in FIG. 3B). Some PBMCs (such as B cells) also express CD19, which is detected by the αCD19 (here 4G7) binding protein. Notably, a PBMC culture also comprises some potential effector cells such as e.g. NK cells. As in FIG. 3A, the proliferation was determined by $^3$H-thymidine counts as depicted on the y-axis (FIG. 3B).

In these experiments, the αCD19-IL15-wt (4G7-IL15wt; short linker) and αCD19-IL15-wt-L (4G7-IL15wt-L; containing the long linker and wild-type (wt) IL-15) resulted in a $^3$H thymidine count of about 6000 and 12000, respectively. Again, the αCD19-IL15-E46K (4G7-IL15-E46K, wherein 4G7 is a Fc-optimized 4G7 antibody carrying the SDIE-modification) provided for a lesser extend of proliferation (about 4500 counts of $^3$H thymidine), while the fusion-protein αCD19-IL15-E46K-L (4G7-IL15-E46K-L; containing the long linker, wherein 4G7 is a Fc-optimized 4G7 antibody carrying the SDIE-modification) resulted in a detected proliferation similar to the IL-15 wild-type fusion proteins (about 8500 counts; FIG. 3B). Thus, in this experiment, the αCD19-IL15-E46K-L (4G7-IL15-E46K-L) induced a higher proliferation/activation of cells than the αCD19-IL15-E46K (4G7-IL15-E46K) fusion protein confirming the results obtained with the NK92 cells.

Conclusions from the data presented in FIG. 3: (i) The fusion protein with the IL-15 comprising the amino acid substitution E46K is less active than the fusion protein comprising wild-type IL-15 and (ii) the fusion protein with a long linker (L) are more active than those with a short linker. Thus, fusion proteins containing the long linker were used in the subsequent experiments.

Figure 4A:
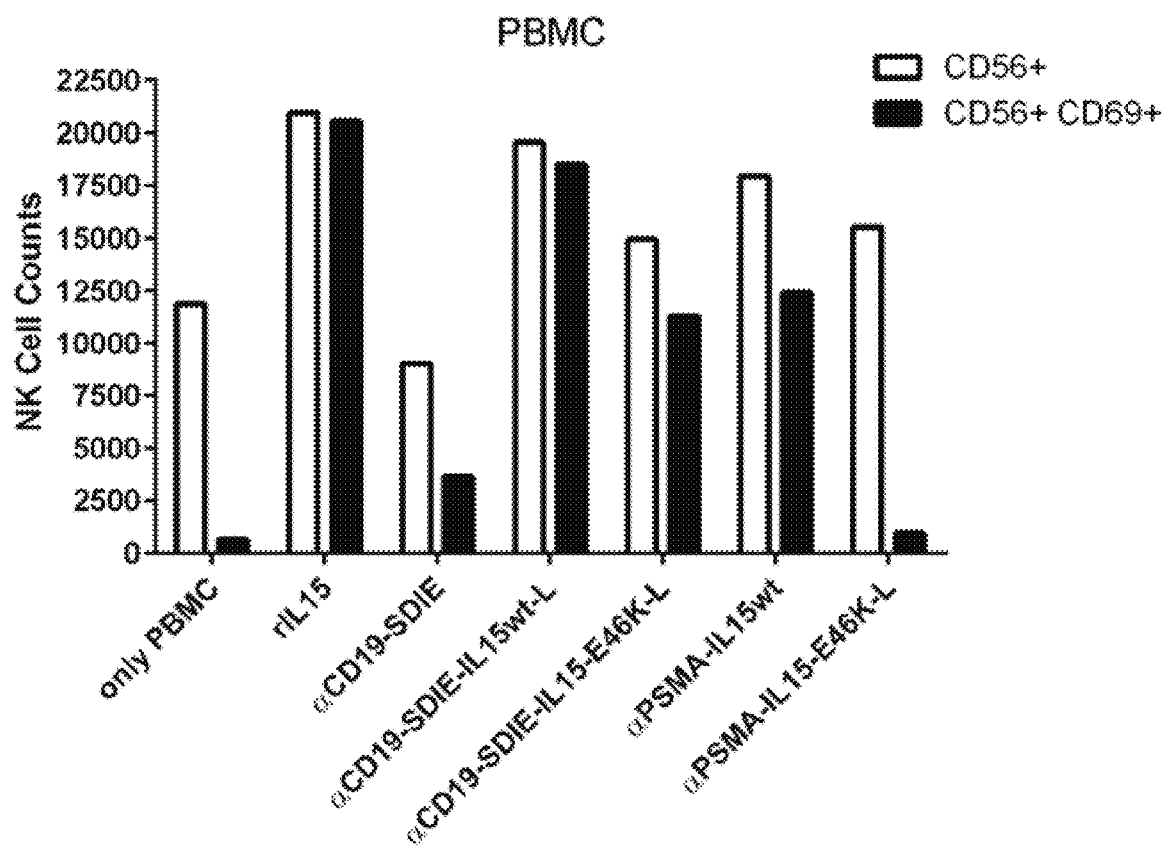
Figure 4B:
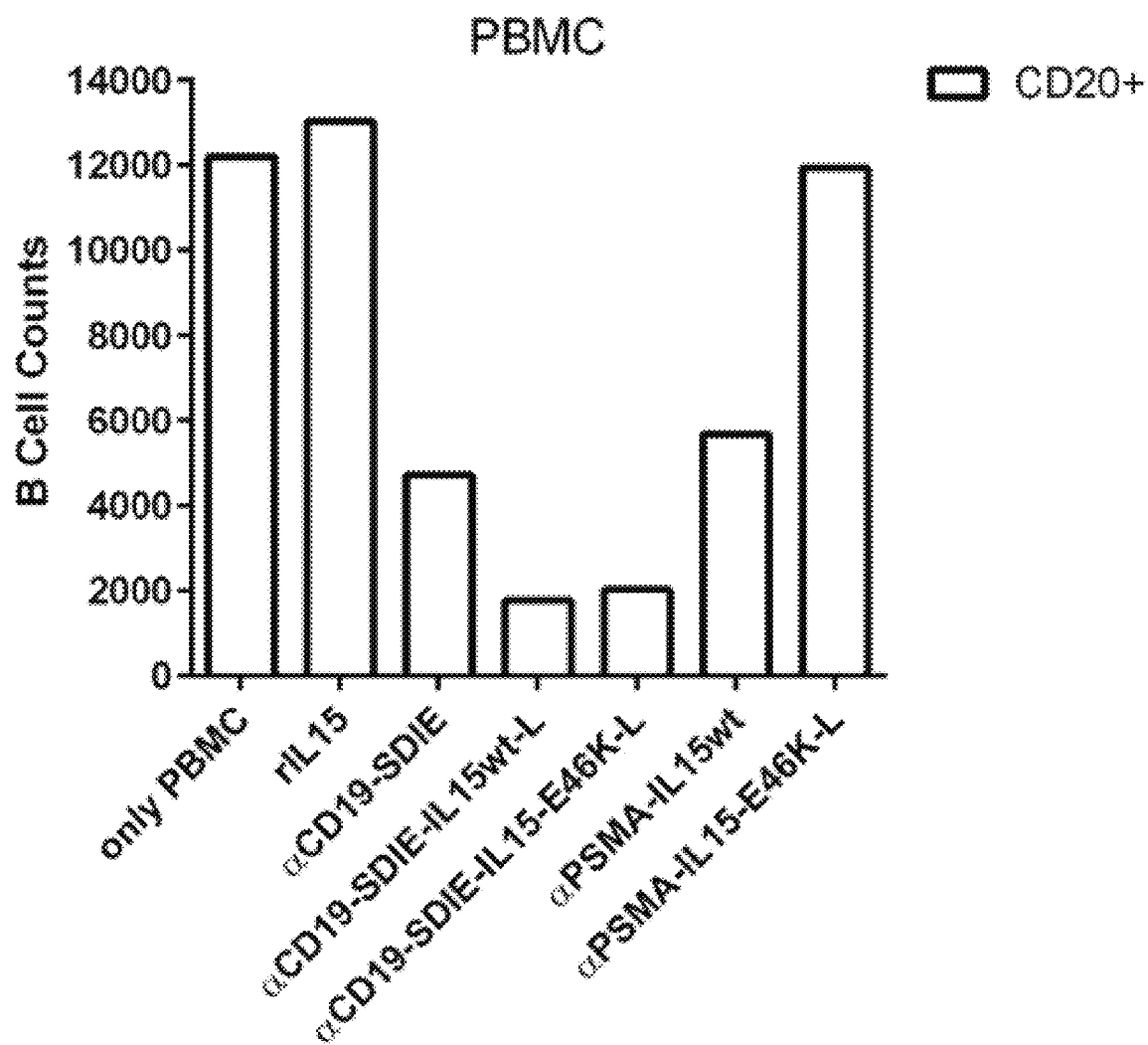

FIG. 4. Target cell restricted NK cell activation (FIG. 4A) and B cell killing (FIG. 4B) in PBMC cultures by different fusion proteins. To evaluate target cell restriction of the generated fusion proteins, normal PBMC were incubated with wild-type IL-15 and IL-15 polypeptides having a reduced affinity for IL-15Rα than wild-type IL-15 comprised in different fusion proteins targeting the B cell associated CD19 antigen and the prostate specific membrane antigen (PSMA), respectively. Since B cells are present within PBMC cultures, CD19 serves as a relevant target antigen in this setting, whereas PSMA is absent and thus irrelevant. PBMC were incubated for three days with the indicated fusion proteins (0.1 µg/ml) and were then analyzed by flow cytometry.

In FIG. 4A NK cell activation and B cell killing was assessed by measuring the numbers of CD56-positive cells expressing CD69 (CD56+/CD69+ double positive cells). CD69 is expressed by activated NK cells, while CD56 is expressed by resting NK cells as well. By selecting double positive cells (CD56+/CD69+), only activated NK cells are measured.

In FIG. 4A, cell counts are provided on the y-axis and the different fusion proteins utilized are depicted on the x-axis. In the control PBMC culture ("only PBMC") about 12000 cells expressed CD56 (CD56+) and about 1000 were double-positive for CD56 and CD69 (CD56+/CD69+). Application of the 4G7 binding protein targeting CD19 and comprising the SDIE mutations (αCD19-SDIE) slightly increased the number of activated NK cells (αCD19-SDIE: Fc-optimized 4G7 antibody carrying the SDIE-modification, without IL-15 polypeptide attached thereto). On the contrary, the number of activated NK cells within PBMC cultures massively increased as a result of the addition of the αCD19-SDIE-IL15wt-L fusion protein (4G7-IL15wt-L, containing the long linker, wherein 4G7 is a Fc-optimized 4G7 antibody carrying the SDIE-modification). A less prominent but still remarkable increase in the number of activated NK cells was also observed with the αCD19-SDIE-IL15-E46K-L fusion protein (4G7-IL15-E46K-L, containing the long linker, wherein 4G7 is a Fc-optimized 4G7 antibody carrying the SDIE-modification).

Additional experiments were conducted with fusion proteins targeting PSMA, which is not expressed by PBMC cells. Here, the addition of the αPSMA-IL15-E46K-L fusion protein (containing the long linker) did not significantly alter the composition of the cells. On the contrary, the application of the αPSMA-IL15wt fusion protein (containing the long linker) significantly increased the number of activated NK cells within the CD56-positive cell pool.

From these results it can be concluded that NK cell activation by the fusion proteins containing an IL-15 polypeptide of the present invention is target cell restricted, that is the binding protein targeting CD19, but not that targeting PSMA activates NK cells and kills B cells. Upon application of fusion proteins comprising wild-type IL-15 target cell restricted activation of NK cell is clearly less prominent. This is because wild type IL-15 is trans-presented by IL-15Rα and does not require binding of the fusion protein to target cells.

In FIG. 4B NK cell activation and B cell killing was assessed by measuring the numbers of CD20+ B cells. CD20 is exclusively expressed by B cells. In this experiment, a cell culture containing only PBMC cells without the addition of any fusion proteins served as a control. Here about 12000 CD20-positive (CD20+) B cells were counted. The addition of the αCD19-SDIE control resulted in a decrease of CD20-positive B cells (to about 4000 cells). Notably, the αCD19-SDIE-IL15wt-L (comprising the long linker) and αCD19-SDIE-IL-15E46K-L (comprising the long linker) fusion proteins resulted in the greatest decrease in CD20-positive B cells (about 2000 cells). On the contrary, the addition of a PSMA-IL-15wt fusion protein showed a decrease to about 6000 cells. Notably, the PSMA-IL-15-E46K-L fusion protein did not alter the number of CD20-positive B-cells in comparison to the "only PBMC" control.

Thus, the reduction of the number of CD20+ cells (B cell depletion) by the binding protein-IL-15 polypeptide fusion proteins was more pronounced than that by the Fc-optimized CD19 antibody (αCD19SDIE) alone (FIG. 4B). Furthermore, the PSMA directed fusion proteins showed that the IL-15-E46K-L fusion protein did not show any effect on the CD20-positive B cells. Thus, the target cell restricted B cell killing is most prominent using the IL-15-E46K-L fusion proteins, while fusion proteins comprising IL-15 wild-type showed a less prominent or even absent target cell restricted killing of B cells (FIG. 4B).

Figure 4C:
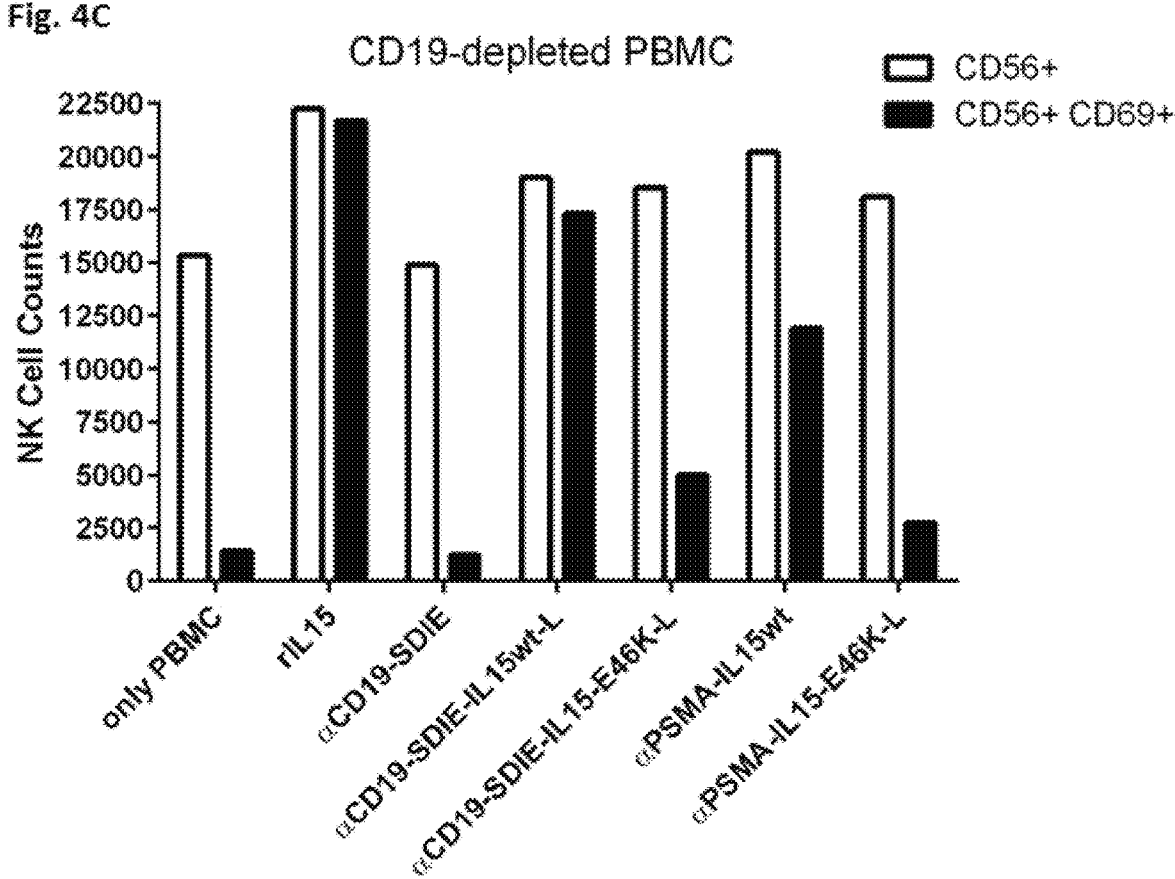

In FIG. 4C NK-cell activation was assessed in B-cell depleted PBMC cultures. B cells were depleted with magnetic-activated cell sorting (MACS) using CD19 Micro-Beads (Miltenyi Biotec). As in FIGS. 4A and 4B, for determination of cell numbers an equal amount of BD negative beads (negative beads from BD Biosciences) was added to each sample. During flow cytometry measurement the same number of BD negative beads were acquired for all samples. This allowed the quantification of cells and direct comparison of cell numbers between different samples from one experiment. These experiments demonstrated that NK cell activation is markedly reduced in the presence of the fusion protein containing the E46K mutated IL-15 polypeptide almost reaching the level of the corresponding protein targeting PSMA. This is because cells carrying the target antigen CD19 had been depleted. The activity of fusion proteins containing wild type IL-15 was hardly affected.

Conclusions from the data presented in FIG. 4:
a. NK cell activation by the fusion proteins containing an IL-15 polypeptide of the present invention is target cell restricted, that is the protein targeting CD19 but not that targeting PSMA activates NK cells and kills B cells. NK cell activation by the CD19 targeting fusion proteins comprising mutated IL-15 polypeptides was diminished if B cells were depleted from the PBMC (FIG. 4C)
b. NK cell activation by both fusion proteins containing wild-type IL-15 is not target cell restricted, that is both fusion proteins induce NK cell activation and at least some killing of B cells irrespective of the antigen targeted.
c. B cell depletion by the inventive fusion proteins is more pronounced than that by the Fc-optimized CD19 antibody (4G7SDIE) alone (FIG. 4B).

FIG. 5A and 5B. Depiction of different sequences. The sequence of wild-type hIL-15 is depicted in SEQ ID NO: 1(FIG. 5A). The first 48 amino acids of this sequence that is underlined comprise the long 48 amino acid signal peptide, which is cleaved during secretion of hIL-15 and is not part of the IL-15 fusion proteins. In SEQ ID NO: 1 the corresponding amino acids, which are important for binding of wild-type IL-15 to the IL-15Rα (shown in SEQ ID NO: 2, 3 and SEQ ID NO: 4, as depicted in FIG. 5A) are highlighted in grey. Also highlighted in grey in SEQ ID NO: 1 are amino acids important for βγ-receptor binding as described in Ring et al. (2012) (Ring et al. (2012) "Mechanistic and structural insight into the functional dichotomy between IL-2 and IL-15" Nat Immunol; 13:1187-1195). In particular, amino acids important for βγ receptor binding are the amino acids corresponding to amino acid positions 55, 56, 58, 59, 109, 113, 116, 117, 156, 157, 160 of SEQ ID NO: 1. The amino acid positions important for IL15Rα or βγ-receptor binding are also depicted in Tables 1 and 2 below.

Also depicted in FIG. 5A are amino acid sequences of single heavy chain variable domain of anti-CD19 antibody 4G7 (SEQ ID NO: 5), single light chain variable domain of anti-CD19 antibody 4G7 (SEQ ID NO: 6), single heavy chain variable domain of anti-FLT3 antibody BV10 (SEQ ID NO: 7), single light chain variable domain of anti-FLT3 antibody BV10 (SEQ ID NO: 8), single heavy chain variable domain of anti-FLT3 antibody 4G8 (SEQ ID NO: 9). Depicted in FIG. 5B are amino acid sequences of single light chain variable domain of anti-FLT3 antibody 4G8 (SEQ ID NO: 10), single heavy chain variable domain of anti-PSMA antibody J591 (SEQ ID NO: 11), single light chain variable domain of anti-PSMA antibody J591 (SEQ ID NO: 12), single heavy chain variable domain of anti-endoglin antibody Kro23 (SEQ ID NO: 25), single light chain variable domain of anti-endoglin antibody Kro23 (SEQ ID NO: 26). CDR sequences are underlined.

FIG. 6. Depiction of a fusion protein of anti-endoglin IgG1 (Kro23) heavy chain comprising SDIE modification and an IL15 mutant (SEQ ID NO: 27), as well the light chain of anti-endoglin IgG1 (Kro23) (SEQ ID NO: 28). In the depiction of SEQ ID NO: 27, the VH region is highlighted in grey, where the CDRs are underlined, followed by the CH1 region without highlights. The hinge region is again highlighted in grey and represented by italic letters, whereas the following CH2 region is again not highlighted. The subsequent CH3 region is highlighted in grey and represented by bold letters, followed by a linker sequence, which is not highlighted. The final part is the IL15 mutant (IL15mut), which is again highlighted in grey and represented by bold italic letters, and wherein the mutated amino acid of the IL15 mutant is underlined. This mutation corresponds to an E46K mutation of SEQ ID NO: 4. In SEQ ID NO: 26, the VL region is highlighted in grey, where the CDRs are underlined, whereas the CL region is not highlighted.

FIG. 7. Depiction of a fusion proteins FIG. 7A depics a fusion protein of anti-CD19 IgG1 (4G7) heavy chain comprising SDIE modification and an IL15 wild type with glycine-serine linker (short linker) (SEQ ID NO: 29), a fusion protein of anti-CD19 IgG1 (4G7) heavy chain comprising SDIE modification and an IL15 E46K mutant with short linker (SEQ ID NO: 30. FIG. 7B depicts a fusion protein of anti-CD19 IgG1 (4G7) heavy chain comprising SDIE modification and an IL15 V49D mutant with short linker (SEQ ID NO: 31), a fusion protein of anti-CD19 IgG1 (4G7) heavy chain comprising SDIE modification and an IL15 I50D mutant with short linker (SEQ ID NO: 32). FIG. 7C depicts a fusion protein of anti-CD19 IgG1 (4G7) heavy chain comprising SDIE modification and an IL15 wild type with (glycine$_4$-serine$_1$)$_4$ linker (long linker) (SEQ ID NO: 33), a fusion protein of anti-CD19 IgG1 (4G7) heavy chain comprising SDIE modification and an IL15 E46K mutant with long linker (SEQ ID NO: 34), FIG. 7D depicts a fusion protein of anti-CD19 IgG1 (4G7) heavy chain comprising SDIE modification and an IL15 V49D mutant with long linker (SEQ ID NO: 35). FIG. 7E depicts a fusion protein of anti-CD19 IgG1 (4G7) heavy chain comprising SDIE modification and an IL15 I50D mutant with long linker (SEQ ID NO: 36), as well the light chain of anti-CD19 IgG1 (4G7) (SEQ ID NO: 37). In the depiction of SEQ ID NOs: 30-37(FIG. 7A-FIG. 7E), the VH region is highlighted in grey, where the CDRs are underlined, followed by the CH1 region without highlights. The hinge region is again highlighted in grey and represented by italic letters, whereas the following CH2 region is again not highlighted. The subsequent CH3 region is highlighted in grey and represented by bold letters, followed by a linker sequence, which is not highlighted. The final part is the IL15 mutant (IL15mut), which is again highlighted in grey and represented by bold italic letters, and wherein the mutated amino acid is underlined in the fusion proteins comprising IL-15 mutants. These mutation corresponds to an E46K (SEQ ID NOs: 30 and 34), V49D (SEQ ID NOs: 31 and 35), or I50D (SEQ ID NOs: 32 and 36) mutation of SEQ ID NO: 4, respectively. In SEQ ID NO: 37, the VL region is highlighted in grey, where the CDRs are underlined, whereas the CL region is not highlighted.

FIG. 8. Depiction of a fusion protein of anti-FLT3 IgG1 (BV10) heavy chain comprising SDIE modification and an IL15 mutant (SEQ ID NO: 38), as well the light chain of anti-FLT3 IgG1 (BV10) (SEQ ID NO: 39). In the depiction of SEQ ID NO: 38, the VH region is highlighted in grey, where the CDRs are underlined, followed by the CH1 region without highlights. The hinge region is again highlighted in grey and represented by italic letters, whereas the following CH2 region is again not highlighted. The subsequent CH3 region is highlighted in grey and represented by bold letters, followed by a linker sequence, which is not highlighted. The final part is the IL15 mutant (IL15mut), which is again highlighted in grey and represented by bold italic letters, and wherein the mutated amino acid of the IL15 mutant is underlined. This mutation corresponds to an E46K mutation of SEQ ID NO: 4. In SEQ ID NO: 39, the VL region is highlighted in grey, where the CDRs are underlined, whereas the CL region is not highlighted.

FIG. 9. Depiction of a fusion protein of anti-FLT3 IgG1 (4G8) heavy chain comprising SDIE modification and an IL15 mutant (SEQ ID NO: 40), as well the light chain of anti-FLT3 IgG1 (4G8) (SEQ ID NO: 41). In the depiction of SEQ ID NO: 40, the VH region is highlighted in grey, where the CDRs are underlined, followed by the CH1 region without highlights. The hinge region is again highlighted in grey and represented by italic letters, whereas the following CH2 region is again not highlighted. The subsequent CH3 region is highlighted in grey and represented by bold letters, followed by a linker sequence, which is not highlighted. The final part is the IL15 mutant (IL15mut), which is again highlighted in grey and represented by bold italic letters, and wherein the mutated amino acid of the IL15 mutant is underlined. This mutation corresponds to an E46K mutation of SEQ ID NO: 4. In SEQ ID NO: 41, the VL region is highlighted in grey, where the CDRs are underlined, whereas the CL region is not highlighted.

Figure 10B:

FIG. 10. Depiction of a fusion proteinS FIG. 10A depicts a fusion protein of anti-PSMA IgG1 (J591) heavy chain comprising SDIE modification and an IL15 wild type (SEQ ID NO: 42), a fusion protein of anti-PSMA IgG1 (J591) heavy chain comprising SDIE modification and an IL15 E46K mutant (SEQ ID NO: 43). FIG. 10B depics the light chain of anti-PSMA IgG1 (J591) (SEQ ID NO: 44). In the depiction of SEQ ID NOs: 42 and 43(FIG. 10A and FIG. 10B), the VH region is highlighted in grey, where the CDRs are underlined, followed by the CH1 region without highlights. The hinge region is again highlighted in grey and represented by italic letters, whereas the following CH2 region is again not highlighted. The subsequent CH3 region is highlighted in grey and represented by bold letters, followed by a linker sequence, which is not highlighted. The final part is the IL15 mutant (IL15mut), which is again highlighted in grey and represented by bold italic letters, and wherein the mutated amino acid is underlined in the fusion protein comprising the IL-15 mutant. These mutation corresponds to an E46K (SEQ ID NO: 43) mutation of SEQ ID NO: 4. In SEQ ID NO: 44, the VL region is highlighted in grey, where the CDRs are underlined, whereas the CL region is not highlighted.

TABLE 1

Sequences important for IL-15Rα binding

| | |
|---|---|
| Amino acid positions with regard to SEQ ID NO: 1 | 92, 93, 94, 95, 96, 97, 98, 99, 100, 112, 113, 114, 115, 116 |
| Amino acid positions with regard to SEQ ID NO: 4 | 44, 45, 46, 47, 48, 49, 50, 51, 52, 64, 65, 66, 67, 68 |

TABLE 2

Sequences important for IL-15Rβγ binding

| | |
|---|---|
| Amino acid positions with regard to SEQ ID NO: 1 | 55, 56, 58, 59, 109, 113, 116, 117, (β-chain binding) 156, 157, 160 (γ-chain binding) |
| Amino acid positions with regard to SEQ ID NO: 4 | 7, 8, 10, 11, 61, 65, 68, 69 (β-binding), 108, 109, 112 (γ-binding) |

The amino acid sequence of SEQ ID NO: 4 is a fragment of SEQ ID NO: 1, in which the amino acid positions important for IL-15Rα and IL-2/IL-15Rβγ binding are highlighted as well in FIG. 5A.

DETAILED DESCRIPTION

The present application provides fusion proteins that are capable of target cell restricted killing (of these target cells), wherein these fusion proteins contain two "different functional parts", namely as a first part a binding protein (as described in detail herein) and, as a second part, an IL-15 polypeptide, preferably a human IL-15 polypeptide that has a reduced affinity for IL-15Rα, preferably reduced affinity for the human"IL-15Rα compared to the affinity of wild-type IL-15 of SEQ ID NO: 1 (UniProt accession number: P40933). The inventors have found that such an IL-15 polypeptide comprises at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO: 1. It is noted in this context that the term "IL-15Rα" is used in its regular meaning to refer to the Interleukin 15 receptor, alpha subunit, that means the subunit of the Interleukin 15 receptor that binds IL-15 with high affinity and independently of the two other subunits of the IL-15 receptor, CD122 and CD132 (which the IL-15 receptor shares with the receptor for IL-2). The amino acid sequence of "IL-15Rα" is known for many species, the sequence of the human "IL-15Rα" has been deposited under the UniProt accession number Q13261.

Also the term "IL-15" or "IL15" is used in its regular meaning to refer to the Interleukin 15. The amino acid sequence of "IL-15" is known for many species, the sequence of the human "IL-15" has been deposited as Isoform IL15-S48AA under the UniProt accession number P40933 and GeneBank Accession number DQ893709, respectively and is depicted in SEQ ID NO: 1).

In principle in fusion proteins comprising such a IL-15 polypeptide the target binding protein replaces the function of the α-chain of the IL-15 receptor, thereby resulting in a target cell restricted stimulation of the βγ-chain that is depending on the binding of the binding protein to its target antigen, expressed e.g. on a tumor cell. Thus, off-target effects are reduced and application of higher doses, capable of achieving e.g. sufficient NK and T cell activation in vivo is possible. Once activated, e.g. NK cells can be effectively recruited by e.g. an Fc optimized targeting binding protein comprised in a fusion protein of the present invention (FIG. 1).

The fusion proteins of the present invention are an advantageous alternative over known complexes or fusion proteins of IL-15 and soluble recombinant IL-15Rα or fragments thereof. See in this respect, e.g. Bessard et al. (2009) "High antitumor activity of RLI, an interleukin-15 (IL-15)-IL-15 receptor alpha fusion protein, in metastatic melanoma and colorectal cancer" Mol Cancer Ther; 8:2736-2745, Vincent et al. (2013) "Tumor targeting of the IL-15 superagonist RLI by an anti-GD2 antibody strongly enhances its antitumor potency." Int J Cancer; 133:757-765, or Kermer et al. (2012) "An antibody fusion protein for cancer immunotherapy mimicking IL-15 trans-presentation at the tumor site" Mol Cancer Ther; 11:1279-1288). The recombinant IL-15Rα or fragments thereof described in these references all comprise the so called "sushi domain", which is important for IL-15 binding to the IL-15Rα (see Wei et al. (2001) "The Sushi Domain of Soluble IL-15 Receptor α Is Essential for Binding IL-15 and Inhibiting Inflammatory and Allogenic Responses In Vitro and In Vivo" The Journal of Immunology; vol. 167, no. 1, p. 277-282). For the constructs comprising only IL-15, it is clear that they only function via binding to both the IL-15αR and the L-2/IL-15Rβγ. Without being bound to theory it is believed that this double-dependency on two receptors (α and βγ) renders the action of these IL-15 wild-type constructs less target cell specific. This is also demonstrated in the Examples of the present application, where fusion proteins of the present invention are shown to act in a much more target-restricted manner than the fusion proteins comprising wild-type IL-15.

It has also been shown that fusion proteins or complexes of IL-15 and IL-15RαFc are more effective in stimulating proliferation of memory-phenotype CD8+ cells and NK cells than the cytokine alone. Therefore, those fusion proteins have been termed "IL-15 superagonists". Due to the unexpected superagonistic function of IL15/IL-15Rα complexes it is highly unlikely that their effect might become target cell restricted by fusion to e.g. an antibody targeting a tumor associated antigen. That the activity of "IL-15 superagonists" is not further enhanced by Fc-crosslinking (Rubinstein et al. (2006) supports this notion. "Converting IL-15 to a superagonist by binding to soluble IL-15Rα" Proc Natl Acad Sci USA; 103:9166-9171). In contrast, the inventive fusion proteins described here comprising a binding protein and mutated IL-15 variants exhibit markedly reduced IL-15 activity unless they are bound to a target cell via the binding protein.

In particular, the present invention relates to a fusion protein comprising
a) a binding protein comprising at least one binding site, wherein the binding site binds to an antigen associated with a target cell; and
b) an IL-15 polypeptide, wherein the IL-15 polypeptide comprises at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO:1 thereby having a reduced affinity for IL-15Rα compared to the affinity of wild-type IL-15 of SEQ ID NO: 1 (Uniprot number: P40933-1).

The binding protein of the fusion protein of the present invention can be any protein that is able to bind an antigen that is associated with a target cell. The binding protein may be an antibody molecule, for example, an intact antibody, a divalent antibody fragment, or a monovalent antibody fragment. Alternatively, the binding protein can be a proteinaceous binding molecule with antibody-like binding properties.

An "antibody molecule" as used herein can be a full length antibody, a recombinant antibody molecule, or a fully human antibody molecule. A full length antibody is any naturally occurring antibody. The term "antibody" also includes immunoglobulins (Ig's) of different classes (i.e. IgA, IgG, IgM, IgD and IgE) and subclasses (such as IgG1, IgG2 etc.). Such full length antibodies can be isolated from different animals such as e.g. different mammalian species. A "recombinant antibody molecule" refers to an antibody molecule the genes of which has been cloned, and that is produced recombinantly in a host cell or organism, using well-known methodologies of genetic engineering. Typically, a recombinant antibody molecule has been genetically altered to comprise an amino acid sequence, which is not found in nature. Thus, a recombinant antibody molecule can be a chimeric antibody molecule or a humanized antibody molecule. In preferred embodiments, the fusion protein comprises the heavy chain of an immunoglobulin described herein and an IL-15 mutant described herein, which may be connected via a linker described herein. In this arrangement, it is preferred that the immunoglobulin moiety is located N terminally of the IL-15 mutant. In such a fusion protein, the light chain of the antibody molecule is paired with the antibody heavy chain as in any regular antibody or antibody fragment (cf. in this respect, also FIG. 1A)

The binding protein of the fusion protein of the present invention can also be an "antibody fragment". Such antibody fragments comprise at least those parts of an antibody, that form the (antigen) binding site. Illustrative examples of such an antibody fragment are single chain variable fragments (scFv), Fv fragments, single domain antibodies, such as e.g. VHH (camelid) antibodies, di-scFvs, fragment antigen binding regions (Fab), F(ab')₂ fragments, Fab' fragments, diabodies, domain antibodies, (Holt L J, Herring C, Jespers L S, Woolven B P, Tomlinson I M. Domain antibodies: proteins for therapy. *Trends Biotechnol.* 2003 November; 21(11):484-90), or bispecific "Fabsc"-antibody molecules as described in International patent application WO 2013/092001 comprising a single chain Fv fragment which is connected to an Fab fragment via a CH2 domain to name only a few.

As indicated above, the binding protein of the fusion protein of the present invention may be an antibody or a divalent antibody fragment comprising two binding sites with different specificities, for example, one specificity against a tumor associated antigen such as FLT3, CD20, CD10, CD21, CD22, CD25, CD30, CD33, CD34, CD37, CD38, or CD44v6 (see also below) and an receptor such as CD3 or CD16 that is present on effector cells such as T-cells or NK cells. Non limiting examples of formats that can be used for such divalent antibody fragments include a (Fab)$_2$'-fragment, a bispecific single-chain Fv fragment, a bsFc-1/2-dimer or a bsFc-CH3-1/2 dimer as described in International Patent Application WO 2013/092001. Also e.g. bispecific (or trispecific) antibody molecules described e.g. in Lamerisa et al. (2014) "Bispecific antibody platforms for cancer immunotherapy" *Crit Rev Oncol Hematol.* S1040-8428(14)00135-8, Kontermann (2012) "Dual targeting strategies with bispecific antibodies" Landes Bioscience mAbs Vol. 4, Issue 2 182-197 can be utilized. Alternatively, the binding protein of the fusion protein of the present invention can also be a bivalent proteinaceous artificial binding molecule such as a lipocalin mutein that is also known as "duocalin".

The binding protein of the fusion protein of the present invention may however only have a single binding site, i.e., may be monovalent. Examples of monovalent binding proteins include, but are not limited to, a monovalent antibody fragment, a proteinaceous binding molecule with antibody-like binding properties. Examples of such monovalent antibody fragments include, but are not limited to a Fab fragment, a Fv fragment, a single-chain Fv fragment (scFv) or a scFv-Fc fragment.

As explained above, the binding protein of the fusion protein of the present invention may alternatively be a proteinaceous binding molecule with antibody-like binding properties. Illustrative examples of proteinaceous binding molecules with antibody-like binding properties that can be used as binding proteins include, but are not limited to, an aptamer, a mutein based on a polypeptide of the lipocalin family (exemplary lipocalin muteins that are also known under their trademark name "Anticalin®" are, for example, described in PCT applications WO 99/16873, WO 00/75308, WO 03/029471, WO 03/029462, WO 03/029463, WO 2005/019254, WO 2005/019255, WO 2005/019256, WO 2006/56464 or WO 2008/015239, or the review article of Skerra, A. (2001) *Rev. Mol. Biotechnol.* 74, 257-275), a glubody, a protein based on the ankyrin scaffold, a protein based on the crystalline scaffold, an adnectin, an avimer, a EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain (complement control protein (CCP) modules), a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (III CR1, Gonzales J N, Houtz E K, Ludwig J R, Melcher E D, Hale J E, Pourmand R, Keivens V M, Myers L, Beidler K, Stuart P, Cheng S, Radhakrishnan R. Design and construction of a hybrid immunoglobulin domain with properties of both heavy and light chain variable regions. Protein Eng. 1997 August; 10(8):949-57) "Minibodies" (Martin F1, Toniatti C, Salvati A L, Venturini S, Ciliberto G, Cortese R, Sollazzo M. The affinity-selection of a minibody polypeptide inhibitor of human interleukin-6. EMBO J. 1994 Nov. 15; 13(22):5303-9), "Janusins" (Traunecker A, Lanzavecchia A, Karjalainen K. Bispecific single chain molecules (Janusins) target cytotoxic lymphocytes on HIV infected cells. EMBO J. 1991 December; 10(12):3655-9 and Traunecker A, Lanzavecchia A, Karjalainen K. Janusin: new molecular design for bispecific reagents. Int J Cancer Suppl. 1992; 7:51-2), a nanobody, an adnectin, a tetranectin, a microbody, an afilin, an affibody or an ankyrin, a crystallin, a knottin, ubiquitin, a zinc-finger protein, an autofluorescent protein, an ankyrin or an ankyrin repeat protein or a leucine-rich repeat protein, an avimer (Silverman J1, Liu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P. Multivalent avimer proteins evolved by exon shuffling of a family of human receptor domains. Nat Biotechnol. 2005 December; 23(12):1556-61. Epub 2005 Nov. 20); as well as multivalent avimer proteins evolved by exon shuffling of a family of human receptor domains as also described in Silverman et al. (Silverman J, Liu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P. Multivalent avimer proteins evolved by exon shuffling of a family of human receptor domains. Nat Biotechnol. 2005 December; 23(12):1556-61. Epub 2005 Nov. 20).

The term "binding protein" of the fusion protein of the present invention also includes a non-proteinaceous aptamer. Such an aptamer is an oligonucleic acid that binds to a specific target molecule. These aptamers are usually created by selecting them from a large random sequence pool, but natural aptamers also exist. More specifically, aptamers can be classified as: DNA or RNA aptamers. They consist of (usually short) strands of oligonucleotides. Therefore, a proteinaceous aptamer as described above may also include an oligonucleotide portion in addition to a protein portion.

The binding protein of the fusion protein of the present invention can thus be a proteinaceous binding molecule with antibody-like binding properties, which is selected from the group of an aptamer, a mutein based on a polypeptide of the lipocalin family, a glubody, a protein based on the ankyrin scaffold, a protein based on the crystalline scaffold, an adnectin, or an avimer.

The (receptor) protein that is bound by the binding protein can be any antigen associated with a target cell as described herein. It is envisioned in this context by the present invention that also a ligand of a receptor protein that is being selected herein as a target of the binding protein be a (target) protein, which is associated with a target cell as described herein. Examples for such a naturally occurring or recombinant ligand that binds a receptor protein associated with a target cell are CD135 also known as Fms-like tyrosine kinase 3 (FLT-3), receptor-type tyrosine-protein kinase FLT3, or fetal liver kinase-2 (Flk2). CD135 is the receptor for the cytokine Flt3 ligand (FLT3L). Thus, also the FLT3L can be used as a binding protein to bind to FLT-3. On the other hand also the FLT-3 receptor may be used as binding protein to bind to the FLT-3L.

Turning now to the physiological action of a fusion protein of the invention, the capability to recruit Fc-receptor (FcR)-positive immune effector cells, such as NK cells, is seen as important for the therapeutic activity of the fusion proteins of the present invention. While a fusion protein containing as binding protein ("part a)" of the fusion protein) such as an antibody molecule with constant CH2 and CH3 domains can be used for this purpose, it is noted that various strategies are known to the person skilled in the art that can be used to enhance antibody dependent cellular cytotoxicity (ADCC)-activity of the binding proteins of the fusion proteins (exemplarily summarized in Beck et al. (2010) and Natsume et al. (2009) (Beck A et al. (2010) "Strategies and challenges for the next generation of therapeutic antibodies. Nat Rev Immunol; 10:345-352; Natsume A, Niwa R, Satoh M. "Improving effector functions of antibodies for cancer treatment: Enhancing ADCC and CDC" Drug Des Devel Ther. 2009; 3:7-16). The ability to recruit Fc-receptor positive immune effector cells is however by no means limited to fusion proteins in the binding protein is based on an antibody/immunoglobulin. Rather, it is for example, also possible to use as a binding protein other proteinaceous molecules such as a lipocalin mutein which is fused with a part of an Fc polypeptide (that may comprise a CH2 and/or CH3 domain) that provides ADCC activity. The Fc polypeptide is in turn fused with a mutated IL-15 polypeptide as described herein. In such a fusion protein the Fc part/polypeptide serves not only the "ADCC activity" providing moiety but at the same time as a linker between the binding protein and the mutated IL-15 polypeptide.

Thus, the binding protein of the fusion protein of the present invention may be modified such that it has an enhanced antibody dependent cellular cytotoxicity (ADCC)-activity compared to an unmodified binding protein. The ADCC activity can be measured by well-known tests, such as e.g. aCella™-TOX, a GAPDH release Assay, which can be obtained from e.g. Promega or Interchim. Alternatively, ADCC can also be measured as described in the Examples herein. The modified binding protein of the fusion protein of the present invention may thus have an increased ADCC activity when compared to the (same but) unmodified binding protein not comprising the modification. For example, a modified 4G7 antibody as described herein in the Examples has an increased ADCC activity than a "normal" 4G7 antibody not comprising the SDIE modifications in its Fc part.

One of the strategies to improve cell killing activity of the fusion proteins of the present invention may, for example, be the use of conventional chimeric as well as of Fc-optimized antibody molecules containing an "SDIE mutation". The latter antibodies are known to mediate markedly enhanced antibody dependent cellular cytotoxicity (ADCC) (Lazar et al. (2006) "Engineered antibody Fc variants with enhanced effector function. Proc Nat Acad Sci USA 2006; 103:4005-4010; Horton et al. (2008) "Potent in vitro and in vivo activity of an Fc-engineered anti-CD19 monoclonal antibody against lymphoma and leukemia" Cancer Res; 68:8049-8057; Foyil and Bartlett (2010) "Anti-CD30 Antibodies for Hodgkin lymphoma" Curr Hematol Malig Rep; 5:140-147).

Therefore, the modified binding protein binding protein of the fusion protein of the present invention can be Fc optimized. This modification results in an enhanced antibody dependent cellular cytotoxicity (ADCC)-activity compared to the ADCC-activity of the unmodified binding protein. The modified binding protein can, for example, be an intact antibody, a scFv-Fc fragment, a bsFc-1/2 dimer or a bsFc-CH3-1/2 dimer. The latter two antibody formats are described in the International Patent application WO2013/092001.

In particular, the Fc-optimization can comprise an amino acid substitution, which is selected from the group consisting of F243L and/or D270E and/or R292P and/or S298A and/or S298N and/or Y300L and/or 305I and/or A330V and/or A330L and/or I332E and/or E333A and/or K334A and/or P396L and/or S239D wherein the positional numbering is according to the EU index. The numbering of amino acids used corresponds to the sequence positions according to the Kabat numbering [EU-Index]. The Fc-optimized modified binding protein can also comprise an "SDIE" mutation as described in Hofmann et al. (2012) "Generation, selection and preclinical characterization of an Fc-optimized FLT3 antibody for the treatment of myeloid leukemia" Leukemia; 26:1228-1237. Thus, the Fc-optimization can comprise an amino acid substitution comprising S239D and I332E wherein the positional numbering is according to the EU index. The Fc-optimization can also comprise the amino acid substitutions F243L, R292P, Y300L, V305I, and P396L wherein the positional numbering is according to the EU index. The Fc-optimization can also comprise the amino acid substitutions F243L, R292P and Y300L wherein the positional numbering is according to the EU index.

It is also envisioned that the indicated amino acid substitutions correspond to the indicated amino acid positions. That means that, for example, in antibody fragments or binding proteins comprising an Fc domain the positional numbering of the indicated amino acids may differ but may still have similar neighboring amino acids as also described herein below in more detail.

As explained above the capability to recruit Fc-receptor (FcR)-positive immune effector cells, such as NK cells, is considered as being crucial for the therapeutic activity of most antibodies. Another strategy to obtain modified binding proteins with an enhanced antibody dependent cellular cytotoxicity (ADCC)-activity, when compared with the unmodified binding protein is achieved by genetic engineering of the glycosylation pattern of the modified binding protein.

Thus, if corresponding antibody molecules are being used as binding protein, such a modified binding protein of the fusion protein of the present invention may have a glycosylation pattern of Fc-linked oligosaccharides that is different from the glycosylation pattern of Fc-linked oligosaccharides of the unmodified binding protein. In particular, the modified binding protein is less fucosylated than the unmodified binding protein. The modified binding protein can also be non-fucosylated. For example, the Fc-linked oligosaccharides of the modified binding protein can be 10%, 20%, 30%, 40%, 50%, 60%, 70%, 80%, 90%, 95%, 99% or 100% less fucosylated than the Fc-linked oligosaccharides of the unmodified binding protein. In general the fucosylation of a protein can be measured by techniques known to the person skilled in the art. For example, one may use Click-iT® fucose alkyne from Life Technologies or a method as described in EP 2483693.

The modified binding protein of the fusion protein of the present invention can also comprise both, an Fc-optimization and a glycosylation pattern of Fc-linked oligosaccharides that is different from the glycosylation pattern of the Fc-linked oligosaccharides of the unmodified binding protein.

Thus, in principle an enhanced ADCC of the binding protein of the present invention can be achieved by genetic engineering of the glycosylation pattern and/or the amino acid sequence of the CH2 domain of the IgG-Fc part that is contained in most antitumor antibodies in current clinical use (Shinkawa et al. (2003) "The absence of fucose but not the presence of galactose or bisecting N-acetylglucosamine of human IgG1 complex-type oligosaccharides shows the critical role of enhancing antibody-dependent cellular cytotoxicity" J Biol Chem; 278:3466-3473; Lazar et al. (2006) "Engineered antibody Fc variants with enhanced effector function" Proc Nat Acad Sci USA; 103:4005-4010).

Both strategies have already been used by the pharmaceutical industry for the development of Fc optimized third generation antibodies (Oflazoglu & Audoly (2010) "Evolution of anti-CD20 monoclonal antibody therapeutics in oncology" MAbs; 2:14-19): Roche (Basel, Switzerland) in cooperation with Glycart (Schlieren, Switzerland) has developed a glyco engineered CD20-antibody GA101 (Obinutuzumab). In a recent large clinical trial with patients suffering from chronic lymphatic leukemia (OLL) this antibody was superior to Rituxan (Goede et al. (2014) "Obinutuzumab plus Chlorambucil in Patients with CLL and Coexisting Conditions" N Engt J Med; 370:1101-1110). Two other antibodies directed to the lymphoma associated antigens CD19 (XmAb5574) and CD30 (XmAb2513), developed by Xencor (Monrovia, Calif. USA) carry the amino acid exchanges S239D and I332E (SDIE-modification). As GA101, these antibodies were reported to exert marked ADCC (Horton et al. (2008) "Potent in vitro and in vivo activity of an Fc-engineered anti-CD19 monoclonal antibody against lymphoma and leukemia" Cancer Res; 68:8049-8057; Foyil and Bartlett (2010) "Anti-CD30 Antibodies for Hodgkin lymphoma" Curr Hematol Malig Rep; 5:140-147) and are currently evaluated in clinical trials). Such commercially available binding proteins include veltuzumab (anti-CD20 antibody), ocrelizumab (anti-CD20), ocratuzumab (anti-CD20 antibody), obinutuzumab (anti-CD20 antibody), XmAb5574 (anti-CD19 antibody) and XmAb2513 (anti-CD20 antibody).

In principle, though any commercially available binding protein can be used for the fusion protein of the present invention. Further exemplary and purely illustrative binding proteins which can be used in the fusion protein of the present invention include rituximab (anti-CD20 antibody), ibritumomab (anti-CD20 antibody), tiuxetan (anti-CD20 antibody), tositumomab (anti-CD20 antibody), ofatumumab (anti-CD20 antibody), brentuximab vedotin (anti-CD30 antibody), gemtuzumab (anti-CD33 antibody), ozogamicin (anti-CD33 antibody), IGN101 (anti-EpCAM antibody), adecatumumab (anti-EpCAM antibody), labetuzumab (anti-CEA antibody), minretumomab (anti-TAG-72 antibody), J591 (anti-PSMA antibody), hu3S193 (anti-Lewis Y antibody), IgN311 (anti-Lewis Y antibody), IM-2C6 (anti-VEGF antibody), CDP791 (anti-VEGF antibody), brevacizumab (anti-VEGF antibody), trastuzumab (anti-ERBB2 antibody), pertuzumab (anti-ERBB2 antibody), MM-121 (anti-ERBB3 antibody), cetuximab (anti-EGFR antibody), panitumumab (anti-EGFR antibody), nimotuzumab (anti-EGFR antibody), 806 (anti-EGFR antibody), sibrotuzumab (anti-FAP antibody), F19 (anti-FAP antibody) and 8106 (anti-tenascin antibody). It is further contemplated by the present invention that commercially available binding proteins can be modified such that they have an enhanced ADCC activity compared to their unmodified counterparts.

As mentioned above, also envisioned are bispecific binding proteins with one binding site binding to an antigen which is associated with a target cell as described herein, while the second binding site of the bispecific binding proteins binds to an antigen associated with an effector cell or a target cell. Antigens associated with an effector cell can include e.g. CD3 or CD16.

Different bispecific antibodies and divalent antibody fragments have already been used in clinical settings. Examples of such bispecific antibodies and divalent antibody fragments that can also be used for the fusion proteins of the present invention include BiMAb (anti-CD16×anti-CD30 bispecific monoclonal antibody), HRS-3/A9 (anti-CD16× anti-CD30 antibody), catumaxomab (removab, anti-EpCAM x anti-CD3), ertumaxomab (anti-HER2×anti-CD3), SHR-1 (anti-CD3×anti-CD19), blinatumomab, CBA-CEACD3 (CD3×CEA), BIS-1 (anti-EGP-2×anti-CD3), MT-110 (anti-EpCAM×anti-CD3), EGFRBi (anti-CD3× anti-EGFR BiAb), CD20Bi (anti-CD3×anti-CD20 BiAb), MGD006 (anti-CD123×anti-CD3), FBTA05 (anti-CD20× anti-CD3), MGD007 (anti-gpA33×anti-CD3), MOR209/ES414 (anti-PSMA×anti-CD3), BAY2010112 (anti-PSMA× anti-CD3), triomab antibodies such as anti-CD3×anti-EpCAM triomab and EGFRXCD3 bsFab$_2$ (Jung et al. Int J Cancer "Local immunotherapy of glioma patients with a combination of 2 bispecific antibody fragments and resting autologous lymphocytes: evidence for in situ T-cell activation and therapeutic efficacy." January 15; 91(2):225-30, 2001). In one particular example, the bispecific antibody molecule binds CD3 and CD19. Examples of such bispecific CD3×CD19 antibody molecules include those single-chain antibody molecules that are described in International Patent Applications WO 99/54440 and WO 2004/106381. Such commercially available binding proteins may also be modified such that they exhibit an enhanced ADCC activity compared to the unmodified binding protein as described herein.

It is noted here that it is within the knowledge of the person of average skill in the field of protein expression and purification to construct a fusion of any such binding protein described herein (antibody molecule or a proteinaceous binding protein) with antibody-like properties such as "Anticalin®") with a mutated IL-15 polypeptide as used herein. Typically, for this purpose, a nucleic acid is generated which allows, upon expression, the fusion of the mutated IL-15 polypeptide at either the C- or the N-terminus of the binding protein. It is within the knowledge of the person of average skill in the art to determine (empirically) how to fuse the mutated IL-15 polypeptide to the binding protein while maintaining the functionality of both moieties in the fusion protein of the invention.

It is further envisioned that in one specific embodiment the binding protein of the fusion protein of the present invention comprises a binding site of the 4G7 antibody, which has a sequence identity of at least 80%, or at least 85%, or at least 90%, or at least 95%, or at least 98%, or at least 99% or 100% to SEQ ID NO. 5 (the sequence of the heavy chain of the variable domain of 4G7). The binding protein of the fusion protein of the present invention can additionally, or alternatively also comprise a binding site of the 4G7 antibody, which has a sequence identity of at least 80%, or at least 85%, or at least 90%, or at least 95%, or at least 98%, or at least 99% or 100% to SEQ ID NO. 6 (the sequence of the light chain of the variable domain of 4G7). Also these binding proteins may also be modified such that they exhibit an enhanced ADCC activity compared to the unmodified binding protein as described herein.

It is also envisioned that the binding protein of the fusion protein of the present invention comprises a binding site of the BV10 antibody, which has a sequence identity of at least 80%, or at least 85%, or at least 90%, or at least 95%, or at least 98%, or at least 99% or 100% to SEQ ID NO. 7 (the sequence of the heavy chain of the variable domain of BV10). The binding protein of the fusion protein of the present invention can additionally, or alternatively also comprise a binding site of the BV10 antibody, which has a sequence identity of at least 80%, or at least 85%, or at least 90%, or at least 95%, or at least 98%, or at least 99% or 100% to SEQ ID NO. 8 (the sequence of the light chain of the variable domain of BV10). Also these binding proteins may also be modified such that they exhibit an enhanced ADCC activity compared to the unmodified binding protein as described herein.

It is also envisioned that the binding protein of the fusion protein of the present invention comprises a binding site of the 4G8 antibody, which has a sequence identity of at least 80%, or at least 85%, or at least 90%, or at least 95%, or at least 98%, or at least 99% or 100% to SEQ ID NO. 9 (the sequence of the heavy chain of the variable domain of 4G8). The binding protein of the fusion protein of the present invention can additionally, or alternatively also comprise a binding site of the 4G8 antibody, which has a sequence identity of at least 80%, or at least 85%, or at least 90%, or at least 95%, or at least 98%, or at least 99% or 100% to SEQ ID NO. 10 (the sequence of the light chain of the variable domain of 4G8). Also these binding proteins may also be modified such that they exhibit an enhanced ADCC activity compared to the unmodified binding protein as described herein.

It is further envisioned that the binding protein of the fusion protein of the present invention comprises a binding site of the J591 antibody, which has a sequence identity of at least 80%, or at least 85%, or at least 90%, or at least 95%, or at least 98%, or at least 99% or 100% to SEQ ID NO. 11 (the sequence of the heavy chain of the variable domain of J591). The binding protein of the fusion protein of the present invention can additionally, or alternatively also comprise a binding site of the J591 antibody, which has a sequence identity of at least 80%, or at least 85%, or at least 90%, or at least 95%, or at least 98%, or at least 99% or 100% to SEQ ID NO. 12 (the sequence of the light chain of the variable domain of J591). The J591 antibody is described in U.S. Pat. No. 6,107,090 and has also been deposited under accession number ATCC HB-12126. Also these binding proteins may also be modified such that they exhibit an enhanced ADCC activity compared to the unmodified binding protein as described herein.

As mentioned above, the binding protein of the fusion protein of the present invention comprises at least one binding site. The binding protein may however also comprise two or more (for example three or four) binding sites.

It is further envisioned that the binding protein of the fusion protein of the present invention comprises a binding site of the K-ro23 antibody, which has a sequence identity of at least 80%, or at least 85%, or at least 90%, or at least 95%, or at least 98%, or at least 99% or 100% to SEQ ID NO: 25 (the sequence of the heavy chain of the variable domain of K-ro23). The binding protein of the fusion protein of the present invention can additionally, or alternatively also comprise a binding site of the K-ro23 antibody, which has a sequence identity of at least 80%, or at least 85%, or at least 90%, or at least 95%, or at least 98%, or at least 99% or 100% to SEQ ID NO: 26 (the sequence of the light chain of the variable domain of K-ro23). Also these binding proteins may also be modified such that they exhibit an enhanced ADCC activity compared to the unmodified binding protein as described herein.

The binding site of the binding protein of the fusion protein of the present invention binds to an antigen associated with a target cell. The target cell can, for example, express a tumor associated antigen (TAA) and/or an antigen associated with autoimmune diseases. Non limiting examples of such a TAA include CD19, CD20, CD10, CD21, CD22, CD25, CD30, CD33, CD34, CD37, CD38, CD44v6, CD45, CDw52, Fms-like tyrosine kinase 3 (FLT-3, CD135), c-Kit (CD117), CSF1R, (CD115), CD123, CD133, PDGFR-α (CD140a), PDGFR-β (CD140b), chondroitin sulfate proteoglycan 4 (CSPG4, melanoma-associated chondroitin sulfate proteoglycan), Muc-1, EGFR, del-7-EGFR, EGFRvIII, Folate blocking protein, Her2neu, Her3, PSMA, PSCA, PSA, TAG-72, HLA-DR, IGFR, CD133, IL3R, fibroblast activating protein (FAP), Carboanhydrase IX (MN/CA IX), Carcinoembryonic antigen (CEA), EpCAM, CDCP1, Derlin1, Tenascin, frizzled 1-10, the vascular antigens VEGFR2 (KDR/FLK1), VEGFR3 (FLT4, CD309), Endoglin, CLEC14, Tem1-8, Tie2, mesothelin, epithelial glycoprotein 2 (EGP2), epithelial glycoprotein 40 (EGP40), cancer antigen 72-4 (CA72-4), interleukin 13 receptor alpha-2 subunit, IL13Rα2, Ig kappa light chain (κ), GD3-ganglioside (GD3), GD2-ganglioside (GD2), acetylated variants of GD2 and GD3, CD171, NCAM, alpha folate receptor (αFR), Lewis (Y), fetal acetylcholine receptor (FAR), avian erythroblastic leukemia viral oncogene homolog 3 (ERBB3), avian erythroblastic leukemia viral oncogene homolog 4 (ERBB4), avian erythroblastic leukemia viral oncogene homolog 2 (ERBB2), hepatocyte growth factor receptor (HGFR/c-Met), claudin 18.2, claudin 3, claudin 4, claudin 1, claudin 12, claudin 2, claudin 5, claudin 8, claudin 7, claudin 6, membrane bound CEA, Robo4 and CD138.

Exemplary antigens associated with autoimmune diseases include CD20, CD22, CD52 and TNFR, CD19, CD25, CD40. The target cell can be a tumor/cancer cell and/or a B cell.

The fusion protein of the present invention also comprises a mutated IL-15 polypeptide, wherein the IL-15 polypeptide comprises at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO: 1. Such a mutation results in an IL-15 polypeptide that has a reduced affinity for IL-15Rα compared to the affinity of wild-type IL-15 of SEQ ID NO: 1 (Uniprot number: P40933-1). The IL-15 polypeptide may also not bind at all to IL-15Rα. It is further envisioned by the present invention that the IL-15 polypeptide can bind to IL-2/IL-15Rβγ. In principle, however, any amino acid substitution/deletion that results in an IL-15 polypeptide having a reduced affinity for IL-15Rα compared to the affinity of wild-type IL-15 of SEQ ID NO: 1 is contemplated by the present invention.

The term "position" when used in accordance with the present invention means the position of an amino acid within an amino acid sequence depicted herein. The term "corresponding" as used herein also includes that a position is not only determined by the number of the preceding amino acids. The position of a given amino acid in accordance with the present invention which may be substituted may vary due to deletions or additional nucleotides elsewhere in e.g. the (mutant or fragment) IL-15 polypeptide. Similarly, the position of a given amino acid in accordance with the present invention which may be substituted may vary due to deletion or addition of amino acids elsewhere in in e.g. the (mutant, fragment or wild-type) IL-15 polypeptide.

Thus, by a "corresponding position" as used is the present invention it is understood that amino acids may differ in the indicated number but may still have similar neighboring amino acids. The amino acids which may be exchanged, deleted or added are also comprised by the term "corresponding position". Specifically, the skilled person may, when aligning the reference sequence (subject sequence) for example SEQ ID No: 1 with an amino acid sequence of interest (query sequence), for example, inspect a sequence of interest for the sequence of SEQ ID NO: 4 (or the corresponding nucleic acid sequence encoding this protein, respectively) when looking for the amino acid position as specified herein (i.e., a position corresponding to position 93 and/or 112 of the amino acid sequence shown in SEQ ID No: 1).

More specifically, the amino acid "L" or "E" respectively of said position is subject to substitution. Said "L" or "E" is then replaced by another amino acid. For example, the "L" of said position is substituted by an amino acid other than "L". Or, for example, the "E" of said position is substituted by an amino acid other than "E".

In order to determine whether an amino acid residue in a given (mutant, fragment) IL-15 polypeptide sequence corresponds to a certain position in the amino acid sequence of SEQ ID No: 1 the skilled person can use means and methods well-known in the art, e.g., alignments, either manually or by using computer programs such as BLAST2.0, which stands for Basic Local Alignment Search Tool or ClustalW or any other suitable program which is suitable to generate sequence alignments.

The IL-15 polypeptide of the fusion protein of the present invention can have at least 10%, 20%, 30%, 40%, 50%, 60%, 70%, 80%, 90%, 95% or 99% identity to the IL-15 polypeptide as shown in SEQ ID NO: 1.

The term "sequence identity" or "identity" as used in the present invention means the percentage of pair-wise identical residues—optionally following (homology) alignment of a sequence of a IL-15 polypeptide of the invention with a sequence in question—with respect to the number of residues in the longer of these two sequences. Identity is measured by dividing the number of identical residues by the total number of residues and multiplying the product by 100. Typically, the sequence identity of an IL-15 polypeptide sequence identified herein is defined as the percentage of amino acids in a candidate sequence (sequence of interest) that are identical with the amino acids in the protein sequence shown in SEQ ID No: 1.

The sequence identity may be determined after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publically available computer software such as BLAST, ALIGN, or Megalign (DNASTAR) software. Those skilled in the art can determine appropriate parameters for measuring alignment, including any algorithms needed to achieve maximum alignment over the full length of the sequences being compared. For example, BLAST2.0 (Altschul, Nucl. Acids Res. 25 (1997), 3389-3402; Altschul, J. Mol. Evol. 36 (1993), 290-300; Altschul, J. Mol. Biol. 215 (1990), 403-410; see also http://blast.ncbi.nlm.nih.gov/ Blast.cgi?CMD=Web&PAGE_TYPE=BlastHome), can be used to search for local sequence alignments.

The IL-15 polypeptide can also comprise at least one amino acid substitution at one or more positions corresponding to position(s) 93, 94, 97, 98, 99, 100, 114 and/or 115 of the amino acid sequence shown in SEQ ID NO: 1. The IL-15 polypeptide can also comprise at least one amino acid substitution at one or more positions corresponding to position(s) 94, 97, 99 and/or 100 of the amino acid sequence shown in SEQ ID NO: 1. The IL-15 polypeptide can also comprise at least one amino acid substitution at one or more positions corresponding to position(s) 94, 97 and/or 98 of the amino acid sequence shown in SEQ ID NO: 1. The IL-15 polypeptide can also comprise at least one amino acid substitution at one or more positions corresponding to position(s) 94 and/or 98 of the amino acid sequence shown in SEQ ID NO: 1.

The amino acid substitution can be any amino acid substitution, which results in a change of the amino acid at this position. In one embodiment, the amino acid is substituted with an acidic amino acid, such as aspartic acid, glutamic acid or a basic amino acid such as lysine. It is also envisioned by the present invention that the amino acid corresponding to position 94 of the amino acid sequence shown in SEQ ID NO: 1 is substituted with a basic amino acid. The basic amino acid can for example be selected from the group consisting of arginine, lysine or histidine, preferably lysine.

It is further contemplated by the present invention that the at least one amino acid substitution is selected from the group consisting of L44D, E46K, L47D, V49D, I50D, L66D, L66E, I67D, and I67E. The numbering of these amino acid substitutions corresponds to the polypeptide sequences of SEQ ID NO: 2, SEQ ID NO: 3 and SEQ ID NO: 4 (FIG. 5). Thus, these amino acid substitutions correspond to the amino acid substitutions L92D, E94K, L95D, V97D, I98D, L114D, L114E, I115D, and I115E with respect to SEQ ID NO: 1 see Tables 3 and 4 below.

TABLE 3

Amino acid position of amino acid substitution with regard to different SEQ ID NOs.

| Amino acid position of amino acid substitution with regard to SEQ ID NO: 1 | Corresponding amino acid position of amino acid substitution with regard to SEQ ID NO: 2 and SEQ ID NO: 4 in FIG. 5A |
|---|---|
| L92D | L44D |
| E94K | E46K |
| L95D | L47D |
| V97D | V49D |
| I98D | I50D |

TABLE 4

Amino acid position of amino acid substitution with regard to different SEQ ID NOs.

| Amino acid position of amino acid substitution with regard to SEQ ID NO: 1 | Corresponding amino acid position of amino acid substitution with regard to SEQ ID NO: 3 and SEQ ID NO: 4 in FIG. 5A |
|---|---|
| L114D | L66D |
| L114E | L66E |
| I115D | I67D |
| I115E | I67E |

The at least one amino acid substitution can also be selected from the group consisting of E46K, V49D and/or I50D in correspondence to the amino acid positions of SEQ ID NO: 2 or SEQ ID NO: 4 as depicted in FIG. 5. The at least one amino acid substitution can also be selected from the group consisting of E46K and/or I50D in correspondence to the amino acid positions of SEQ ID NO: 2 or SEQ ID NO: 4 as depicted in FIG. 5. The at least one amino acid substitution can further be selected from the group consisting of E46K in correspondence to the amino acid positions of SEQ ID NO: 2 or SEQ ID NO. 4 as depicted in FIG. 5A.

The at least one amino acid substitution can also be selected from the group consisting of E94K, V97D and/or I98D in correspondence to the amino acid positions of SEQ ID NO: 1. The at least one amino acid substitution can also be selected from the group consisting of E94K and/or I98D in correspondence to the amino acid positions of SEQ ID NO: 1. The at least one amino acid substitution can further be selected from the group consisting of E94K in correspondence to the amino acid positions of SEQ ID NO: 1.

The IL-15 polypeptide of the fusion protein of the present invention can be the full length IL-15 protein or any fragment or mutant thereof, wherein the fragment and or mutant has a reduced affinity for IL-15Rα compared to the affinity of wild-type IL-15 of SEQ ID NO: 1. It is further envisioned by the present invention that the fragment or mutant can further have the capability of binding to IL-2/IL-15Rβγ.

Thus, the IL-15 polypeptides as well as mutants or fragments thereof have two functions on the one hand they can bind to IL-2/IL-15Rβγ and on the other hand (and at the same time) they have a reduced affinity for IL-15Rα compared to the affinity of wild-type IL-15 of SEQ ID NO: 1.

An IL-15 polypeptide fragment can be any fragment of the IL-15 polypeptide that binds to IL-2/IL-15Rβγ and on the other hand (and at the same time) has a reduced affinity for IL-15Rα compared to the affinity of wild-type IL-15 of SEQ ID NO: 1. The fragment can comprises less amino acids than the IL-15 polypeptide of the fusion protein of the present invention. Such a fragment can also include amino acid deletions with respect to SEQ ID NO: 1. The IL-15 polypeptide fragment can have a length of less than 162 amino acids, for example, a length of less than 155, 150, 145, 140, 135, 130, 125, 120, 115, 110, 105, 100 or less than even 50 amino acids. An exemplary fragment can be the IL-15 polypeptide, which consists of or comprises at least the amino acid sequence shown in SEQ ID NO: 4, which comprises at least one amino acid substitution at one or more positions corresponding to position(s) 40, 41, 42, 43, 44, 45, 46, 47, 48, 60, 61, 62, 63 and/or 64 of the amino acid sequence shown in SEQ ID NO: 4. Such a IL-15 fragment, can of course, include the amino acid substitutions as described herein with regard to SEQ ID NO: 1, 2 or 3 (corresponding to the respective sequence positions in SEQ ID NO: 4). An IL-15 polypeptide fragment can also at least comprise the amino acids important for βγ receptor binding of SEQ ID NO: 1. For example a IL-15 polypeptide fragment can have an amino acid sequence including amino acid positions 55, 56, 58, 59, 116, 117, 156, 157, 160 of SEQ ID NO: 1.

An IL-15 polypeptide mutant may comprise additional amino acid substitutions or insertions with respect to the IL-15 polypeptide of the fusion protein of the present invention. Thus the IL-15 polypeptides may have at least 10%, 20%, 30%, 40%, 50%, 60%, 70%, 80%, 90%, 95% or 99% identity to the IL-15 polypeptide as shown in SEQ ID NO: 1.

In general the term "affinity" means the strength of interaction between an epitope and a binding proteins binding site. Methods for determining the affinity of a given binding protein/IL-15 polypeptide are well known to the person skilled in the art. The binding affinity of a mutant IL-15 polypeptide may be measured by a multitude of methods such as fluorescence titration, competition ELISA or surface plasmon resonance (BIAcore™). An IL-15 polypeptide having a reduced affinity for IL-15Rα has a lower affinity to the IL-15Rα compared to the affinity of wild-type IL-15 of SEQ ID NO: 1 to IL-15Rα. It is also envisioned by the present invention that the IL-15 polypeptide of the fusion protein of the present invention has an affinity to IL-15Rα which is 5%, 10%, 20%, 30%, 40%, 50%, 60%, 70%, 80%, 90%, 100% lower than the affinity of wild-type IL-15 of SEQ ID NO: 1 to IL-15Rα.

For the binding proteins and IL-15 polypeptides described herein, binding is considered specific when the binding affinity is higher than $10^{-7}$ M. In particular, binding is considered specific when binding affinity is about $10^{-8}$ to $10^{-11}$ M ($K_D$), or of about $10^{-9}$ to $10^{-11}$ M or even higher. Thus, binding proteins with an affinity of the first binding site and/or the second binding site and IL-15 polypeptides in the picomolar range (with a $K_D$ of $10^{-12}$ M) are also encompassed in the present invention.

It is also envisioned by the present invention that the IL-2/IL-15Rβγ can be expressed by an effector cell that is relied upon in pharmaceutical uses of the invention. This means that the effector cell can express IL-2/IL-15Rβγ. Exemplary effector cells include a NK cell or a T-cell, such as a CD8+ T cell, gamma delta T cell or NK T cell. An effector cell can also be a CD8+ T cell or a NK cell.

The binding protein and the IL-15 polypeptide of the fusion protein of the present invention can further comprise a linker. This also means that a linker may not be present and that the IL-15 polypeptide may be directly connected to the binding protein. However, a linker may also be present to connect the binding protein with the IL-15 polypeptide.

In the latter case, the linker can in principle be attached anywhere to the binding protein and the IL-15 polypeptide, usually in between the C-terminus of one part of the fusion protein and the N-terminus of the other part. Suitable linkers are known in the art and for example described in Chen et al. (2013) "Fusion protein linkers: property, design and functionality" Adv Drug Deliv Rev; 65(10):1357-69. The linker can therefore be any linker known in the art.

The linker may, for example, be a straight or branched hydrocarbon based moiety that is coupled to the both partners via activated chain side groups such as amino-, thiol or hydroxyl groups. The linker can also comprise cyclic moieties. If the linking moiety is a hydrocarbon-based moiety the main chain of the linker may comprise only carbon atoms but can also contain heteroatoms such as oxygen (O), nitrogen (N) or sulfur (S) atoms. The linker may for example include a $C_1$-$C_{20}$ carbon atom chain or a polyether based chain such as polyethylene glycol based chain with —(O—CH$_2$—CH$_2$)— repeating units. In typical embodiments of hydrocarbon based linkers, the linking moiety may comprise between 1 to about 150, 1 to about 100, 1 to about 75, 1 to about 50, or 1 to about 40, or 1 to about 30, or 1 to about 20, including 2, 3, 4, 5, 6, 7, 8, 9, 10, 11, 12, 13, 14, 15, 16, 17, 18, and 19 main chain atoms. For example, the linker may comprise:

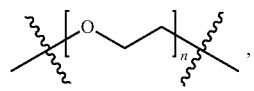

wherein n is an integer from 0 to 20, or from 1 to 10, or from 1 to 5, or wherein n is 3. Thus, for example n may be 0, 1, 2, 3, 4, 5, 6, 7, 8, 9, 10, 11, 12, 13, 14, 15, 16, 17, 18, 19, or 20.

The linker may however also be a peptide linker of any suitable length as long as the linker does not interfere with the function of one or both parts of the fusion protein. The linker may comprise two or more, five or more, 10 or more, 15 or more, or 20 or more amino acid residues. The peptide linker may comprise any amino acid residue. In one embodiment, the peptide linker may be rich in small or polar amino acids such as Gly and Ser, but can contain additional amino acids such as Thr and Ala to maintain flexibility, as well as polar amino acids such as Lys and Glu to improve solubility. Exemplary flexible linkers include but are not limited to $(GGGGS)_n$, wherein n can be a number between 1-7 (SEQ ID NO: 13), KESGSVSSEQLAQFRSLD (SEQ ID NO: 14) and EGKSSGSGSESKST (SEQ ID NO: 15), $(Gly)_8$ (SEQ ID NO: 16), GSAGSAAGSGEF (SEQ ID NO: 17), $(Gly)_6$ (SEQ ID NO: 18).

Exemplary rigid linkers include but are not limited to $A(EAAAK)_nA$, wherein n can be a number between 1-7 (SEQ ID NO: 19), $(XP)_n$ wherein n can be a number between 1-13, with X designating any amino acid, preferably Ala, Lys, or Glu, $(Ala-Pro)_7$ (SEQ ID NO: 20), or a 33-residue peptides containing repeating -Glu-Pro- or -Lys-Pro-. Exemplary in vivo cleavable linker include for example LEAGCKNFFPRSFTSCGSLE (SEQ ID NO: 21), G-S-S-T (SEQ ID NO: 22), CRRRRREAEAC (SEQ ID NO: 23).

In one embodiment, the fusion protein of the present invention comprises a linker, which comprises glycine and serine. The linker can, for example, comprise the amino acid sequence GGGGSGGGGSGGGGSGGGGS ((4-glycine 1-serine)$_4$; SEQ ID NO: 24). It is possible that either N-terminally and/or C-terminally such as "glycine-serine" linker may contain further amino acids that are arranged in between the IL-15 polypeptide and/or the binding protein. These additional amino acids may, for example, be present due to the cloning strategy that is used to generate the fusion protein of the invention. In one such illustrative example, an "glycine-serine" linker such as a $(GGGGS)_4$ linker may have an additional N-terminal serine (see, for example, the fusion protein shown in FIG. 6).

The linker will however not be attached to the actual binding site or binding sites of the binding protein and IL-15 polypeptide. For example, the linker(s) will often not be attached to the CDR3 regions of an antibody or antibody fragment.

For an antibody based binding protein, the linker(s) can, for example, be attached to the Fab part or the Fc part of the antibody molecule (binding protein). More particularly, the linker(s) may be attached to the CH3, CH2 or CH1 domain of the binding protein of the fusion protein of the present invention. Thus, the linker(s) can also be attached to the region, which is most external in a binding protein. This means that for example, the linker(s) can be attached to the CH2 domain in e.g. CH3 deleted binding proteins, or to the CH1 in CH2/CH3 deleted binding proteins. It also envisioned by the present invention that two linkers are attached to two CH3 regions of a binding protein such as an antibody, so that each CH3 domain has one linker attached. However, the linker may also be attached to only one CH3 region of a given binding protein. In one embodiment, the IL-15 polypeptide is linked to the CH3 domain of the binding protein via the linker.

It can however also be, for example, in the case of binding proteins sole consisting of the $V_H$ and $V_L$ chains of an antibody that the linker(s) is attached to the hinge region connecting the two chains. In the case of bispecific binding proteins such as e.g. BiTE constructs like Blinatumomab, the linker(s) can also be attached to the linker connecting the two different binding sites.

As pointed out herein typically linkers are attached to the Fc domain of binding proteins as described herein. Notably, it is additionally possible to fuse a CH1, CH2 and/or CH3 domain to a binding protein typically not comprising such domains. For example, this can be done for proteinaceous binding molecule with antibody-like binding properties as described herein or with immunoreceptors or their ligands as described herein. For example, such CH1, CH2 and/or CH3 domains can be fused to a lipocalin molecule via e.g. cloning these domains to the sequence encoding the proteinaceous binding molecule. In such cases a linker or more than one linker can then also be attached to these CH1, CH2 and/or CH3 domains.

In one illustrative embodiment, the fusion protein of the present invention may bind endoglin (CD105) as antigen and thus may comprise a binding protein that binds to endoglin. The binding protein may, for example, be an antibody molecule or an lipocalin mutein. Endoglin is a protein that is overexpressed on endothelial cells and that is essential for angiogenesis, therefore making it an important protein for tumor growth, survival and metastasis of cancer cells to other locations in the body. Endoglin is selectively expressed at high density on angiogenic endothelial cells and is upregulated by hypoxia through induction of hypoxia-inducible factor-1-a (HIF-1-a). Endoglin expression is also upregulated on tumor endothelial cells following inhibition of the VEGF pathway. In patients with solid tumors, high tumor microvessel density, as assessed by endoglin immunohistochemistry, has been correlated with poor prognosis. An exemplary endoglin-binding antibody that can be used in the fusion protein of the invention is K-ro23, which has been described in Schwartz, K, doctoral thesis, 2013, Eberhard Karls University, Tubingen, Germany, "Generierung, präklinische Charakterisierung and Optimierung monoklonaler Antikörper zur anti-angiogenetischen Therapie solider Tumoren". Another exemplary endoglin-binding antibody that can be used in fusion protein of the invention is the antibody termed TRC05, the variable domains of which are described in Seon et al., (2011), Endoglin targeted cancer therapy, Curr Drug Deliv, 8(1):135-143. The antibody TRC105 is currently being studied in clinical trials for the treatment of multiple solid tumor types, with phase 1 and phase 2 clinical trials being completed. Accordingly, a fusion protein of the present invention may preferably comprise the antibody binding site of K-ro23 or TRC105. This antibody binding site may comprise or preferably consist of an amino acid sequence which has a sequence identity of at least 80%, preferably at least 85%, preferably at least 90%, preferably at least 95%, preferably at least 98%, preferably at least 99% preferably 100% to SEQ ID NO. 27. Said fusion protein may further be attached, preferably covalently attached to an IgG light chain comprising or preferably consisting of an amino acid sequence which has a sequence identity of at least 80%, preferably at least 85%, preferably at least 90%, preferably at least 95%, preferably at least 98%, preferably at least 99% preferably 100% to SEQ ID NO. 28.

Another preferred binding partner for the binding site comprised in the fusion proteins of the invention is fibronectin, preferably the extra domain-B of fibronectin. Extra domain-B containing fibronectin (EDB-FN) is a high-molecular-weight glycoprotein that mediates cell adhesion and migration. The expression of EDB-FN is associated with a number of cancer-related biological processes such as tumorigenesis, angiogenesis, and epithelial-to-mesenchymal transition (EMT). A preferred embodiment of the fusion protein of the invention may thus comprise an antibody molecule that specifically binds to fibronectin, preferably the extra domain-B of fibronectin, and an IL-15 mutant described herein. In another preferred embodiment, the binding partner may be a lipocalin mutein described in International Patent Application WO2011/069992 that binds the fibronectin extra-domain B.

A further preferred binding partner for the binding site comprised in the fusion proteins of the invention is tenascin, preferably various isoforms of tenascin C. Tenascin C (TN-C) is a glycoprotein that in humans is encoded by the TNC gene. It is implicated in a number of different cancers such as osteosarcomas, chondrosarcomas, bladder cancer, and glioblastomas. In glioblastoma cells, Tenascin-C expression provides much clinical and functional significance in terms of cancer prognosis and tumor progression. A preferred embodiment of the fusion protein of the invention may thus comprise an antibody molecule that specifically binds to tenascin, preferably the tenascin c, and an IL-15 mutant described herein.

Further preferred binding partners comprised in the fusion proteins of the invention are carbohydrate antigens, such as gangliosides GD2 and GD3 and acetylated variants thereof. Such antigens are expressed on the cell surface of most cancers and their expression on normal tissue is often limited. GD2 antibodies as well as immunocytokines derived thereof have been successfully used for the treatment of children with neuroblastoma (see, for example, Navid et al, Immune Therapies for Neuroblastoma, Cancer Biol Ther. 2009 May; 8(10): 874-882, that reports clinical trial results for anti-GD2 antibodies such as the murine monoclonal anti-GD2 antibody 3F8, or the chimeric antibody Ch14.18 and the immunocytokine ch14.18-IL-2 in which the Fab portion of the antibody 14.18 was linked to IL-2.

The present invention also relates to the fusion protein of the present invention for use in target cell-restricted activation of effector cells expressing IL2/IL-15Rβγ. The term "target cell restricted effector cell activation" means that IL2/IL-15Rβγ expressing effector cells are activated in the presence of target cells. This is achieved by the fusion proteins of the present invention. On one hand, the fusion protein of the present invention comprises an IL-15 polypeptide as described herein, which binds to IL2/IL-15Rβγ expressing effector cells. In addition, the fusion protein of the present invention comprises a binding protein, which comprises at least one binding site, which binds to an antigen associated with a target cell. Thus, without being bound to theory, by bringing the effector and target cell in close proximity to each other, the effector cell can mediate its function such as target cell killing in a target cell specific manner. Thus, the present invention also relates to the fusion protein of the present invention for use in target cell-restricted target cell killing mediated by effector cell expressing IL-2/IL-15Rβγ. For example, the fusion protein of the present invention can be used in enhancing cytolytic activity of NK cells and T cells, preferably NK cells, gamma delta T cell, NK T cell and CD8+ T cells compared to the cytolytic activity of a fusion protein comprising an unmodified binding protein not having an enhanced ADCC-activity as defined herein.

The present invention also relates to the fusion protein of the present invention for use in treatment of a disease. This treatment can be any treatment which is based on the engagement of effector cells. Furthermore, any therapy directed at specific target cell associated antigens, involving engagement of effector cells is meant by this term. For example, the treatment of a disease can be the treatment of a proliferatory disease or an autoimmune disease.

Exemplary, and non-limiting examples of proliferatory diseases include adrenal cancer, anal cancer, bile duct cancer, bladder cancer, bone cancer, brain and spinal cord tumors, breast cancer, Castleman disease, cervical cancer, colon cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, lung cancer, non-small cell lung cancer, small cell lung cancer, lung carcinoid tumor, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, rectum cancer, retinoblastoma, rhabdomyosarcoma, salivary gland cancer, sarcoma, skin cancer, basal and squamous cell cancer, melanoma, merkel cell cancer, small intestine cancer, stomach cancer, testicular cancer, thymus cancer, thyroid cancer, uterine sarcoma, vaginal cancer, vulvar cancer, Waldenstrom macroglobulinemia, or Wilms tumor. The proliferatory disease can also be leukemia or lymphoma.

Non limiting examples of autoimmune diseases include Systemic lupus erythematosus (SLE), Goodpasture's syndrome, Sarcoidosis, Scleroderma, Rheumatoid arthritis, Dermatomyositis, Sjögren's Syndrome, Scleroderma, Dermatomyositis, Psoriasis, Vitiligo, Alopecia areata, Type 1 diabetes mellitus, Autoimmune pancreatitis, Hashimoto's thyroiditis, Addison's disease, Multiple sclerosis, Myasthenia gravis, Polyarteritis nodosa, Idiopathic thrombocytopenic purpura, Hemolytic anemia, Antiphospholipid antibody syndrome, Pernicious anemia, Gastrointestinal diseases, Celiac disease, Inflammatory bowel disease, Autoimmune hepatitis or Primary biliary cirrhosis.

With the fusion protein of the present invention it is intended to generally reduce side effects observed after application of IL-15 to human patients (Conlon et al. (2015) "Redistribution, hyperproliferation, activation of natural killer cells and CD8 T cells, and cytokine production during first-in-human clinical trial of recombinant human interleukin-15 in patients with cancer." J Clin Oncol. 33(1):74-82). Especially, these "side effects" are negative side effects, which are not beneficial to the patients. Without being bound to theory, it is believed that such negative side effects are due to unspecific (meaning non target cell specific) effector cell activation. Thus, since the fusion proteins of the present invention provide for a target cell restricted activation of effector cells, these side effects can be reduced or even diminished.

An "unspecific effector cell activation" or an "off target activation" of effector cells could therefore be any activation of effector cells, which is not related to the binding of the binding protein as described herein to an antigen associated with a target cell. For example, an off target effector cell activation could thus be a target cell-independent effector cell activation. In one embodiment, the unspecific effector cell activation comprises the activation of effector cells in the absence of target cells.

Illustrative examples of side effects include infusion reaction, elevated temperature/fever, dypnoe, circulatory system problems, immunogenicity, hypersensitivity reactions, immunosuppression, infections, anemia, autoimmune haemolytic anaemia, leukopenia, thrombopenia, pancytopenia, cytopenia, worsening heart failure, tumor lysis, cytokine release syndrome, thyroid disorders, cardiotoxicity, local skin reaction, elevated liver transaminases, hypotension, serum sickness, mucocutaneous reactions, hepatitis reactivation, progressive multifocal leukoencephalopathy (PML), renal toxicity and cardiac arrhythmias.

The fusion protein of the present invention can also be used to increase the dosage of the administered fusion protein compared to the dosage used for a fusion protein comprising the binding protein of the fusion protein of the present invention, and an IL-15 polypeptide not comprising at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO: 1.

The rationale behind this application is again the target cell restricted mode of action of the fusion proteins of the invention. The more target restricted the activity of a fusion molecule is, the smaller are the expected side effects, and thus the higher can be the applicable dosage. Thus, the fusion protein of the present invention can be used in treatment in such a way that the dosage of the administered fusion protein of the present invention is increased compared to the dosage used for fusion proteins comprising the binding protein as described herein and the wild-type IL-15 polypeptide (e.g. of SEQ ID NO: 1).

A "dosage" of the fusion protein of the present invention applied may vary within wide limits to achieve the desired preventive effect or therapeutic response. It will, for instance, depend on the affinity of a binding protein for a chosen target as well as on the half-life of the complex between a binding protein/IL-15 polypeptide and the target antigen in vivo. Further, the optimal dosage will depend on the biodistribution of the fusion protein of the present invention, the mode of administration, the severity of the disease/disorder being treated as well as the medical condition of the subject/patient. For example, when used in an ointment for topical applications, a high concentration of the fusion protein of the invention can be used.

Any suitable dosage of the fusion protein of the present invention can be used. It is within knowledge of the person of average skill in the art to, for example, empirically determine a suitable dosage of the fusion protein of the present invention. In illustrative embodiments, the fusion protein can be used in a dosage of about 0.3 mg/kg body weight of the patient, of about 0.5 mg/kg body weight, of about 1 mg/kg body weight, of about 2 mg/kg body weight, up to 20 mg/kg or even a higher dosage. The dosage can also be maximally 20 mg/m²/day, 15 mg/m²/day, 10 mg/m²/day, 7.5 mg/m²/day, 6 mg/m²/day, 4 mg/m²/day or less.

The present invention also relates to a pharmaceutical composition comprising the fusion protein of the present invention and optionally a pharmaceutically acceptable excipient. Accordingly, the fusion protein of the present invention can be formulated into compositions using pharmaceutically acceptable ingredients as well as established methods of preparation (Gennaro, A. L. and Gennaro, A. R. (2000) Remington: The Science and Practice of Pharmacy, 20th Ed., Lippincott Williams & Wilkins, Philadelphia, Pa.).

To prepare the pharmaceutical compositions, pharmaceutically inert inorganic or organic excipients can be used. To prepare e.g. pills, powders, gelatin capsules or suppositories, for example, lactose, talc, stearic acid and its salts, fats, waxes, solid or liquid polyols, natural and hardened oils can be used. Suitable excipients for the production of solutions, suspensions, emulsions, aerosol mixtures or powders for reconstitution into solutions or aerosol mixtures prior to use include water, alcohols, glycerol, polyols, and suitable mixtures thereof as well as vegetable oils.

The pharmaceutical composition may also contain additives, such as, for example, fillers, binders, wetting agents, glidants, stabilizers, preservatives, emulsifiers, and furthermore solvents or solubilizers or agents for achieving a depot effect. The latter is that fusion proteins may be incorporated into slow or sustained release or targeted delivery systems, such as liposomes and microcapsules.

The formulations can be sterilized by numerous means, including filtration through a bacteria-retaining filter, or by incorporating sterilizing agents in the form of sterile solid compositions which can be dissolved or dispersed in sterile water or other sterile medium just prior to use. Numerous possible applications for the fusion protein of the present invention exist in medicine.

The present invention also relates to a nucleic acid molecule encoding for the fusion protein of the present invention. The nucleic acid molecule may be DNA or RNA and may be of genomic or synthetic origin and may be single or double stranded. Examples of nucleic acids include mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label, which can then also be comprised by the fusion protein. Such an affinity tag can be his-tag, flag tag, strep-tag, HA-tag, calmodulin-tag or GFP-tag. The nucleic acid molecule of the present invention can for example be comprised in a vector. The present invention also relates to a host cell comprising the nucleic acid molecule of the present invention or the vector as described herein.

The present invention also relates to a method for producing the fusion protein of the present invention, comprising using the nucleic acid encoding the fusion protein for expression of the fusion protein under conditions allowing expression of the fusion protein. In one embodiment, the fusion protein is expressed by a host cell or in a cell-free system.

The present invention also relates to a method of treating a disease comprising administering a therapeutically effective amount of the fusion protein of the present invention to a subject. The disease can for example be a proliferatory or autoimmune disease as described herein.

The term "administration" means administering of a therapeutically effective dose of the fusion protein to a subject. The term "administering" also relates to a method of incorporating the fusion protein into tissues of an organism. Different routes of administration are possible. The fusion protein or the pharmaceutical composition of the present invention can, for example, be administered via different ways such as any parenteral or non-parenteral (enteral or topical) route that is therapeutically effective for (preferably proteinaceous) drugs. Parenteral application methods include, for example, subcutaneous, intramuscular, intracerebral, intracerebroventricular, intrathecal, intranasal, intraatrial, intraperitoneal or intravenous injection and infusion techniques, e.g. in the form of injection solutions, infusion solutions or tinctures. Non-parenteral delivery modes are, for instance, enteral delivery modes such as oral delivery, e.g. in the form of pills, tablets, capsules, solutions or suspensions, or rectally, e.g. in the form of suppositories. However, non-oral delivery is preferred. Topical application routes include epicutaneous or inhalational applications. An overview about pulmonary drug delivery, i.e. either via inhalation of aerosols (which can also be used in intranasal administration) or intracheal instillation is given by Patton et al. (2004) for example (J. S. Patton et al. The lungs as a portal of entry for systemic drug delivery. Proc. Amer. Thoracic Soc. 2004 Vol. 1 pages 338-344). In general, fusion proteins and pharmaceutical compositions of the present invention can be administered in formulations containing conventional non-toxic pharmaceutically acceptable excipients or carriers, additives and vehicles as desired and described herein.

Notably, the term "therapeutic" or "therapeutic effect" refers to the inhibition or activation of factors causing or contributing to the abnormal condition. For example, a therapeutic effect can be the killing of target cells mediated by the effector cells. Thus, one can measure such a therapeutic effect by measuring e.g. a decrease in e.g. tumor size or decrease in the amount of B cells in a subject that received the fusion protein or pharmaceutical composition of the present invention compared to the subject before application of the fusion protein or pharmaceutical composition of the present invention.

The fusion proteins or pharmaceutical compositions of the present invention can also be used in co-treatment with other therapies. Such a co-treatment can include administration of the fusion proteins or pharmaceutical compositions of the present invention, preferably in the form of a medicament, to a subject suffering from a disease, such as proliferatory or autoimmune disease and the administration of another medicament/drug. Examples of such additional drugs are drugs used in chemotherapy, radiation therapy, angiogenesis inhibitors or cancer vaccines. Further examples of such additional drugs are thyroid supplements, vitamins such as B12, or insulin injections, immunosuppressives, such as cortisol, natalizumab or Infliximab.

The fusion proteins or pharmaceutical compositions of the present invention can also be applied to a subject. The term "subject" can also mean human or an animal. The subject can also be a subject suffering from cancer or an autoimmune disease. The subject can be a vertebrate, more preferably a mammal. Mammals include, but are not limited to, farm animals, sport animals, pets, primates, mice and rats. Preferably, a mammal is as a human, dog, cat, cow, pig, mouse, rat etc., particularly preferred is a human being. Thus, in one embodiment, the subject is a vertebrate, preferably a human being.

The present invention also relates to a use of the fusion protein of the present invention or the pharmaceutical composition of the present invention in the manufacture of a medicament for treating a subject having a disease.

The present invention also relates to a kit comprising the fusion protein of the present invention. Such a kit can further comprise
  a) one or more buffer(s);
  b) one or more protocol(s).

Suitable buffers include buffers, in which the fusion proteins or pharmaceutical compositions of the present invention can be stored or in which they can be directly administered to the subject. In the latter case, such buffer is a non-toxic, physiologically acceptable buffer.

The present invention also relates to a method for reducing unspecific target cell activation in therapy, the therapy comprising administering to a subject a fusion protein of the present invention.

In addition, the present invention relates to a method for reducing a side effect in therapy, the therapy comprising administering to a subject a fusion protein of the present invention. Illustrative examples of a side effect include at least one of infusion reaction, elevated temperature/fever, dyspnoea, circulatory system problems, immunogenicity, hypersensitivity reactions, immunosuppression, infections, anemia, leukopenia, thrombopenia, worsening heart failure, tumor lysis, cytokine release syndrome, thyroid disorders, cardiotoxicity, local skin reaction, thyroid disorders, elevated liver transaminases, hypotension, serum sickness, mucocutaneous reactions, hepatitis reactivation, progressive multifocal leukoencephalopathy (PML), renal toxicity, or cardiac arrhythmias.

The present invention also relates to a method for increasing the dosage of a fusion protein in therapy, the therapy comprising administering to a subject a fusion protein of the present invention.

The present invention is further characterized by the following items:

1. A fusion protein comprising
a) a binding protein comprising at least one binding site, wherein the binding site binds to an antigen associated with a target cell; and
b) an IL-15 polypeptide, wherein the IL-15 polypeptide comprises at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO:1
thereby having a reduced affinity for IL-15Rα compared to the affinity of wild-type IL-15 of SEQ ID NO: 1 (Uniprot number: P40933-1).

2. The fusion protein of item 1, wherein the binding protein is selected from the group consisting of an antibody, a divalent antibody fragment, a monovalent antibody fragment, or a proteinaceous binding molecule with antibody-like binding properties.

3. The fusion protein of item 2, wherein the divalent antibody fragment is an (Fab)2'-fragment, a divalent single-chain Fv fragment, a bsFc-1/2-dimer or a bsFc-CH3-1/2 dimer.

4. The fusion protein of item 2, wherein the monovalent antibody fragment is selected from the group consisting of a Fab fragment, a Fv fragment, a single-chain Fv fragment (scFv) or an scFv-Fc fragment.

5. The fusion protein of item 2, wherein the proteinaceous binding molecule with antibody-like binding properties is selected from the group of an aptamer, a mutein based on a polypeptide of the lipocalin family, a glubody, a protein based on the ankyrin scaffold, a protein based on the crystalline scaffold, an adnectin, an avimer or a (recombinant) receptor protein.

6. The fusion protein of any of items 2-4, wherein the binding protein is modified such that it has an enhanced antibody dependent cellular cytotoxicity (ADCC)-activity compared to the unmodified binding protein.

7. The fusion protein of item 6, wherein the modified binding protein is Fc optimized.

8. The fusion protein of item 7, wherein the modified binding protein is an antibody, a scFv-Fc fragment, a bsFc-1/2 dimer or a bsFc-CH3-1/2 dimer.

9. The fusion protein of item 7 or 8, wherein the Fc-optimization comprises an amino acid substitution, which is selected from the group consisting of F243L and/or D270E and/or R292P and/or S298A and/or S298N and/or Y300L and/or 305I and/or A330V and/or A330L and/or I332E and/or E333A and/or K334A and/or P396L and/or S239D, preferably S239D and I332E, wherein the positional numbering is according to the EU index.

10. The fusion protein of item 6, wherein the modified binding protein has a glycosylation pattern of Fc-linked oligosaccharides that is different from the glycosylation pattern of Fc-linked oligosaccharides of the unmodified binding protein.

11. The fusion protein of item 10, wherein the modified binding protein is less fucosylated than the unmodified binding protein.

12. The fusion protein of item 11, wherein the modified binding protein is non-fucosylated.

13. The fusion protein of any of items 2-4, 6-12, wherein the binding protein comprises a binding site of the 4G7 antibody, which has a sequence identity of at least 80%, or at least 85%, or at least 90%, or at least 95%, or at least 98%, or at least 99% or 100% to SEQ ID NO. 5 (the sequence of the heavy chain of the variable domain of 4G7).

14. The fusion protein of any of items 2-4, 6-13, wherein the binding protein comprises a binding site of the 4G7 antibody, which has a sequence identity of at least 80%, or at least 85%, or at least 90%, or at least 95%, or at least 98%, or at least 99% or 100% to SEQ ID NO. 6 (the sequence of the light chain of the variable domain of 4G7).

15. The fusion protein of any of items 1-14, wherein the target cell expresses a tumor associated antigen (TAA) and/or an antigen associated with autoimmune diseases.

16. The fusion protein of item 15, wherein the TAA is selected from the group consisting of CD19, CD20, CD10, CD21, CD22, CD25, CD30, CD33, CD34, CD37, CD38, CD44v6, CD45, CDw52, Fms-like tyrosine kinase 3 (FLT-3, CD135), c-Kit (CD117), CSF1R, (CD115), CD123, CD133, PDGFR-α (CD140a), PDGFR-β (CD140b), chondroitin sulfate proteoglycan 4 (CSPG4, melanoma-associated chondroitin sulfate proteoglycan), Muc-1, EGFR, del-7-EGFR, EGFRvIII, Folate blocking protein, Her2neu, Her3, PSMA, PSCA, PSA, TAG-72, HLA-DR, IGFR, CD133, IL3R, fibroblast activating protein (FAP), Carboanhydrase IX (MN/CA IX), Carcinoembryonic antigen (CEA), EpCAM, CDCP1, Derlin1, Tenascin, frizzled 1-10, the vascular antigens VEGFR2 (KDR/FLK1), VEGFR3 (FLT4, CD309), Endoglin, CLEC14, Tem1-8, Tie2, mesothelin, epithelial glycoprotein 2 (EGP2), epithelial glycoprotein 40 (EGP40), cancer antigen 72-4 (CA72-4), interleukin 13 receptor alpha-2 subunit, IL13Rα2, Ig kappa light chain (κ), GD3-ganglioside (GD3), GD2-ganglioside (GD2), acetylated variants of GD2 and GD3, CD171, NCAM, alpha folate receptor (αFR), Lewis (Y), fetal acetylcholine receptor (FAR), avian erythroblastic leukemia viral oncogene homolog 3 (ERBB3), avian erythroblastic leukemia viral oncogene homolog 4 (ERBB4), avian erythroblastic leukemia viral oncogene homolog 2 (ERBB2), hepatocyte growth factor receptor (HGFR/c-Met), claudin 18.2, claudin 3, claudin 4, claudin 1, claudin 12, claudin 2, claudin 5, claudin 8, claudin 7, claudin 6, membrane bound CEA, Robo4, CD138, tenascin and the extra domain-B of fibronectin.

17. The fusion protein of item 15, wherein the target cell expresses an antigen associated with autoimmune diseases, which antigen is selected from the group consisting of CD20, CD22, CD52 and TNFR, CD19, CD25, CD40.

18. The fusion protein of any of items 1-17, wherein the target cell is a tumor/cancer cell and/or a B cell.

19. The fusion protein of any of items 1-18, wherein the IL-15 polypeptide comprises at least one amino acid substitution at one or more positions corresponding to position(s) 93, 94, 97, 98, 99, 100, 114 and/or 115 of the amino acid sequence shown in SEQ ID NO:1.

20. The fusion protein of item 19, wherein the IL-15 polypeptide comprises at least one amino acid substitution at one or more positions corresponding to position(s) 94, 97, 99 and/or 100 of the amino acid sequence shown in SEQ ID NO:1.

21. The fusion protein of item 19 or 20, wherein the amino acid corresponding to position 94 is substituted with a basic amino acid.

22. The fusion protein of item 21, wherein the basic amino acid is selected from the group consisting of arginine, lysine and histidine.

23. The fusion protein of any of items 1-18, wherein the at least one amino acid substitution is selected from the group consisting of L92D, E94K, L95D, V97D, I98D, L114D, L114E, I115D, I115E and/or, preferably E94K, V97D and/or I98D, most preferably E94K.

24. The fusion protein of any of items 1-23, wherein the IL-15 polypeptide does not bind to IL-15Rα.

25. The fusion protein of any of items 1-24, wherein the IL-15 polypeptide binds to IL-2/IL-15Rβγ.

26. The fusion protein of any of items 1-25, wherein the IL-15 polypeptide is full length IL-15 protein or a fragment or mutant thereof, which fragment or mutant has a reduced affinity for IL-15Rα compared to the affinity of wild-type IL-15 of SEQ ID NO: 1.

27. The fusion protein of item 26, wherein the fragment or mutant further has the capability of binding to IL-2/IL-15Rβγ.

28. The fusion protein of any of items 1-27, wherein the IL-15 polypeptide comprises at least an amino acid sequence as shown in SEQ ID NO: 4, which comprises at least one amino acid substitution at one or more positions corresponding to position(s) 44, 45, 46, 47, 48, 49, 50, 51, 52, 64, 65, 66, 67 and/or 68 of the amino acid sequence shown in SEQ ID NO: 4.

29. The fusion protein of item 25, wherein the IL-2/IL-15Rβγ is expressed by an effector cell.

30. The fusion protein of item 29, wherein the effector cell expresses IL-2/IL-15Rβγ.

31. The fusion protein of item 30, wherein the effector cell is a NK cell or a T-cell, preferably a NK cell, a CD8+ T cell, gamma delta T cell or NK T cell.

32. The fusion protein of any of items 1-31, wherein the fusion protein further comprises a linker, preferably a peptide linker.

33. The fusion protein of item 32, wherein the linker comprises glycine and serine.

34. The fusion protein of item 32 or 33, wherein the linker comprises more than 2, more than 5, more than 10, more than 15 or more than 20 amino acids, preferably the linker comprises 20 amino acids.

35. The fusion protein of item 33 or 34, wherein the linker comprises the amino acid sequence GGGGSGGGGSGGGGSGGGGS ((4-glycine 1-serine)4) (SEQ ID NO: 24).

36. The fusion protein of any of items 32-35, wherein the IL-15 polypeptide is linked to the CH3 domain of the binding protein via the linker.

37. The fusion protein of any one of the preceding items, wherein the antigen associated with a target cell is endoglin.

38. The fusion protein of item 37, wherein the fusion protein comprises an amino acid sequence that has a sequence identity of at least 80%, or at least 85%, or at least 90%, or at least 95%, or at least 98%, or at least 99% or 100% to SEQ ID NO: 27.

39. The fusion protein of item 38, wherein the fusion protein is covalently attached to an IgG light chain comprising an amino acid sequence that has a sequence identity of at least 80%, or at least 85%, or at least 90%, or at least 95%, or at least 98%, or at least 99% or 100% to SEQ ID NO. 28.

40. The fusion protein of any of items 1-39 for use in target cell-restricted activation of effector cells expressing IL2/IL-15Rβγ.

41. The fusion protein of any of items 1-39 for use in target cell-restricted target cell killing mediated by effector cell expressing IL-2/IL-15Rβγ.

42. The fusion protein of any of items 1-39 for use in enhancing cytolytic activity of NK cells and T cells, preferably NK cells, gamma delta T cell, NK T cell and CD8+ T cells compared to the cytolytic activity of an unmodified binding protein as defined in item 6.

43. The fusion protein of any of items 1-39 for use in treatment of a disease.

44. The fusion protein for use of item 43, wherein the disease is a proliferatory disease or an autoimmune disease.

45. The fusion protein for use of item 44, wherein the proliferatory disease is selected from the group consisting of adrenal cancer, anal cancer, bile duct cancer, bladder cancer, bone cancer, brain and spinal cord tumors, breast cancer, Castleman disease, cervical cancer, colon cancer, endometrial cancer, esophagus cancer, Ewing family of tumors, eye cancer, gallbladder cancer, gastrointestinal carcinoid tumors, gastrointestinal stromal tumor (GIST), gestational trophoblastic disease, Hodgkin disease, Kaposi sarcoma, kidney cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), liver cancer, lung cancer, non-small cell lung cancer, small cell lung cancer, lung carcinoid tumor, lymphoma, lymphoma of the skin, malignant mesothelioma, multiple myeloma, myelodysplastic syndrome, nasal cavity and paranasal sinus cancer, nasopharyngeal cancer, neuroblastoma, non-Hodgkin lymphoma, oral cavity and oropharyngeal cancer, osteosarcoma, ovarian cancer, pancreatic cancer, penile cancer, pituitary tumors, prostate cancer, rectum cancer, retinoblastoma, rhabdomyosarcoma, salivary gland cancer, sarcoma, skin cancer, basal and squamous cell cancer, melanoma, merkel cell cancer, small intestine cancer, stomach cancer, testicular cancer, thymus cancer, thyroid cancer, uterine sarcoma, vaginal cancer, vulvar cancer, Waldenstrom macroglobulinemia, or Wilms tumor.

46. The fusion protein for use of item 44, wherein the autoimmune disease is selected from the group consisting of Systemic lupus erythematosus (SLE), Goodpasture's syndrome, Sarcoidosis, Scleroderma, Rheumatoid arthritis, Dermatomyositis, Sjögren's Syndrome, Scleroderma, Dermatomyositis, Psoriasis, Vitiligo, Alopecia areata, Type 1 diabetes mellitus, Autoimmune pancreatitis, Hashimoto's thyroiditis, Addison's disease, Multiple sclerosis, Myasthenia gravis, Polyarteritis nodosa, Idiopathic thrombocytopenic purpura, Hemolytic anemia, Antiphospholipid antibody syndrome, Pernicious anemia, Gastrointestinal diseases, Celiac disease, Inflammatory bowel disease, Autoimmune hepatitis or Primary biliary cirrhosis.

47. The fusion protein for use of any of items 43-46, wherein side effects of the treatment are reduced.

48. The fusion protein for use of item 47, wherein the side effects include at least one of infusion reaction, elevated temperature/fever, dypnoe, circulatory system problems, immunogenicity, hypersensitivity reactions, immunosuppression, infections, anemia, autoimmune haemolytic anaemia, leukopenia, thrombopenia, pancytopenia, cytopenia, worsening heart failure, tumor lysis, cytokine release syndrome, thyroid disorders, cardiotoxicity, local skin reaction, elevated liver transaminases, hypotension, serum sickness, mucocutaneous reactions, hepatitis reactivation, progressive multifocal leukoencephalopathy (PML), renal toxicity, cardiac arrhythmias.

49. The fusion protein for use of any of items 43-48, wherein in treatment the dosage of the administered fusion protein is increased compared to the dosage used for a fusion protein comprising the binding protein of the fusion protein of any of items 1-36, and an IL-15 polypeptide not comprising at least one amino acid substitution at one or more positions corresponding to position(s) 92, 93, 94, 95, 96, 97, 98, 99, 100, 112, 113, 114, 115 and/or 116 of the amino acid sequence shown in SEQ ID NO:1.

50. A pharmaceutical composition comprising the fusion protein of any of items 1-39.

51. A nucleic acid molecule encoding for the fusion protein of any of items 1-39.

52. The nucleic acid molecule of item 51 comprised in a vector.

53. Host cell comprising the nucleic acid molecule of item 51 or the vector of item 52.

54. A method for producing the fusion protein of any of items 1-39, comprising using the nucleic acid encoding the fusion protein for expression of the fusion protein under conditions allowing expression of the fusion protein.

55. The method of item 54, wherein the fusion protein is expressed by a host cell or in a cell-free system.

56. A method of treating a disease comprising administering a therapeutically effective amount of the fusion protein as defined in any of items 1-39 to a subject.

57. The method of item 56, wherein the disease is a proliferatory or autoimmune disease.

58. A use of the fusion protein as defined in any of items 1-39 or the pharmaceutical composition of item 50 in the manufacture of a medicament for treating a subject having a disease.

59. The method of item 56 or use of item 58, wherein the subject is a vertebrate, preferably a human being.

60. A kit comprising the fusion protein of any of items 1-39.

61. The kit of item 60, wherein the kit further comprises
a) one or more buffer(s);
b) one or more protocol(s).

62. A method for reducing unspecific target cell activation in therapy, the therapy comprising administering to a subject a fusion protein of any of items 1-39.

63. A method for reducing a side effect in therapy, the therapy comprising administering to a subject a fusion protein of any of items 1-39.

64. The method of item 63, wherein the side effect includes at least one of infusion reaction, elevated temperature/fever, dypnoe, circulatory system problems, immunogenicity, hypersensitivity reactions, immunosuppression, infections, anemia, leukopenia, thrombopenia, worsening heart failure, tumor lysis, cytokine release syndrome, thyroid disorders, cardiotoxicity, local skin reaction, thyroid disorders, elevated liver transaminases, hypotension, serum sickness, mucocutaneous reactions, hepatitis reactivation, progressive multifocal leukoencephalopathy (PML), renal toxicity, cardiac arrhythmias.

65. A method for increasing the dosage of a fusion protein in therapy, the therapy comprising administering to a subject a fusion protein of any of items 1-39.

The invention is further illustrated by the following non-limiting Examples.

Example 1: Generation of Fusion Proteins

Construction of Fc-optimized, SDIE-modified antibodies is described in Hofmann et al. (2012) "Generation, selection and preclinical characterization of an Fc-optimized FLT3 antibody for the treatment of myeloid leukemia" Leukemia 26:1228-1237. A plasmid containing the human IL-15 sequence was obtained from the DKFZ Genomics and Proteomics Core facility (vector: pENTR221, hIL-15 GeneBank Accession number: DQ893709, also depicted in SEQ ID NO: 1). Notably, the first 48 amino acids of this sequence comprise the long 48 amino acid signal peptide, which is cleaved during secretion of hIL-15 and is not part of the IL-15 fusion proteins. BspEI and SpeI restriction sites were added via PCR at the 5' and 3' end of the IL-15 sequence which was afterwards cloned into the pJet1.2 blunt vector. In a first step, the BspEI restriction site within the IL-15 sequence was removed using mutagenesis PCR. In a second step the 3 different IL-15 polypeptides were generated via mutagenesis PCR (E46K, V49D, and I50D—these mutations correspond to amino acid substitutions E94K, V97D and I98D with regard to SEQ ID NO: 1, see also Table 3 as described herein). The four different IL-15 polypeptides were introduced via BspEI and SpeI restriction sites into an expression vector containing the variable domain for 4G7 (anti-CD19/αCD19) and the Fc optimized human IgG1 constant region, i.e. the constant domain carries the amino acid exchanges S239D and I332E (EU numbering). In these constructs the hIL-15 is directly linked to the CH3 domain via glycine-Serine (short linker) (FIG. 1).

The PSMA-IL-15wt and PSMA-IL-15-E46K constructs were generated accordingly with an expression vector containing the sequence for J591 (anti-PSMA). The constructs with the long linker were generated as follows: a sequence coding for the 20 amino acid long linker (4-glycine 1-serine)$_4$ plus the first 39 nucleotides of the IL-15 sequence were synthesized as DNA fragments (containing 5' BspEI and 3' BglII restrictions sites) at Eurofins Genomics, Ebersberg, Germany. The IL-15 sequence contains a BglII restriction site at nucleotide position 39, thus the (4G-1S)$_4$ linker was ligated into the different IL-15 containing expression vectors via BspEI and BglII. Likewise, the endoglin-IL-15wt and endoglin IL-15-E46K constructs were generated accordingly using an expression vector containing the sequence for K-ro23 (chimeric anti-endoglin antibody).

All heavy chain plasmids were transfected together with appropriate light chain vectors into SP2/0 cells. Single antibody producing clones were expanded and the antibodies were purified from the supernatant by affinity chromatography with protein A.

Example 2: Binding to IL-15Rα

CD19-positive NALM16 cells were incubated with different concentrations of distinct fusion proteins, stained with a recombinant, His-tagged IL-15R-α-Fc-fusion protein (R&D systems), a Biotin-labeled anti-His antibody (Qiagen) and finally with a streptavidin PE-conjugate (Life technologies). Cells were then analyzed by flow cytometry (BD FACS Calibur). To select the most suitable fusion proteins CD19-positive NALM16 cells were incubated with the indicated concentrations of distinct fusion proteins (on the y-axis of FIGS. 2 A and B).

Fusion protein αCD19-IL15wt comprised a 4G7 antibody (anti-CD19 antibody) with an Fc optimized human IgG1 constant region (SDIE mutation as described above) fused to wild-type human IL-15, wherein the hIL-15 is directly linked to the CH3 domain via glycine-serine (short linker). This fusion protein served as a control. Further tested fusion proteins named αCD19-IL15-E46K (4G7-IL15-E46K), αCD19-IL15-V49D (4G7-IL15-V49D) or αCD19-IL15-I50D (4G7-IL15-I50D) comprised the 4G7 antibody, with an Fc optimized (SDIE) human IgG1 constant region. The IL-15 polypeptide comprised the indicated amino acid substitution, respectively. These amino acid substitutions correspond to the numbering of SEQ ID NO: 2 (shown in FIG. 5A). In all these fusion proteins the hIL-15 is directly linked to the CH3 domain via glycine-serine (short linker).

Since the CD19 binding protein (here 4G7 antibody) is directed against CD19 it will thus bind to the NALM16 cells in this assay. To understand if the IL-15 polypeptides of the fusion proteins remained their ability to bind to IL-15Rα a His-tagged IL-15Rα-Fc-fusion protein (R&D systems) was added to the cultures. Thus, if the IL-15 polypeptide of the fusion proteins remained its ability to bind to IL-15Rα the added His-tagged IL-15Rα-Fc-fusion protein will remain bound via the fusion protein to the NALM 16 cells. Thus, upon addition of a Biotin-labeled anti-His antibody (Qiagen) and a streptavidin PE-conjugate (Life technologies) a detectable signal will be generated. This signal was measured by the Mean Fluorescence Intensity (MFI; y-axis of FIG. 2A).

FIG. 2 A shows that the MFI detected for the αCD19-IL15-wt (4G7-IL-15-wt) fusion protein is around 300 MFI. Since IL-15 normally binds to ILR-15Rα this signal provides evidence for a binding of IL-15 to ILR-15a. The αCD19-IL15-V49D (4G7-IL15-V49D) fusion protein performed not as prominent as the control thereby indicating that this fusion protein did bind to ILR-15α with a slightly reduced compared to the αCD19-IL-15-wt fusion protein. On the contrary, the fusion proteins αCD19-IL15-E46K and αCD19-IL15-I50D showed a MFI signal of around 150, indicating that the binding to ILR-15α is strongly diminished (or even absent) compared to the αCD19-IL-15-wt fusion protein. Thus, two of the three IL-15 polypeptides evaluated, E46K and I50D, were diminished in/devoid of IL-15Rα-binding if used within a fusion protein of the present invention (FIG. 2A).

Example 3: Cytolytic Activity of Various Fusion Proteins Containing Different IL-15 Polypeptides In the next experiment the cytolytic activity of the fusion proteins tested in Example 2 was analyzed. To achieve that, NALM16 cells were incubated with the respective fusion proteins. Additionally, the peripheral blood mononuclear cells (PBMC) of a healthy volunteer were added to this culture. Usually such PBMC cells comprise lymphocytes, monocytes and macrophages. Some of the lymphocytes such as e.g. NK cells, CD8+ T cells or NK T cells express the β and common γ chain of the IL-2/IL-15 receptor to which IL-15 can bind (in addition to the IL-15 α chain). Thus, upon binding of the fusion proteins to both the NALM16 cells via the αCD19 (4G7) binding protein and to the βγ-positive cell via the IL-15 polypeptide the NALM16 (CD19 expressing) target cell can be killed.

To analyze this cytolytic activity, proliferation of the NALM16 target cells was assessed using a $^3$H-thymidine uptake assay after 2 days. In this regard, proliferation in the absence of fusion proteins and PBMC was defined as 100% proliferation, which means 0% inhibition of proliferation. Thus, the higher the amount of the inhibition of proliferation detected, the less proliferation takes place in this assay. Similarly, the smaller the amount of proliferation, the higher the cytolytic activity of the fusion protein.

As can be seen in FIG. 2B, the αCD19-IL15-wt and the αCD19-IL15-V49D fusion proteins performed both at about 80-85%, however, in the case of the mutant protein higher concentrations were required to achieve a comparable activity. The αCD19-IL15-I50D fusion protein resulted in an inhibition of about 60% of the proliferation comparable to that obtained by the parental αCD19-SDIE (4G7SDIE) antibody without an IL-15 moiety fused to it. Notably, the αCD19-IL15-E46K fusion protein together with the wild type protein provided the highest inhibition of proliferation (FIG. 2 B). Thus, the fusion protein containing the IL-15 polypeptide with the E46K amino acid substitution showed the highest cytolytic activity of all mutated proteins against CD19 expressing target cells and was thus used in subsequent experiments.

Example 4: Proliferation Induced by Different Fusion Proteins in NK92 Cells and PBMC Cells To test for the importance of a long linker (L) versus a short linker, proliferation of IL15 responsive cells was assessed using the 3H-thymidine uptake assay described in Example 3. Responsive cells were either NK92 cells (FIG. 3A) or PBMC (FIG. 3B). In fusion proteins comprising the short linker hIL-15 is directly linked to the CH3 domain via glycine-serine (short linker). The fusion proteins with the long linker comprise a 20 amino acid long linker (4-glycine 1-serine)4, which directly links hIL-15 to the CH3 domain.

Fusion proteins containing the long or the short linker were incubated with NK92 cells (FIG. 3A) or PBMC (FIG. 3B) cells for two days. Then, cells were pulsed with $^3$H thymidine, harvested at day 3 on filter mats and counted in a liquid scintillation counter.

In FIG. 3A, NK92 cells were incubated with different concentrations of the distinct fusion proteins as indicated (x-axis and Figure legend). NK92 cells are natural killer lymphoma cells, which do not express CD19 to which the αCD19 (4G7) binding protein binds (Gong et al. (1994) "Characterization of a human cell line (NK-92) with phenotypical and functional characteristics of activated natural killer cells" Leukemia; 8(4):652-8). Thus, this cell culture is devoid of target cells. By measuring proliferation $^3$H-thymidine counts as depicted on the y-axis (FIG. 3A), the ability of the fusion proteins to induce proliferation in effector cells in general is assessed.

The αCD19-IL15wt and αCD19-IL15wt-L (containing the long linker) resulted in a $^3$H thymidine count of about 25000, however in the case of the mutant protein higher concentrations are required to achieve a comparable activity. The αCD19-IL15-E46K provided for a lesser amount of proliferation in the cell culture (about 5000 counts of $^3$H thymidine). Notably, the fusion protein αCD19-IL15-E46K-L (containing the long linker) induced a proliferation of about 20000 counts (FIG. 3A). Thus, the fusion protein αCD19-IL15-E46K-L induced a higher proliferation/activation than the αCD19-IL15-E46K fusion protein.

Similar results were also obtained in FIG. 3B. Here, PBMC cells were incubated with different concentrations of the distinct fusion proteins as indicated (x-axis and Figure legend in FIG. 3B). Some PBMCs (such as B cells) also express CD19, which is detected by the 4G7 binding protein. Notably, a PBMC culture also comprises some potential effector cells such as e.g. NK cells. As in FIG. 3A, the proliferation was determined by $^3$H-thymidine counts as depicted on the y-axis (FIG. 3B).

In these experiments, the αCD19-IL15wt and αCD19-IL15wt-L (containing the long linker and wild-type (wt) IL-15 resulted in a $^3$H thymidine count of about 6000 and 12000, respectively. Again, the αCD19-IL15-E46K provided for a lesser extend of proliferation (about 4500 counts of $^3$H thymidine), while the fusion-protein αCD19-IL15-E46K-L (containing the long linker) resulted in a detected proliferation similar to the IL-15 wild-type fusion proteins (about 8500 counts; FIG. 3B). Thus in this experiment, the αCD19-IL15-E46K-L induced a higher proliferation/activation of cells than the αCD19-IL15-E46K fusion protein.

Example 5: Target Cell Restricted NK Cell Activation and Target Cell Killing

To evaluate target cell restricted activity of the generated fusion proteins, normal PBMC were incubated with wild-type IL-15 and mutated IL-15 polypeptides comprised in fusion proteins targeting the B cell associated CD19 antigen and the prostate specific membrane antigen (PSMA). Since B cells are present within PBMC cultures CD19 serves as a relevant target antigen in this setting, whereas PSMA is absent and thus irrelevant. PBMC were incubated for three days with the indicated fusion proteins (0.1 μg/ml) and were then analyzed by flow cytometry.

In FIG. 4A NK cell activation was assessed by measuring the numbers of CD56-positive cells expressing CD69 (CD56+/CD69+ double positive cells). CD69 is expressed by activated T and B cells, activated macrophages and NK cells, while CD56 is expressed by only NK cells. By selecting double positive cells (CD56+/CD69+), only activated NK cells are measured.

In FIG. 4A, cell counts are provided on the y-axis and the different fusion proteins utilized are depicted on the x-axis. In the control PBMC culture ("only PBMC") about 15000 cells expressed CD56 (CD56+) and about 1000 were double-positive for CD56 and CD69 (CD56+/CD69+). Application of the αCD19-SDIE (4G7 antibody comprising the SDIE mutations; 4G7-SDIE) did change the composition of the cells only marginally (to about 2500 activated NK cells). On the contrary, the number of activated NK cells within PBMC cultures massively increased as a result of the addition of the αCD19-SDIE-IL15wt-L fusion protein to approx. 20.000 activated NK cells). A less prominent but still remarkable increase in the number of activated NK cells (approx. 12.000) was observed with the αCD19-SDIE-IL15-E46K-L construct.

Additional experiments were conducted with fusion proteins targeting PSMA, which is not expressed by PBMC cells. Here, the addition of the PSMA-IL-15-E46K-L fusion protein did not activate NK cells. On the contrary, the application of the PSMA-IL-15wt construct also significantly increased the number of activated NK cells within the CD56-positive cell pool. From these results it can be concluded that NK cell activation by the constructs containing the IL-15 polypeptide with reduced affinity to IL-15Rα is target cell restricted, that is the fusion protein targeting CD19 but not that targeting PSMA activates NK cells and kills B cells. In contrast, upon application of fusion proteins comprising wild-type IL-15 (with normal affinity for IL-15Rα) target cell restricted activation of NK cell is less prominent or even absent. This is because wild type IL-15 is trans-presented by αIL15Rα and therefore does not require target cell binding to exert its activity.

In FIG. 4B B cell killing was assessed by measuring the numbers of CD20+ B cells. CD20 is exclusively expressed in B cells, thus the less B cells are present in the cell culture the more effective is the B cell killing of the fusion proteins comprising an αCD19 binding protein (4G7; anti-CD19 antibody).

Also in this experiment, a cell culture containing only PBMC cells without the addition of any fusion proteins served as a control. Here about 12000 CD20-positive (CD20+) B cells were counted. The addition of the αCD19-SDIE control resulted in a decrease of CD20-positive B cells (to about 5000 cells). Notably, the αCD19-15wt-L and αCD19-IL15-E46K-L fusion proteins resulted in the greatest decrease in CD20-positive B cells (about 2000 cells). On the contrary, the addition of a PSMA-IL15wt fusion protein showed a decrease to about 6000 cells. Notably, the PSMA-IL15-E46K-L fusion protein did not alter the number of CD20-positive B-cells in comparison to the "only PBMC" control.

Thus, the reduction of the number of CD20+ cells (B cell depletion) by the binding protein/IL-15 fusion proteins was more pronounced than that achieved by the Fc-optimized CD19 antibody (αCD19-SDIE; 4G7SDIE) alone (FIG. 4B). Furthermore, the PSMA directed fusion protein PSMA-IL15-E46K-L did not have any effect on the CD20-positive B cells and the PSMA IL15-wt fusion protein had a moderate effect. Thus, the target cell restricted B cell killing is most prominent using the IL-15-E46K-L fusion proteins, while fusion proteins comprising IL-15 wild-type showed a less prominent or even absent target cell restricted killing of B cells (FIG. 4 B).

In FIG. 4C NK-cell activation was assessed in B-cell depleted PBMC cultures. B cells were depleted with magnetic-activated cell sorting (MACS) using CD19 Micro-Beads (Miltenyi Biotec). As in FIG. 4B, for determination of cell numbers an equal amount of BD negative beads (negative beads from BD Biosciences) was added to each sample. During flow cytometry measurement of the same number of BD negative beads were acquired for all samples. This allowed the quantification of cells and direct comparison of cell numbers between different samples from one experiment. Since CD69 is expressed by activated T and B cells, activated macrophages and NK cells and CD56 is expressed by only NK cells, depletion of B cells restricted these cell pools to T cells and NK cells. Because CD19 expressing cells are depleted on these experiments the activity of the CD19 targeting fusion protein containing mutated IL-15 is strongly reduced but not of that containing wild type protein.

Conclusions: NK cell activation by the fusion proteins comprising the IL-15 polypeptides with a reduced affinity for IL-15Rα of wild-type IL-15 (SEQ ID NO: 1) are target cell restricted, that is the protein targeting CD19 but not that targeting PSMA activates NK cells and kills B cells. Consequently, NK cell activation by the CD19 targeting fusion protein was diminished if B cells were depleted from the PBMC (FIG. 4C).
a. NK cell activation by both fusion proteins containing wild-type IL-15 is not target cell restricted, that is both fusion proteins induce NK cell activation and at least some killing of B cells irrespective of the antigen targeted.
b. B cell depletion by the binding protein/IL-15 fusion proteins (with reduced affinity for IL-15Rα than wild-type IL-15) is more pronounced than that by the Fc-optimized CD19 antibody (αCD19-SDIE) alone (FIG. 4B).

Unless otherwise stated, the following terms used in this document, including the description and claims, have the definitions given below.

It is to be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Those skilled in the art will recognize, or be able to ascertain, using not more than routine experimentation, many equivalents to the specific embodiments of the invention described herein. Such equivalents are intended to be encompassed by the present invention.

Unless otherwise indicated, the term "at least" preceding a series of elements is to be understood to refer to every element in the series. Those skilled in the art will recognize, or be able to ascertain using no more than routine experimentation, many equivalents to the specific embodiments of the methods and uses described herein. Such equivalents are intended to be encompassed by the present invention.

Several documents are cited throughout the text of this disclosure. Each of the documents cited herein (including all patents, patent applications, scientific publications, manufacturer's specifications, instructions, etc.), whether supra or infra, are hereby incorporated by reference in their entirety. To the extent the material incorporated by reference contradicts or is inconsistent with this specification, the specification will supersede any such material. Nothing herein is to be construed as an admission that the invention is not entitled to antedate such disclosure by virtue of prior invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or" as used herein.

The word "about" as used herein refers to a value being within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. The term "about" is also used to indicate that the amount or value in question may be the value designated or some other value that is approximately the same. The phrase is intended to convey that similar values promote equivalent results or effects according to the invention. In this context "about" may refer to a range above and/or below of up to 10%. The word "about" refers in some embodiments to a range above and below a certain value that is up to 5%, such as up to up to 2%, up to 1%, or up to 0.5% above or below that value. In one embodiment "about" refers to a range up to 0.1% above and below a given value.

REFERENCE LIST

1. Beck A, Wurch T, Bailly C, Corvaia N. Strategies and challenges for the next generation of therapeutic antibodies. Nat Rev Immunol. 2010; 10:345-352.
2. Shinkawa T, Nakamura K, Yamane N, et al. The absence of fucose but not the presence of galactose or bisecting N-acetylglucosamine of human IgG1 complex-type oligosaccharides shows the critical role of enhancing antibody-dependent cellular cytotoxicity. J Biol Chem. 2003; 278:3466-3473.
3. Lazar G A, Dang W, Karki S, Vafa O, Peng J S, Hyun L, Chan C, Chung H S, Eivazi A, Yoder S C, Vielmetter J, Carmichael D F, Hayes R J, Dahiyat B I. Engineered antibody Fc variants with enhanced effector function. Proc Natl Acad Sci USA 2006; 103:4005-4010.
4. Oflazoglu E, Audoly LP. Evolution of anti-CD20 monoclonal antibody therapeutics in oncology. MAbs. 2010; 2:14-19.
5. Valentin Goede, M.D., Kirsten Fischer, M.D., Raymonde Busch, M.S., Anja Engelke, M.D., Barbara Eichhorst, M.D., Clemens M. Wendtner, M.D., Tatiana Chagorova, M.D., Javier de la Serna, M.D., Marie-Sarah Dilhuydy, M.D., Thomas Ilimer, M.D., Stephen Opat, M.D., Carolyn J. Owen, M.D., Olga Samoylova, M.D., Karl-Anton Kreuzer, M.D., Stephan Stilgenbauer, M.D., Hartmut Dohner, M.D., Anton W. Langerak, Ph.D., Matthias Ritgen, M.D., Michael Kneba, Elina Asikanius, M.Sc., Kathryn Humphrey, B.Sc., Michael Wenger, M.D., and Michael Hallek, M.D. Obinutuzumab plus Chlorambucil in Patients with CLL and Coexisting Conditions. N Engt J Med 2014; 370:1101-1110.
6. Horton H M, Bernett M J, Pong E, Peipp M, Karki S, Chu S Y, Richards J O, Vostiar I, Joyce P F, Repp R, Desjarlais J R, Zhukovsky E A. Potent in vitro and in vivo activity of an Fc-engineered anti-CD19 monoclonal antibody against lymphoma and leukemia. Cancer Res 2008; 68:8049-8057.
7. Foyil K V, Bartlett N L. Anti-CD30 Antibodies for Hodgkin lymphoma. Curr Hematol Malig Rep 2010; 5:140-147.
8. Ring A M, Lin J X, Feng D, Mitra S, Rickert M, Bowman G R, Pande V S, Li P, Moraga I, Spolski R, Ozkan E, Leonard W J, Garcia K C. Mechanistic and structural insight into the functional dichotomy between IL-2 and IL-15. Nat Immunof 2012; 13:1187-1195.
9. Waldmann T A. The biology of interleukin-2 and interleukin-15: implications for cancer therapy and vaccine design. Nat Rev Immunol 2006; 6:595-601.
10. Perna K, De Angelis B, Pagliara D, Hasan S T, Zhang L, Mahendravada A, Heslop H E, Brenner M K, Rooney C M, Dotti G. Savoldo B. Interleukin 15 provides relief to CTLs from regulatory T cell-mediated inhibition: implications for adoptive T cell-based therapies for lymphoma. Clin Cancer Res 2013; 19:106-117.
11. Liu R B, Engels B, Schreiber K, Ciszewski C, Schietinger A, Schreiber H, Jabri B. IL-15 in tumor microenvironment causes rejection of large established tumors by T cells in a noncognate T cell receptor-dependent manner. Proc Natl Acad Sci USA 2013; 110:8158-8163.
12. List T, Neri D. Immunocytokines: a review of molecules in clinical development for cancer therapy. Clin Pharmacol 2013; 5:29-45.
13. Gillies S D, Reilly E B, Lo K M. Reisfeld R A. Antibody-targeted interleukin 2 stimulates Tcell killing of autologous tumor cells. Proc Nati Acad Sci USA 1992; 89:1428-1432.
14. Albertini M R, Hank J A, Gadbaw 8, Kostlevy J, Haldeman J, Schalch H, Gan J, Kim K, Eickhoff J, Gillies S D, Sondel P M. Phase II trial of hu14.18-11.2 for patients with metastatic melanoma. Cancer Immunol Immunother 2012; 61:2261-2271.
15. Ribas A, Kirkwood J M, Atkins M B, Whiteside T L, Gooding W, Kovar A, Gillies S D, Kashala O, Morse M A. Phase 1/11 open-label study of the biologic effects of the interleukin-2 immunocytokine EMD 273063 (hu14.18-IL2) in patients with metastatic malignant melanoma. J Transl Med 2009; 7:68.
16. Bessard A, Sole V, Bouchaud G, Quernener A. Jacques Y. High antitumor activity of RLI, an interleukin-15 (1L-15)-1L-15 receptor alpha fusion protein, in metastatic melanoma and colorectal cancer. Mol Cancer Ther 2009; 8:2736-2745.
17. Vincent M, Bessard A, Cochonneau D, Teppaz G, Sold V, Mailiasson M, Birkld S, Garrigue-Antar L, Quernener A, Jacques Y. Tumor targeting of the 1L-15 superagonist RLI by an anti-GD2 antibody strongly enhances its antitumor potency. Int J Cancer 2013; 133:757-765.
18. Kermer V, Baum V, Hornig N, Kontermann R E, Muller D. An antibody fusion protein for cancer immunotherapy mimicking IL-15 trans-presentation at the tumor site. Mol Cancer Ther. 2012; 11:1279-1288.
19. Rubinstein M P, Kovar M, Purton J F, Cho J H, Boyman O, Surh C D, Sprent J. Converting IL-15 to a superagonist by binding to soluble IL-15R{alpha}. Proc Natl Acad Sci USA 2006; 103:9166-9171.
20. Bernard J, Harb C, Mortier E, Qudmener A, Meloen R H, Vermot-Desroches C, Wijdeness J, van Dijken P, Grotzinger J, Slootstra J W, Plet A, Jacques Y. Identification of an interleukin-15alpha receptor-binding site an human interleukin-15. J Biol Chem 2004; 279:24313-24322.
21. Quemener A, Bernard J, Mortier E, Plet A, Jacques Y, Tran V. Docking of human interleukin-15 to its specific receptor alpha chain: correlation between molecular modeling and mutagenesis experimental data. Proteins 2006; 65:623-636
22. Hofmann M, Grosse-Hovest L, Nubling T, Pyz E. Bamberg M L, Aulwurm S, Buhring H J, Schwartz K, Haen S P, Schilbach K, Rammensee H G, Salih H R, Jung G. Generation, selection and preclinical characterization of an Fc-optimized FLT3 antibody for the treatment of myeloid leukemia. Leukemia 2012; 26:1228-1237.
23. Holt L J, Herring C, Jespers L S, Woolven B P, Tomlinson I M. Domain antibodies: proteins for therapy. *Trends Biotechnol.* 2003 November; 21(11):484-90
24. III C R, Gonzales J N, Houtz E K, Ludwig J R, Melcher E D, Hale J E, Pourmand R, Keivens V M, Myers L, Beidler K, Stuart P, Cheng S, Radhakrishnan R. Design and construction of a hybrid immunoglobulin domain with properties of both heavy and light chain variable regions. Protein Eng. 1997 August; 10(8):949-57
25. Martin F, Toniatti C, Salvati A L, Venturini S, Ciliberto G, Cortese R, Sollazzo M. The affinity-selection of a minibody polypeptide inhibitor of human interleukin-6. EMBO J. 1994 Nov. 15; 13(22):5303-9
26. Traunecker A, Lanzavecchia A, Karjalainen K. Bispecific single chain molecules (Janusins) target cytotoxic lymphocytes on HIV infected cells. EMBO J. 1991 December; 10(12):3655-9
27. Traunecker A, Lanzavecchia A, Karjalainen K. Janusin: new molecular design for bispecific reagents. Int J Cancer Suppl. 1992; 7:51-2
28. Silverman J, Liu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P. Multivalent avimer proteins evolved by exon shuffling of a family of human receptor domains. Nat Biotechnol. 2005 December; 23(12):1556-61. Epub 2005 Nov. 20
29. Silverman J, Liu Q, Bakker A, To W, Duguay A, Alba B M, Smith R, Rivas A, Li P, Le H, Whitehorn E, Moore K W, Swimmer C, Perlroth V, Vogt M, Kolkman J, Stemmer W P. Multivalent avimer proteins evolved by exon shuffling of a family of human receptor domains. *Nat Biotechnol.* 2005 December; 23(12):1556-61. Epub 2005 Nov. 20.
30. Lamerisa et al. "Bispecific antibody platforms for cancer immunotherapy" *Crit Rev Oncol Hematol.* 2014; S1040-8428(14)00135-8
31. Altschul, Nucl. Acids Res. 25 (1997), 3389-3402
32. Chen et al. "Fusion protein linkers: property, design and functionality" Adv Drug Deliv Rev; 2013; 65(10):1357-69
33. Gennaro, A. L. and Gennaro, A. R. (2000) Remington: The Science and Practice of Pharmacy, 20th Ed., Lippincott Williams & Wilkins, Philadelphia, Pa.
34. J. S. Patton et al. The lungs as a portal of entry for systemic drug delivery. Proc. Amer. Thoracic Soc. 2004 Vol. 1 pages 338-344
35. Jung et al. Local immunotherapy of glioma patients with a combination of 2 bispecific antibody fragments and resting autologous lymphocytes: evidence for in situ t-cell activation and therapeutic efficacy Int J Cancer January 2001; 15; 91(2):225-30,
36. Natsume A, Niwa R, Satoh M. "Improving effector functions of antibodies for cancer treatment: Enhancing ADCC and CDC" Drug Des Devel Ther. 2009; 3:7-16.
37. Gong J H, Maki G, Klingemann H G. "Characterization of a human cell line (NK-92) with phenotypical and functional characteristics of activated natural killer cells" Leukemia; 1994, 8(4):652-8
38. Altschul, J. Mol. Evol. 36 (1993), 290-300
39. Altschul, J. Mol. Biol. 215 (1990), 403-410
40. Kontermann (2012) "Dual targeting strategies with bispecific antibodies" Landes Bioscience mAbs Vol. 4, Issue 2 182-197
41. Kaspar M, Trachsel E, Neri D. "The antibody-mediated targeted delivery of interleukin-15 and GM-CSF to the tumor neovasculature inhibits tumor growth and metastasis." Cancer Res. 2007 May 15; 67(10):4940-8.
42. Conlon K C, Lugli E1, Welles H C, Rosenberg S A, Fojo A T, Morris J C, Fleisher T A, Dubois S P, Perera L P, Stewart D M, Goldman C K, Bryant B R, Decker J M, Chen J, Worthy T A, Figg W D Sr, Peer C J, Sneller M C, Lane H C, Yovandich J L, Creekmore S P, Roederer M, Waldmann T A "Redistribution, hyperproliferation, activation of natural killer cells and CD8 T cells, and cytokine production during first-in-human clinical trial of recombinant human interleukin-15 in patients with cancer." J Clin Oncol. 2015 Jan. 1; 33(1):74-82.
43. Navid et al, Immune Therapies for Neuroblastoma, Cancer Biol Ther. 2009 May; 8(10): 874-882,

---

What is claimed is:

1. A fusion protein comprising
a) a binding protein comprising at least one binding site, wherein the binding site binds to an antigen associated with a target cell; and
b) an IL-15 polypeptide, wherein the IL-15 polypeptide comprises at least one amino acid substitution at one or more positions corresponding to position(s) 92, 94, 95, 97, 98, 114, and/or 115 of the amino acid sequence shown in SEQ ID NO:1
thereby having a reduced affinity for IL-15Rα compared to the affinity of wild-type IL-15 of SEQ ID NO: 1 (Uniprot number: P40933-1).

2. The fusion protein of claim 1, wherein the binding protein is selected from the group consisting of an antibody, a divalent antibody fragment, a monovalent antibody fragment, or a proteinaceous binding molecule with antibody-like binding properties.

3. The fusion protein of claim 2, wherein the binding protein is an antibody, a divalent antibody fragment, or a monovalent antibody fragment which is Fc optimized.

4. The fusion protein of claim 1, wherein the target cell expresses a tumor associated antigen (TAA) and/or an antigen associated with autoimmune diseases.

5. The fusion protein of claim 4, wherein the TAA is selected from the group consisting of CD19, CD20, CD10, CD21, CD22, CD25, CD30, CD33, CD34, CD37, CD38, CD44v6, CD45, CDw52, Fms-like tyrosine kinase 3 (FLT-3, CD135), c-Kit (CD117), CSF1R, (CD115), CD123, CD133, PDGFR-α (CD140a), PDGFR-β (CD140b), chondroitin sulfate proteoglycan 4 (CSPG4, melanoma-associated chondroitin sulfate proteoglycan), Muc-1, EGFR, de2-7-EGFR, EGFRvIII, Folate blocking protein, Her2neu, Her3, PSMA, PSCA, PSA, TAG-72, HLA-DR, IGFR, CD133, IL3R, fibroblast activating protein (FAP), Carboanhydrase IX (MN/CA IX), Carcinoembryonic antigen (CEA), EpCAM, CDCP1, Derlin1, Tenascin, frizzled 1-10, the vascular antigens VEGFR2 (KDR/FLK1), VEGFR3 (FLT4, CD309), Endoglin, CLEC14, Tem1-8, Tie2, mesothelin, epithelial glycoprotein 2 (EGP2), epithelial glycoprotein 40 (EGP40), cancer antigen 72-4 (CA72-4), interleukin 13 receptor alpha-2 subunit, IL13Rα2, Ig kappa light chain (κ), GD3- ganglioside (GD3), GD2-ganglioside (GD2), acetylated variants of GD2 and GD3, CD171, NCAM, alpha folate receptor (αFR), Lewis (Y), fetal acetylcholine receptor (FAR), avian erythroblastic leukemia viral oncogene homolog 3 (ERBB3), avian erythroblastic leukemia viral oncogene homolog 4 (ERBB4), avian erythroblastic leukemia viral oncogene homolog 2 (ERBB2), hepatocyte growth factor receptor (HGFR/c-Met), claudin 18.2, claudin 3, claudin 4, claudin 1, claudin 12, claudin 2, claudin 5, claudin 8, claudin 7, claudin 6, membrane bound CEA, Robo4, CD138, tenascin and the extra domain-B of fibronectin.

6. The fusion protein of claim 4, wherein the target cell expresses an antigen associated with autoimmune diseases, which antigen is selected from the group consisting of CD20, CD22, CD52 and TNFR, CD19, CD25, CD40.

7. The fusion protein of claim 1, wherein the target cell is a tumor/cancer cell and/or a B cell.

8. The fusion protein of claim 1, wherein the IL-15 polypeptide comprises at least one amino acid substitution at one or more positions corresponding to position(s) 94, 97, 98, 114 and/or 115 of the amino acid sequence shown in SEQ ID NO:1.

9. The fusion protein of claim 1, wherein the at least one amino acid substitution is selected from the group consisting of L92D, E94K, L95D, V97D, I98D, L114D, L114E, I115D, I115E.

10. The fusion protein of claim 1, wherein the IL-15 polypeptide does not bind to IL-15Rα.

11. The fusion protein of claim 1, wherein the IL-15 polypeptide binds to IL-2/IL-15Rβγ.

12. The fusion protein of claim 1, wherein the IL-15 polypeptide comprises at least an amino acid sequence as shown in SEQ ID NO: 4, which comprises at least one amino acid substitution at one or more positions at least one amino acid substitution at one or more positions corresponding to position(s) 44, 46, 47, 49, 50, 66, and/or 67 of the amino acid sequence shown in SEQ ID NO: 4.

13. The fusion protein of claim 1, wherein the fusion protein further comprises a linker.

14. A kit comprising the fusion protein of claim 1.

15. The kit of claim 14, wherein the kit further comprises
a) one or more buffer(s);
b) one or more protocol(s).

* * * * *

SEQUENCE LISTING

```
<160> NUMBER OF SEQ ID NOS: 44

<210> SEQ ID NO 1
<211> LENGTH: 162
<212> TYPE: PRT
<213> ORGANISM: Artificial Sequence
<220> FEATURE:
<223> OTHER INFORMATION: Synthesized IL-15

<400> SEQUENCE: 1

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
        50                  55                  60

Gln Ser Met His Ile Asp Ala Thr Leu Tyr Thr Glu Ser Asp Val His
65                  70                  75                  80
```

```
Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 2
<211> LENGTH: 9
<212> TYPE: PRT
<213> ORGANISM: Artificial Sequence
<220> FEATURE:
<223> OTHER INFORMATION: Synthesized sequence important for alpha
      binding of IL-15

<400> SEQUENCE: 2

Leu Leu Glu Leu Gln Val Ile Ser Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Synthesized sequence important for alpha
      binding of IL-15

<400> SEQUENCE: 3

Glu Asn Leu Ile Ile
1               5

<210> SEQ ID NO 4
<211> LENGTH: 114
<212> TYPE: PRT
<213> ORGANISM: Artificial Sequence
<220> FEATURE:
<223> OTHER INFORMATION: Synthesized IL-15 fragment

<400> SEQUENCE: 4

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

-continued

```
<210> SEQ ID NO 5
<211> LENGTH: 121
<212> TYPE: PRT
<213> ORGANISM: Artificial Sequence
<220> FEATURE:
<223> OTHER INFORMATION: Synthesized Anti-CD19 single variable domain VH
      (clone 4G7)

<400> SEQUENCE: 5

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

Gln Gly Thr Thr Leu Thr Val Ser Ser
        115                 120

<210> SEQ ID NO 6
<211> LENGTH: 112
<212> TYPE: PRT
<213> ORGANISM: Artificial Sequence
<220> FEATURE:
<223> OTHER INFORMATION: Synthesized Anti-CD19 single variable domain VL
      (clone 4G7)

<400> SEQUENCE: 6

Asp Ile Val Met Thr Gln Ala Ala Pro Ser Ile Pro Val Thr Pro Gly
1               5                   10                  15

Glu Ser Val Ser Ile Ser Cys Arg Ser Ser Lys Ser Leu Leu Asn Ser
                20                  25                  30

Asn Gly Asn Thr Tyr Leu Tyr Trp Phe Leu Gln Arg Pro Gly Gln Ser
            35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

<210> SEQ ID NO 7
<211> LENGTH: 123
<212> TYPE: PRT
<213> ORGANISM: Artificial Sequence
<220> FEATURE:
<223> OTHER INFORMATION: Synthesized anti-FLT3 single variable domain VH
      (clone BV10)

<400> SEQUENCE: 7

Gln Val Gln Leu Lys Gln Ser Gly Pro Gly Leu Val Gln Pro Ser Gln
1               5                   10                  15
```

```
Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser
        115                 120
```

<210> SEQ ID NO 8
<211> LENGTH: 113
<212> TYPE: PRT
<213> ORGANISM: Artificial Sequence
<220> FEATURE:
<223> OTHER INFORMATION: Synthesized anti-FLT3 single variable domain VL
      (clone BV10)

<400> SEQUENCE: 8

```
Asp Ile Val Met Thr Gln Ser Pro Ser Ser Leu Ser Val Ser Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Met Ala Trp Tyr Gln Gln Lys Pro Gly Gln
        35                  40                  45

Pro Pro Lys Leu Leu Ile Tyr Gly Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
            100                 105                 110

Lys
```

<210> SEQ ID NO 9
<211> LENGTH: 118
<212> TYPE: PRT
<213> ORGANISM: Artificial Sequence
<220> FEATURE:
<223> OTHER INFORMATION: Synthesized anti-FLT3 chimeric single variable
      domain heavy chain (clone 4G8)VH

<400> SEQUENCE: 9

```
Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
            20                  25                  30

Trp Met His Trp Val Arg Gln Arg Pro Gly His Gly Leu Glu Trp Ile
        35                  40                  45

Gly Glu Ile Asp Pro Ser Asp Ser Tyr Lys Asp Tyr Asn Gln Lys Phe
50                  55                  60
```

```
Lys Asp Lys Ala Thr Leu Thr Val Asp Arg Ser Ser Asn Thr Ala Tyr
 65                  70                  75                  80

Met His Leu Ser Ser Leu Thr Ser Asp Asp Ser Ala Val Tyr Tyr Cys
                 85                  90                  95

Ala Arg Ala Ile Thr Thr Thr Pro Phe Asp Phe Trp Gly Gln Gly Thr
            100                 105                 110

Thr Leu Thr Val Ser Ser
            115
```

<210> SEQ ID NO 10
<211> LENGTH: 107
<212> TYPE: PRT
<213> ORGANISM: Artificial Sequence
<220> FEATURE:
<223> OTHER INFORMATION: Synthesized anti-FLT3 chimeric single variable
      domain light chain (clone 4G8) VL

<400> SEQUENCE: 10

```
Asp Ile Val Leu Thr Gln Ser Pro Ala Thr Leu Ser Val Thr Pro Gly
 1               5                  10                  15

Asp Ser Val Ser Leu Ser Cys Arg Ala Ser Gln Ser Ile Ser Asn Asn
             20                  25                  30

Leu His Trp Tyr Gln Gln Lys Ser His Glu Ser Pro Arg Leu Leu Ile
         35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Val Tyr Phe Cys Gln Gln Ser Asn Thr Trp Pro Tyr
                 85                  90                  95

Thr Phe Gly Gly Gly Thr Lys Leu Glu Ile Lys
            100                 105
```

<210> SEQ ID NO 11
<211> LENGTH: 115
<212> TYPE: PRT
<213> ORGANISM: Artificial Sequence
<220> FEATURE:
<223> OTHER INFORMATION: Synthesized anti-PSMA single variable domain
      heavy chain (clone J591) VH

<400> SEQUENCE: 11

```
Glu Val Gln Leu Gln Gln Ser Gly Pro Glu Leu Val Lys Pro Gly Thr
 1               5                  10                  15

Ser Val Arg Ile Ser Cys Lys Thr Ser Gly Tyr Thr Phe Thr Glu Tyr
             20                  25                  30

Thr Ile His Trp Val Lys Gln Ser His Gly Lys Ser Leu Glu Trp Ile
         35                  40                  45

Gly Asn Ile Asn Pro Asn Asn Gly Gly Thr Thr Tyr Asn Gln Lys Phe
 50                  55                  60

Glu Asp Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Ala Gly Trp Asn Phe Asp Tyr Trp Gly Gln Gly Thr Thr Leu Thr
            100                 105                 110

Val Ser Ser
        115
```

-continued

```
<210> SEQ ID NO 12
<211> LENGTH: 107
<212> TYPE: PRT
<213> ORGANISM: Artificial Sequence
<220> FEATURE:
<223> OTHER INFORMATION: Synthesized anti-PSMA single variable domain
      light chain (clone J591) VL

<400> SEQUENCE: 12

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys
            100                 105

<210> SEQ ID NO 13
<211> LENGTH: 5
<212> TYPE: PRT
<213> ORGANISM: Artificial Sequence
<220> FEATURE:
<223> OTHER INFORMATION: Synthesized linker

<400> SEQUENCE: 13

Gly Gly Gly Gly Ser
1               5

<210> SEQ ID NO 14
<211> LENGTH: 18
<212> TYPE: PRT
<213> ORGANISM: Artificial Sequence
<220> FEATURE:
<223> OTHER INFORMATION: Synthesized linker

<400> SEQUENCE: 14

Lys Glu Ser Gly Ser Val Ser Ser Glu Gln Leu Ala Gln Phe Arg Ser
1               5                   10                  15

Leu Asp

<210> SEQ ID NO 15
<211> LENGTH: 14
<212> TYPE: PRT
<213> ORGANISM: Artificial Sequence
<220> FEATURE:
<223> OTHER INFORMATION: Synthesized linker

<400> SEQUENCE: 15

Glu Gly Lys Ser Ser Gly Ser Gly Ser Glu Ser Lys Ser Thr
1               5                   10

<210> SEQ ID NO 16
<211> LENGTH: 8
<212> TYPE: PRT
<213> ORGANISM: Artificial Sequence
<220> FEATURE:
```

```
<223> OTHER INFORMATION: Synthesized linker

<400> SEQUENCE: 16

Gly Gly Gly Gly Gly Gly Gly Gly
1               5

<210> SEQ ID NO 17
<211> LENGTH: 12
<212> TYPE: PRT
<213> ORGANISM: Artificial Sequence
<220> FEATURE:
<223> OTHER INFORMATION: Synthesized linker

<400> SEQUENCE: 17

Gly Ser Ala Gly Ser Ala Ala Gly Ser Gly Glu Phe
1               5                   10

<210> SEQ ID NO 18
<211> LENGTH: 6
<212> TYPE: PRT
<213> ORGANISM: Artificial Sequence
<220> FEATURE:
<223> OTHER INFORMATION: Synthesized linker

<400> SEQUENCE: 18

Gly Gly Gly Gly Gly Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Synthesized linker

<400> SEQUENCE: 19

Ala Glu Ala Ala Ala Lys Ala
1               5

<210> SEQ ID NO 20
<211> LENGTH: 14
<212> TYPE: PRT
<213> ORGANISM: Artificial Sequence
<220> FEATURE:
<223> OTHER INFORMATION: Synthesized linker

<400> SEQUENCE: 20

Ala Pro Ala Pro Ala Pro Ala Pro Ala Pro Ala Pro Ala Pro
1               5                   10

<210> SEQ ID NO 21
<211> LENGTH: 20
<212> TYPE: PRT
<213> ORGANISM: Artificial Sequence
<220> FEATURE:
<223> OTHER INFORMATION: Synthesized linker

<400> SEQUENCE: 21

Leu Glu Ala Gly Cys Lys Asn Phe Phe Pro Arg Ser Phe Thr Ser Cys
1               5                   10                  15

Gly Ser Leu Glu
            20

<210> SEQ ID NO 22
<211> LENGTH: 4
<212> TYPE: PRT
```

```
<213> ORGANISM: Artificial Sequence
<220> FEATURE:
<223> OTHER INFORMATION: Synthesized linker

<400> SEQUENCE: 22

Gly Ser Ser Thr
1

<210> SEQ ID NO 23
<211> LENGTH: 12
<212> TYPE: PRT
<213> ORGANISM: Artificial Sequence
<220> FEATURE:
<223> OTHER INFORMATION: Synthesized linker

<400> SEQUENCE: 23

Cys Arg Arg Arg Arg Arg Glu Ala Glu Ala Cys
1               5                   10

<210> SEQ ID NO 24
<211> LENGTH: 20
<212> TYPE: PRT
<213> ORGANISM: Artificial Sequence
<220> FEATURE:
<223> OTHER INFORMATION: Synthesized linker

<400> SEQUENCE: 24

Gly Gly Gly Gly Ser Gly Gly Gly Ser Gly Gly Gly Ser Gly
1               5                   10                  15

Gly Gly Gly Ser
            20

<210> SEQ ID NO 25
<211> LENGTH: 117
<212> TYPE: PRT
<213> ORGANISM: Artificial Sequence
<220> FEATURE:
<223> OTHER INFORMATION: Synthesized anti-endoglin single variable
      domain heavy chain (clone Kro23) VH

<400> SEQUENCE: 25

Glu Val Gln Leu Gln Gln Ser Gly Ala Asp Leu Val Arg Ser Gly Ala
1               5                   10                  15

Ala Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Asp Lys Ala Thr Met Thr Ala Asp Ser Ser Ser Asn Thr Ala Tyr
65                  70                  75                  80

Leu Gln Leu Asn Ser Leu Thr Ser Glu Asp Thr Gly Val Tyr Tyr Cys
                85                  90                  95

Asn Thr Arg Tyr Gly Thr Ser Ser Ala Cys Trp Gly Gln Gly Thr Thr
            100                 105                 110

Leu Thr Val Ser Ser
        115

<210> SEQ ID NO 26
<211> LENGTH: 107
<212> TYPE: PRT
<213> ORGANISM: Artificial Sequence
<220> FEATURE:
```

<223> OTHER INFORMATION: Synthesized anti-endoglin single variable
       domain light chain (clone Kro23) VL

<400> SEQUENCE: 26

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Arg Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asn Pro Leu Thr
                85                  90                  95

Phe Gly Ala Gly Thr Lys Leu Glu Leu Lys Arg
            100                 105

<210> SEQ ID NO 27
<211> LENGTH: 582
<212> TYPE: PRT
<213> ORGANISM: Artificial Sequence
<220> FEATURE:
<223> OTHER INFORMATION: Synthesized fusion protein of anti-endoglin IgG
      (Kro23) heavy chain with SDIE modificaion and IL15 mutant

<400> SEQUENCE: 27

Glu Val Gln Leu Gln Gln Ser Gly Ala Asp Leu Val Arg Ser Gly Ala
1               5                   10                  15

Ala Val Lys Leu Ser Cys Thr Ala Ser Gly Phe Asn Ile Lys Asp Tyr
            20                  25                  30

Tyr Leu His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Asp Lys Ala Thr Met Thr Ala Asp Ser Ser Ser Asn Thr Ala Tyr
65                  70                  75                  80

Leu Gln Leu Asn Ser Leu Thr Ser Glu Asp Thr Gly Val Tyr Tyr Cys
                85                  90                  95

Asn Thr Arg Tyr Gly Thr Ser Ser Ala Cys Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Asp Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Glu Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly Lys Ser
    435                 440                 445

Gly Gly Gly Gly Ser Gly Gly Gly Ser Gly Gly Gly Gly Ser Gly
450                 455                 460

Gly Gly Gly Ser Asn Trp Val Asn Val Ile Ser Asp Leu Lys Lys Ile
465                 470                 475                 480

Glu Asp Leu Ile Gln Ser Met His Ile Asp Ala Thr Leu Tyr Thr Glu
            485                 490                 495

Ser Asp Val His Pro Ser Cys Lys Val Thr Ala Met Lys Cys Phe Leu
        500                 505                 510

Leu Lys Leu Gln Val Ile Ser Leu Glu Ser Gly Asp Ala Ser Ile His
    515                 520                 525

Asp Thr Val Glu Asn Leu Ile Ile Leu Ala Asn Asn Ser Leu Ser Ser
530                 535                 540

Asn Gly Asn Val Thr Glu Ser Gly Cys Lys Glu Cys Glu Glu Leu Glu
545                 550                 555                 560

Glu Lys Asn Ile Lys Glu Phe Leu Gln Ser Phe Val His Ile Val Gln
            565                 570                 575

Met Phe Ile Asn Thr Ser
        580

<210> SEQ ID NO 28
<211> LENGTH: 213
<212> TYPE: PRT
<213> ORGANISM: Artificial sequence
<220> FEATURE:
<223> OTHER INFORMATION: Synthesized light chain of anti-endoglin
      antibody Kro23

<400> SEQUENCE: 28

```
Gln Ile Val Leu Thr Gln Ser Pro Ala Leu Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Arg Pro Arg Ser Ser Pro Lys Pro Trp Ile Tyr
                35                  40                  45

Leu Thr Ser Asn Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Arg Thr Val Ala Ala Pro
            100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 29
<211> LENGTH: 567
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 wild type with
      short linker

<400> SEQUENCE: 29

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
                35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
                115                 120                 125
```

```
Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Ser Asn Trp Val Asn Val Ile Ser Asp Leu Lys Lys
450                 455                 460

Ile Glu Asp Leu Ile Gln Ser Met His Ile Asp Ala Thr Leu Tyr Thr
465                 470                 475                 480

Glu Ser Asp Val His Pro Ser Cys Lys Val Thr Ala Met Lys Cys Phe
                485                 490                 495

Leu Leu Glu Leu Gln Val Ile Ser Leu Glu Ser Gly Asp Ala Ser Ile
                500                 505                 510

His Asp Thr Val Glu Asn Leu Ile Ile Leu Ala Asn Asn Ser Leu Ser
            515                 520                 525

Ser Asn Gly Asn Val Thr Glu Ser Gly Cys Lys Glu Cys Glu Glu Leu
530                 535                 540

Glu Glu Lys Asn Ile Lys Glu Phe Leu Gln Ser Phe Val His Ile Val
```

```
                545                 550                 555                 560
Gln Met Phe Ile Asn Thr Ser
                565

<210> SEQ ID NO 30
<211> LENGTH: 567
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 (E46K) mutant
      with short linker

<400> SEQUENCE: 30

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Glu
                325                 330                 335
```

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Ser Asn Trp Val Asn Val Ile Ser Asp Leu Lys Lys
            450                 455                 460

Ile Glu Asp Leu Ile Gln Ser Met His Ile Asp Ala Thr Leu Tyr Thr
465                 470                 475                 480

Glu Ser Asp Val His Pro Ser Cys Lys Val Thr Ala Met Lys Cys Phe
                485                 490                 495

Leu Leu Lys Leu Gln Val Ile Ser Leu Glu Ser Gly Asp Ala Ser Ile
            500                 505                 510

His Asp Thr Val Glu Asn Leu Ile Ile Leu Ala Asn Asn Ser Leu Ser
            515                 520                 525

Ser Asn Gly Asn Val Thr Glu Ser Gly Cys Lys Glu Cys Glu Glu Leu
530                 535                 540

Glu Glu Lys Asn Ile Lys Glu Phe Leu Gln Ser Phe Val His Ile Val
545                 550                 555                 560

Gln Met Phe Ile Asn Thr Ser
                565

<210> SEQ ID NO 31
<211> LENGTH: 567
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 (V49D) mutant
      with short linker

<400> SEQUENCE: 31

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

-continued

Gln Gly Thr Thr Leu Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Ser Asn Trp Val Asn Val Ile Ser Asp Leu Lys Lys
    450                 455                 460

Ile Glu Asp Leu Ile Gln Ser Met His Ile Asp Ala Thr Leu Tyr Thr
465                 470                 475                 480

Glu Ser Asp Val His Pro Ser Cys Lys Val Thr Ala Met Lys Cys Phe
                485                 490                 495

Leu Leu Glu Leu Gln Asp Ile Ser Leu Glu Ser Gly Asp Ala Ser Ile
            500                 505                 510

His Asp Thr Val Glu Asn Leu Ile Ile Leu Ala Asn Asn Ser Leu Ser
        515                 520                 525

Ser Asn Gly Asn Val Thr Glu Ser Gly Cys Lys Glu Cys Glu Glu Leu

-continued

```
                530                 535                 540
Glu Glu Lys Asn Ile Lys Glu Phe Leu Gln Ser Phe Val His Ile Val
545                 550                 555                 560

Gln Met Phe Ile Asn Thr Ser
                565

<210> SEQ ID NO 32
<211> LENGTH: 567
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 (I50D) mutant
      with short linker

<400> SEQUENCE: 32

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

Lys Glu Tyr Lys Cys Lys Val Ser Asn Lys Ala Leu Pro Ala Pro Glu
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Ser Asn Trp Val Asn Val Ile Ser Asp Leu Lys Lys
    450                 455                 460

Ile Glu Asp Leu Ile Gln Ser Met His Ile Asp Ala Thr Leu Tyr Thr
465                 470                 475                 480

Glu Ser Asp Val His Pro Ser Cys Lys Val Thr Ala Met Lys Cys Phe
                485                 490                 495

Leu Leu Glu Leu Gln Val Asp Ser Leu Glu Ser Gly Asp Ala Ser Ile
            500                 505                 510

His Asp Thr Val Glu Asn Leu Ile Ile Leu Ala Asn Asn Ser Leu Ser
        515                 520                 525

Ser Asn Gly Asn Val Thr Glu Ser Gly Cys Lys Glu Cys Glu Glu Leu
    530                 535                 540

Glu Glu Lys Asn Ile Lys Glu Phe Leu Gln Ser Phe Val His Ile Val
545                 550                 555                 560

Gln Met Phe Ile Asn Thr Ser
                565

<210> SEQ ID NO 33
<211> LENGTH: 586
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 wild type with
      long linker

<400> SEQUENCE: 33

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

```
Ala Arg Gly Thr Tyr Tyr Gly Ser Arg Val Phe Asp Tyr Trp Gly
            100                 105                 110
Gln Gly Thr Thr Leu Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Asp Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Glu
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Ser Gly Gly Gly Gly Ser Gly Gly Gly Gly Ser Gly Gly
    450                 455                 460
Gly Gly Ser Gly Gly Gly Gly Ser Asn Trp Val Asn Val Ile Ser Asp
465                 470                 475                 480
Leu Lys Lys Ile Glu Asp Leu Ile Gln Ser Met His Ile Asp Ala Thr
                485                 490                 495
Leu Tyr Thr Glu Ser Asp Val His Pro Ser Cys Lys Val Thr Ala Met
            500                 505                 510
Lys Cys Phe Leu Leu Glu Leu Gln Val Ile Ser Leu Glu Ser Gly Asp
```

```
                    515                 520                 525

Ala Ser Ile His Asp Thr Val Glu Asn Leu Ile Ile Leu Ala Asn Asn
        530                 535                 540

Ser Leu Ser Ser Asn Gly Asn Val Thr Glu Ser Gly Cys Lys Glu Cys
545                 550                 555                 560

Glu Glu Leu Glu Glu Lys Asn Ile Lys Glu Phe Leu Gln Ser Phe Val
                565                 570                 575

His Ile Val Gln Met Phe Ile Asn Thr Ser
            580                 585

<210> SEQ ID NO 34
<211> LENGTH: 586
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 (E46K) mutant
      with long linker

<400> SEQUENCE: 34

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285
```

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Glu
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Gly Gly Gly Ser Gly Gly Gly Ser Gly Gly
    450                 455                 460

Gly Gly Ser Gly Gly Gly Ser Asn Trp Val Asn Val Ile Ser Asp
465                 470                 475                 480

Leu Lys Lys Ile Glu Asp Leu Ile Gln Ser Met His Ile Asp Ala Thr
                485                 490                 495

Leu Tyr Thr Glu Ser Asp Val His Pro Ser Cys Lys Val Thr Ala Met
            500                 505                 510

Lys Cys Phe Leu Leu Lys Leu Gln Val Ile Ser Leu Glu Ser Gly Asp
        515                 520                 525

Ala Ser Ile His Asp Thr Val Glu Asn Leu Ile Ile Leu Ala Asn Asn
    530                 535                 540

Ser Leu Ser Ser Asn Gly Asn Val Thr Glu Ser Gly Cys Lys Glu Cys
545                 550                 555                 560

Glu Glu Leu Glu Glu Lys Asn Ile Lys Glu Phe Leu Gln Ser Phe Val
                565                 570                 575

His Ile Val Gln Met Phe Ile Asn Thr Ser
            580                 585

<210> SEQ ID NO 35
<211> LENGTH: 586
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 (V49D) mutant
      with long linker

<400> SEQUENCE: 35

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
            20                  25                  30

Val Met His Trp Val Lys Gln Lys Pro Gly Gln Gly Leu Glu Trp Ile
        35                  40                  45

```
Gly Tyr Ile Asn Pro Tyr Asn Asp Gly Thr Lys Tyr Asn Glu Lys Phe
     50                  55                  60
Lys Gly Lys Ala Thr Leu Thr Ser Asp Lys Ser Ser Thr Ala Tyr
 65                  70                  75                  80
Met Glu Leu Ser Ser Leu Thr Ser Glu Asp Ser Ala Val Tyr Tyr Cys
                 85                  90                  95
Ala Arg Gly Thr Tyr Tyr Gly Ser Arg Val Phe Asp Tyr Trp Gly
             100                 105                 110
Gln Gly Thr Thr Leu Thr Val Ser Ser Ala Ser Thr Lys Gly Pro Ser
             115                 120                 125
Val Phe Pro Leu Ala Pro Ser Ser Lys Ser Thr Ser Gly Gly Thr Ala
 130                 135                 140
Ala Leu Gly Cys Leu Val Lys Asp Tyr Phe Pro Glu Pro Val Thr Val
 145                 150                 155                 160
Ser Trp Asn Ser Gly Ala Leu Thr Ser Gly Val His Thr Phe Pro Ala
                 165                 170                 175
Val Leu Gln Ser Ser Gly Leu Tyr Ser Leu Ser Ser Val Val Thr Val
             180                 185                 190
Pro Ser Ser Ser Leu Gly Thr Gln Thr Tyr Ile Cys Asn Val Asn His
             195                 200                 205
Lys Pro Ser Asn Thr Lys Val Asp Lys Lys Val Glu Pro Lys Ser Cys
 210                 215                 220
Asp Lys Thr His Thr Cys Pro Pro Cys Pro Ala Pro Glu Leu Leu Gly
 225                 230                 235                 240
Gly Pro Asp Val Phe Leu Phe Pro Pro Lys Pro Lys Asp Thr Leu Met
                 245                 250                 255
Ile Ser Arg Thr Pro Glu Val Thr Cys Val Val Val Asp Val Ser His
             260                 265                 270
Glu Asp Pro Glu Val Lys Phe Asn Trp Tyr Val Asp Gly Val Glu Val
             275                 280                 285
His Asn Ala Lys Thr Lys Pro Arg Glu Glu Gln Tyr Asn Ser Thr Tyr
 290                 295                 300
Arg Val Val Ser Val Leu Thr Val Leu His Gln Asp Trp Leu Asn Gly
 305                 310                 315                 320
Lys Glu Tyr Lys Cys Lys Val Ser Asn Lys Ala Leu Pro Ala Pro Glu
                 325                 330                 335
Glu Lys Thr Ile Ser Lys Ala Lys Gly Gln Pro Arg Glu Pro Gln Val
             340                 345                 350
Tyr Thr Leu Pro Pro Ser Arg Asp Glu Leu Thr Lys Asn Gln Val Ser
             355                 360                 365
Leu Thr Cys Leu Val Lys Gly Phe Tyr Pro Ser Asp Ile Ala Val Glu
 370                 375                 380
Trp Glu Ser Asn Gly Gln Pro Glu Asn Asn Tyr Lys Thr Thr Pro Pro
 385                 390                 395                 400
Val Leu Asp Ser Asp Gly Ser Phe Phe Leu Tyr Ser Lys Leu Thr Val
                 405                 410                 415
Asp Lys Ser Arg Trp Gln Gln Gly Asn Val Phe Ser Cys Ser Val Met
             420                 425                 430
His Glu Ala Leu His Asn His Tyr Thr Gln Lys Ser Leu Ser Leu Ser
             435                 440                 445
Pro Gly Lys Ser Gly Gly Gly Ser Gly Gly Gly Ser Gly Gly
 450                 455                 460
Gly Gly Ser Gly Gly Gly Gly Ser Asn Trp Val Asn Val Ile Ser Asp
```

```
                465                 470                 475                 480
Leu Lys Lys Ile Glu Asp Leu Ile Gln Ser Met His Ile Asp Ala Thr
                    485                 490                 495

Leu Tyr Thr Glu Ser Asp Val His Pro Ser Cys Lys Val Thr Ala Met
                500                 505                 510

Lys Cys Phe Leu Leu Glu Leu Gln Asp Ile Ser Leu Glu Ser Gly Asp
            515                 520                 525

Ala Ser Ile His Asp Thr Val Glu Asn Leu Ile Ile Leu Ala Asn Asn
        530                 535                 540

Ser Leu Ser Ser Asn Gly Asn Val Thr Glu Ser Gly Cys Lys Glu Cys
545                 550                 555                 560

Glu Glu Leu Glu Glu Lys Asn Ile Lys Glu Phe Leu Gln Ser Phe Val
                565                 570                 575

His Ile Val Gln Met Phe Ile Asn Thr Ser
                580                 585

<210> SEQ ID NO 36
<211> LENGTH: 586
<212> TYPE: PRT
<213> ORGANISM: Artificial Sequence
<220> FEATURE:
<223> OTHER INFORMATION: Synthesized Fusion protein of anti-CD19 IgG1
      (4G7) heavy chain with SDIE modifications and IL15 (I50D) mutant
      with long linker

<400> SEQUENCE: 36

Glu Val Gln Leu Gln Gln Ser Gly Pro Glu Leu Ile Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Thr Tyr Tyr Gly Ser Arg Val Phe Asp Tyr Trp Gly
            100                 105                 110

Gln Gly Thr Thr Leu Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Asp Val Phe Leu Phe Pro Pro Lys Pro Lys Asp Thr Leu Met
            245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Ser Gly Gly Gly Ser Gly Gly Gly Ser Gly Gly
    450                 455                 460

Gly Gly Ser Gly Gly Gly Ser Asn Trp Val Asn Val Ile Ser Asp
465                 470                 475                 480

Leu Lys Lys Ile Glu Asp Leu Ile Gln Ser Met His Ile Asp Ala Thr
                485                 490                 495

Leu Tyr Thr Glu Ser Asp Val His Pro Ser Cys Lys Val Thr Ala Met
            500                 505                 510

Lys Cys Phe Leu Leu Glu Leu Gln Val Asp Ser Leu Glu Ser Gly Asp
        515                 520                 525

Ala Ser Ile His Asp Thr Val Glu Asn Leu Ile Ile Leu Ala Asn Asn
    530                 535                 540

Ser Leu Ser Ser Asn Gly Asn Val Thr Glu Ser Gly Cys Lys Glu Cys
545                 550                 555                 560

Glu Glu Leu Glu Glu Lys Asn Ile Lys Glu Phe Leu Gln Ser Phe Val
                565                 570                 575

His Ile Val Gln Met Phe Ile Asn Thr Ser
            580                 585

<210> SEQ ID NO 37
<211> LENGTH: 219
<212> TYPE: PRT
<213> ORGANISM: Artificial Sequence
<220> FEATURE:
<223> OTHER INFORMATION: Synthesized anti-CD19 IgG1 (4G7) light chain

<400> SEQUENCE: 37

Asp Ile Val Met Thr Gln Ala Ala Pro Ser Ile Pro Val Thr Pro Gly
1               5                   10                  15
```

Glu Ser Val Ser Ile Ser Cys Arg Ser Ser Lys Ser Leu Leu Asn Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Phe Thr Phe Gly Ala Gly Thr Lys Leu Glu Leu Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 38
<211> LENGTH: 588
<212> TYPE: PRT
<213> ORGANISM: Artificial Sequence
<220> FEATURE:
<223> OTHER INFORMATION: Synthesized Fusion protein of anti-FLT3 IgG1
      (BV10) heavy chain with SDIE modifications and IL15 mutant

<400> SEQUENCE: 38

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Leu His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Lys Gly Gly Ile Tyr Tyr Ala Asn His Tyr Tyr Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val

```
            145                 150                 155                 160
        Thr Val Ser Trp Asn Ser Gly Ala Leu Thr Ser Gly Val His Thr Phe
                        165                 170                 175

Pro Ala Val Leu Gln Ser Ser Gly Leu Tyr Ser Leu Ser Ser Val Val
                        180                 185                 190

Thr Val Pro Ser Ser Ser Leu Gly Thr Gln Thr Tyr Ile Cys Asn Val
                        195                 200                 205

Asn His Lys Pro Ser Asn Thr Lys Val Asp Lys Lys Val Glu Pro Lys
                        210                 215                 220

Ser Cys Asp Lys Thr His Thr Cys Pro Pro Cys Pro Ala Pro Glu Leu
        225                 230                 235                 240

Leu Gly Gly Pro Asp Val Phe Leu Phe Pro Pro Lys Pro Lys Asp Thr
                        245                 250                 255

Leu Met Ile Ser Arg Thr Pro Glu Val Thr Cys Val Val Val Asp Val
                        260                 265                 270

Ser His Glu Asp Pro Glu Val Lys Phe Asn Trp Tyr Val Asp Gly Val
                        275                 280                 285

Glu Val His Asn Ala Lys Thr Lys Pro Arg Glu Glu Gln Tyr Asn Ser
                        290                 295                 300

Thr Tyr Arg Val Val Ser Val Leu Thr Val Leu His Gln Asp Trp Leu
        305                 310                 315                 320

Asn Gly Lys Glu Tyr Lys Cys Lys Val Ser Asn Lys Ala Leu Pro Ala
                        325                 330                 335

Pro Glu Glu Lys Thr Ile Ser Lys Ala Lys Gly Gln Pro Arg Glu Pro
                        340                 345                 350

Gln Val Tyr Thr Leu Pro Pro Ser Arg Asp Glu Leu Thr Lys Asn Gln
                        355                 360                 365

Val Ser Leu Thr Cys Leu Val Lys Gly Phe Tyr Pro Ser Asp Ile Ala
                        370                 375                 380

Val Glu Trp Glu Ser Asn Gly Gln Pro Glu Asn Asn Tyr Lys Thr Thr
        385                 390                 395                 400

Pro Pro Val Leu Asp Ser Asp Gly Ser Phe Phe Leu Tyr Ser Lys Leu
                        405                 410                 415

Thr Val Asp Lys Ser Arg Trp Gln Gln Gly Asn Val Phe Ser Cys Ser
                        420                 425                 430

Val Met His Glu Ala Leu His Asn His Tyr Thr Gln Lys Ser Leu Ser
                        435                 440                 445

Leu Ser Pro Gly Lys Ser Gly Gly Gly Ser Gly Gly Gly Gly Ser
        450                 455                 460

Gly Gly Gly Gly Ser Gly Gly Gly Ser Asn Trp Val Asn Val Ile
        465                 470                 475                 480

Ser Asp Leu Lys Lys Ile Glu Asp Leu Ile Gln Ser Met His Ile Asp
                        485                 490                 495

Ala Thr Leu Tyr Thr Glu Ser Asp Val His Pro Ser Cys Lys Val Thr
                        500                 505                 510

Ala Met Lys Cys Phe Leu Leu Lys Leu Gln Val Ile Ser Leu Glu Ser
                        515                 520                 525

Gly Asp Ala Ser Ile His Asp Thr Val Glu Asn Leu Ile Ile Leu Ala
                        530                 535                 540

Asn Asn Ser Leu Ser Ser Asn Gly Asn Val Thr Glu Ser Gly Cys Lys
        545                 550                 555                 560

Glu Cys Glu Glu Leu Glu Glu Lys Asn Ile Lys Glu Phe Leu Gln Ser
                        565                 570                 575
```

Phe Val His Ile Val Gln Met Phe Ile Asn Thr Ser
                580                 585

<210> SEQ ID NO 39
<211> LENGTH: 220
<212> TYPE: PRT
<213> ORGANISM: Artificial Sequence
<220> FEATURE:
<223> OTHER INFORMATION: Synthesized anti-FLT3 IgG1 (BV10) light chain

<400> SEQUENCE: 39

Asp Ile Val Met Thr Gln Ser Pro Ser Leu Ser Val Ser Ala Gly
1               5                   10                  15

Glu Lys Val Thr Met Ser Cys Lys Ser Ser Gln Ser Leu Leu Asn Ser
                20                  25                  30

Gly Asn Gln Lys Asn Tyr Met Ala Trp Tyr Gln Lys Pro Gly Gln
            35                  40                  45

Pro Pro Lys Leu Leu Ile Tyr Gly Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Ala Gly Thr Lys Leu Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 40
<211> LENGTH: 583
<212> TYPE: PRT
<213> ORGANISM: Artificial Sequence
<220> FEATURE:
<223> OTHER INFORMATION: Synthesized Fusion protein of anti-FLT3 IgG1
      (4G8) heavy chain with SDIE modifications and IL15 mutant

<400> SEQUENCE: 40

Gln Val Gln Leu Gln Gln Pro Gly Ala Glu Leu Val Lys Pro Gly Ala
1               5                   10                  15

Ser Leu Lys Leu Ser Cys Lys Ser Ser Gly Tyr Thr Phe Thr Ser Tyr
                20                  25                  30

Trp Met His Trp Val Arg Gln Arg Pro Gly His Gly Leu Glu Trp Ile
            35                  40                  45

Gly Glu Ile Asp Pro Ser Asp Ser Tyr Lys Asp Tyr Asn Gln Lys Phe
        50                  55                  60

```
Lys Asp Lys Ala Thr Leu Thr Val Asp Arg Ser Ser Asn Thr Ala Tyr
 65                  70                  75                  80

Met His Leu Ser Ser Leu Thr Ser Asp Asp Ser Ala Val Tyr Tyr Cys
                 85                  90                  95

Ala Arg Ala Ile Thr Thr Thr Pro Phe Asp Phe Trp Gly Gln Gly Thr
            100                 105                 110

Thr Leu Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Asp
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Glu Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Ser Gly Gly Gly Gly Ser Gly Gly Gly Ser Gly Gly Gly Gly Gly Ser
    450                 455                 460

Gly Gly Gly Gly Ser Asn Trp Val Asn Val Ile Ser Asp Leu Lys Lys
465                 470                 475                 480

Ile Glu Asp Leu Ile Gln Ser Met His Ile Asp Ala Thr Leu Tyr Thr
```

-continued

```
                        485                 490                 495
Glu Ser Asp Val His Pro Ser Cys Lys Val Thr Ala Met Lys Cys Phe
            500                 505                 510

Leu Leu Lys Leu Gln Val Ile Ser Leu Glu Ser Gly Asp Ala Ser Ile
            515                 520                 525

His Asp Thr Val Glu Asn Leu Ile Ile Leu Ala Asn Asn Ser Leu Ser
            530                 535                 540

Ser Asn Gly Asn Val Thr Glu Ser Gly Cys Lys Glu Cys Glu Glu Leu
545                 550                 555                 560

Glu Glu Lys Asn Ile Lys Glu Phe Leu Gln Ser Phe Val His Ile Val
                565                 570                 575

Gln Met Phe Ile Asn Thr Ser
            580

<210> SEQ ID NO 41
<211> LENGTH: 214
<212> TYPE: PRT
<213> ORGANISM: Artificial Sequence
<220> FEATURE:
<223> OTHER INFORMATION: Synthesized anti-endoglin IgG1 (4G8) light
      chain

<400> SEQUENCE: 41

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Asn Ser Val Glu Thr
65                  70                  75                  80

Glu Asp Phe Gly Val Tyr Phe Cys Gln Gln Ser Asn Thr Trp Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 42
<211> LENGTH: 580
<212> TYPE: PRT
<213> ORGANISM: Artificial Sequence
<220> FEATURE:
```

<223> OTHER INFORMATION: Synthesized Fusion protein of anti-PSMA IgG1
      (J591) heavy chain with SDIE modifications and IL15 wild type

<400> SEQUENCE: 42

```
Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400
```

```
Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Ser Gly Gly
        435                 440                 445

Gly Gly Ser Gly Gly Gly Gly Ser Gly Gly Gly Gly Ser Gly Gly Gly
    450                 455                 460

Gly Ser Asn Trp Val Asn Val Ile Ser Asp Leu Lys Lys Ile Glu Asp
465                 470                 475                 480

Leu Ile Gln Ser Met His Ile Asp Ala Thr Leu Tyr Thr Glu Ser Asp
                485                 490                 495

Val His Pro Ser Cys Lys Val Thr Ala Met Lys Cys Phe Leu Leu Glu
            500                 505                 510

Leu Gln Val Ile Ser Leu Glu Ser Gly Asp Ala Ser Ile His Asp Thr
        515                 520                 525

Val Glu Asn Leu Ile Ile Leu Ala Asn Asn Ser Leu Ser Ser Asn Gly
    530                 535                 540

Asn Val Thr Glu Ser Gly Cys Lys Glu Cys Glu Glu Leu Glu Glu Lys
545                 550                 555                 560

Asn Ile Lys Glu Phe Leu Gln Ser Phe Val His Ile Val Gln Met Phe
                565                 570                 575

Ile Asn Thr Ser
            580

<210> SEQ ID NO 43
<211> LENGTH: 580
<212> TYPE: PRT
<213> ORGANISM: Artificial Sequence
<220> FEATURE:
<223> OTHER INFORMATION: Synthesized Fusion protein of anti-PSMA IgG1
      (J591) heavy chain with SDIE modifications and IL15 (E46K) mutant

<400> SEQUENCE: 43

Glu Val Gln Leu Gln Gln Ser Gly Pro Glu Leu Val Lys Pro Gly Thr
1               5                   10                  15

Ser Val Arg Ile Ser Cys Lys Thr Ser Gly Tyr Thr Phe Thr Glu Tyr
            20                  25                  30

Thr Ile His Trp Val Lys Gln Ser His Gly Lys Ser Leu Glu Trp Ile
        35                  40                  45

Gly Asn Ile Asn Pro Asn Asn Gly Gly Thr Thr Tyr Asn Gln Lys Phe
    50                  55                  60

Glu Asp Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
```

```
                165                 170                 175
Leu Tyr Ser Leu Ser Ser Val Thr Val Pro Ser Ser Leu Gly
            180                 185             190

Thr Gln Thr Tyr Ile Cys Asn Val Asn His Lys Pro Ser Asn Thr Lys
        195                 200             205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Asp Val Phe Leu
225             230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
            290                 295                 300

Thr Val Leu His Gln Asp Trp Leu Asn Gly Lys Glu Tyr Lys Cys Lys
305             310                 315                 320

Val Ser Asn Lys Ala Leu Pro Ala Pro Glu Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385             390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Ser Gly Gly
            435                 440                 445

Gly Gly Ser Gly Gly Gly Ser Gly Gly Gly Ser Gly Gly Gly
450                 455                 460

Gly Ser Asn Trp Val Asn Val Ile Ser Asp Leu Lys Lys Ile Glu Asp
465             470                 475                 480

Leu Ile Gln Ser Met His Ile Asp Ala Thr Leu Tyr Thr Glu Ser Asp
                485                 490                 495

Val His Pro Ser Cys Lys Val Thr Ala Met Lys Cys Phe Leu Leu Lys
            500                 505                 510

Leu Gln Val Ile Ser Leu Glu Ser Gly Asp Ala Ser Ile His Asp Thr
            515                 520                 525

Val Glu Asn Leu Ile Ile Leu Ala Asn Asn Ser Leu Ser Ser Asn Gly
530             535                 540

Asn Val Thr Glu Ser Gly Cys Lys Glu Cys Glu Glu Leu Glu Glu Lys
545                 550                 555                 560

Asn Ile Lys Glu Phe Leu Gln Ser Phe Val His Ile Val Gln Met Phe
                565                 570                 575

Ile Asn Thr Ser
            580
```

```
<210> SEQ ID NO 44
<211> LENGTH: 214
<212> TYPE: PRT
<213> ORGANISM: Artificial Sequence
<220> FEATURE:
<223> OTHER INFORMATION: Synthesized anti-PSMA IgG1 (J591) light chain

<400> SEQUENCE: 44

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```